(12) United States Patent
Sigalov

(10) Patent No.: US 12,419,839 B2
(45) Date of Patent: *Sep. 23, 2025

(54) METHODS AND COMPOSITIONS FOR TARGETED DELIVERY OF PROTEIN FRAGMENTS

(71) Applicant: Signablok, Inc., Shrewsbury, MA (US)

(72) Inventor: Alexander Sigalov, Worcester, MA (US)

(73) Assignee: SIGNABLOK, INC., Shrewsbury, MA (US)

(*) Notice: Subject to any disclaimer, the term of this patent is extended or adjusted under 35 U.S.C. 154(b) by 1091 days.

This patent is subject to a terminal disclaimer.

(21) Appl. No.: 17/388,783

(22) Filed: Jul. 29, 2021

(65) Prior Publication Data

US 2022/0047512 A1    Feb. 17, 2022

Related U.S. Application Data

(63) Continuation-in-part of application No. 13/028,238, filed on Feb. 16, 2011, now Pat. No. 11,097,020, (Continued)

(51) Int. Cl.
*A61K 9/16* (2006.01)
*A61K 31/337* (2006.01)
(Continued)

(52) U.S. Cl.
CPC .......... *A61K 9/1617* (2013.01); *A61K 31/337* (2013.01); *A61K 31/4745* (2013.01); (Continued)

(58) Field of Classification Search
CPC ................ A61K 9/1617; A61K 31/337; A61K 31/4745; A61K 31/704; A61K 31/7048;
(Continued)

(56) References Cited

U.S. PATENT DOCUMENTS

| 5,059,528 A | 10/1991 | Bollen et al. ................. 435/69.4 |
| 5,128,318 A | 7/1992 | Levine et al. .................... 514/2 |

(Continued)

FOREIGN PATENT DOCUMENTS

| WO | WO1987002061 | 4/1987 |
| WO | WO2001038395 | 5/2001 |

(Continued)

OTHER PUBLICATIONS

Pankhurst, G. et al. J Lipid Res. Feb. 2003;44(2):349-55. (Year: 2003).*

(Continued)

*Primary Examiner* — Carlos A Azpuru
(74) *Attorney, Agent, or Firm* — Medlen & Carroll, LLP

(57) ABSTRACT

The present invention is related to the field of targeted drug delivery. In particular, the particles and compositions described herein are used to deliver drugs to treat the diseases and conditions of interest. These particles and compositions include, but are not limited to, the lipopeptide complexes that mimic human high-density lipoproteins but contain apolipoprotein fragments or combination thereof.

40 Claims, 22 Drawing Sheets

Specification includes a Sequence Listing.

Related U.S. Application Data which is a continuation-in-part of application No. PCT/US2010/052117, filed on Oct. 10, 2010.

(60) Provisional application No. 61/250,465, filed on Oct. 9, 2009.

(51) Int. Cl.
*A61K 31/4745* (2006.01)
*A61K 31/704* (2006.01)
*A61K 31/7048* (2006.01)
*A61K 47/64* (2017.01)
*A61K 47/68* (2017.01)
*A61K 47/69* (2017.01)

(52) U.S. Cl.
CPC ........ *A61K 31/704* (2013.01); *A61K 31/7048* (2013.01); *A61K 47/64* (2017.08); *A61K 47/6835* (2017.08); *A61K 47/6923* (2017.08); *A61K 47/6929* (2017.08)

(58) Field of Classification Search
CPC ............... A61K 47/64; A61K 47/6835; A61K 47/6923; A61K 9/51; A61K 47/6917
See application file for complete search history.

(56) References Cited

U.S. PATENT DOCUMENTS

| | | | |
|---|---|---|---|
| 5,192,264 A | 3/1993 | Fossel | 604/4 |
| 5,652,339 A | 7/1997 | Lerch et al. | 530/359 |
| 5,676,926 A | 10/1997 | Platzek et al. | 424/9.3 |
| 5,676,928 A | 10/1997 | Klaveness et al. | 424/9.321 |
| 5,840,688 A | 11/1998 | Tso | 514/12 |
| 5,965,542 A | 10/1999 | Wasan et al. | 514/44 |
| 6,004,925 A | 12/1999 | Dasseux et al. | 514/13 |
| 6,037,323 A | 3/2000 | Dasseux et al. | 514/12 |
| 6,046,166 A | 4/2000 | Dasseux et al. | 530/326 |
| 6,139,819 A | 10/2000 | Unger et al. | 424/9.52 |
| 6,248,353 B1 | 6/2001 | Singh | 424/450 |
| 6,306,433 B1 | 10/2001 | Andersson et al. | 424/450 |
| 6,514,523 B1 | 2/2003 | Sparks | 424/450 |
| 6,617,134 B1 | 9/2003 | Sirtori et al. | 435/69.7 |
| 6,953,840 B2 | 10/2005 | Zhu et al. | 514/12 |
| 7,288,266 B2 | 10/2007 | Smyth-Templeton et al. | 424/450 |
| 7,435,717 B2 | 10/2008 | Bisgaier et al. | 514/2 |
| 7,449,301 B2 | 11/2008 | Matozaki | 435/7.1 |
| 7,588,751 B2 | 9/2009 | Ueda et al. | 424/9.1 |
| 7,662,410 B2 | 2/2010 | Sligar et al. | 424/499 |
| 7,740,854 B2 | 6/2010 | Low et al. | 424/184.1 |
| 7,824,709 B2 | 11/2010 | Ryan et al. | 424/489 |
| 8,013,116 B2 | 9/2011 | Faure et al. | 530/326 |
| 8,278,271 B2 | 10/2012 | Sigalov | 514/9.7 |
| 8,513,185 B2 | 8/2013 | Sigalov | 514/1.4 |
| 8,614,188 B2 | 12/2013 | Sigalov | 514/13.8 |
| 9,255,136 B2 | 2/2016 | Gibot | 514/21.4 |
| 9,273,111 B2 | 3/2016 | Faure et al. | 530/326 |
| 9,657,081 B2 | 5/2017 | Gibot et al. | 514/16.4 |
| 9,815,883 B2 | 11/2017 | Gibot | 514/1.4 |
| 9,981,004 B2 | 5/2018 | Sigalov | 514/1.4 |
| 10,138,276 B2 | 11/2018 | Sigalov | 530/300 |
| 10,538,558 B2 | 1/2020 | Sigalov | 530/300 |
| 2001/0002251 A1 | 5/2001 | Woodburn | 424/9.5 |
| 2002/0110604 A1 | 8/2002 | Babish | 424/725 |
| 2002/0156007 A1 | 10/2002 | Graversen | 435/69.1 |
| 2002/0177558 A1 | 11/2002 | Meyerhoff et al. | 514/12 |
| 2003/0008014 A1 | 1/2003 | Shelness | 424/499 |
| 2003/0045460 A1 | 3/2003 | Fogelman et al. | 514/12 |
| 2003/0087819 A1 | 5/2003 | Bielicki | 514/12 |
| 2003/0171277 A1 | 9/2003 | Fogelman et al. | 514/12 |
| 2003/0181372 A1 | 9/2003 | Oda | 514/12 |
| 2004/0067873 A1 | 4/2004 | Dasseux et al. | 514/2 |
| 2004/0077541 A1 | 4/2004 | Zhu et al. | 514/12 |
| 2004/0176473 A1 | 9/2004 | Unger | 514/2 |
| 2004/0229794 A1 | 11/2004 | Ryan | 424/489 |
| 2004/0254120 A1 | 12/2004 | Fogelman et al. | 514/12 |
| 2004/0266660 A1 | 12/2004 | Hubsch et al. | 514/200 |
| 2004/0266671 A1 | 12/2004 | Fogelman et al. | 435/6 |
| 2005/0239136 A1 | 10/2005 | Hazen et al. | 435/7.1 |
| 2005/0281740 A1 | 12/2005 | Gong | 514/12 |
| 2006/0099148 A1 | 5/2006 | Fisher et al. | 424/501 |
| 2006/0204566 A1 | 9/2006 | Smyth-Templeton | 424/450 |
| 2006/0205643 A1 | 9/2006 | Cuzzocrea et al. | 514/21 |
| 2006/0217312 A1 | 9/2006 | Dasseux | 424/520 |
| 2006/0257466 A1 | 11/2006 | Kim | 424/450 |
| 2007/0065432 A1 | 3/2007 | Xu et al. | 435/320.1 |
| 2007/0172653 A1 | 7/2007 | Berkland | 428/402 |
| 2007/0243136 A1 | 10/2007 | Fisher et al. | 424/9.32 |
| 2008/0020400 A1 | 1/2008 | Caulfield | 435/7.1 |
| 2008/0286353 A1 | 11/2008 | Gregoriadis | 514/44 |
| 2009/0004113 A1 | 1/2009 | Wolf | 424/9.3 |
| 2009/0012025 A1 | 1/2009 | Hotchkiss et al. | 514/44 |
| 2009/0068264 A1 | 3/2009 | Richardson et al. | 514/183 |
| 2009/0075899 A1 | 3/2009 | Sigalov | 514/9.7 |
| 2009/0110739 A1 | 4/2009 | Lacko | 424/491 |
| 2009/0311191 A1 | 12/2009 | Annapragada et al. | 424/9.3 |
| 2009/0312402 A1 | 12/2009 | Contag | 514/44 |
| 2010/0311595 A1 | 12/2010 | Ryan | 424/489 |
| 2011/0256224 A1 | 10/2011 | Sigalov | 424/489 |
| 2011/0312899 A1 | 12/2011 | Sood et al. | 424/499 |
| 2013/0039948 A1 | 2/2013 | Sigalov | 530/300 |
| 2013/0045161 A1 | 2/2013 | Sigalov | 424/489 |

FOREIGN PATENT DOCUMENTS

| | | |
|---|---|---|
| WO | PCT/US10/52117 | 4/2011 |
| WO | PCT/US10/52566 | 4/2011 |

OTHER PUBLICATIONS

Briley-Saebo et al. Circulation (2008), 117(25), 3206-3215. (Year: 2008).*
Hafez et al. Gene Therapy (2001) 8, 1188-1196. (Year: 2001).*
Ashwini et al. (Peptides 27 (2006) 2858â2866). (Year: 2006).*
Sigalov et al. Chemistry and Physics of Lipids 113 (2001) 133-146 (Year: 2001).*
Hamaguchi et al. British Journal of Cancer (2005) 92, 1240-1246 (Year: 2005).*
U.S. Appl. No. 12/895,454 (U.S. Pat. No. 10,138,4276, Feb. 14, 2013, Alexander B. Sigalov, filed Sep. 30, 2010.
Banga. *Therapeutic peptides and proteins : formulation, processing, and delivery systems.* 2nd ed. Boca Raton, FL: Taylor & Francis Group; 375 pages, 2006.
Bennasroune, et al., "Transmembrane peptides as inhibitors of ErbB receptor signaling", *Mol Biol Cell*, 15:3464-3474. 2004.
Cuvier, et al., "A First-in-Man Safety and Pharmacokinetics Study of Nangibotide, a New Modulator of Innate Immune Response through TREM-1 Receptor Inhibition." *Br J Clin Pharmacol*, 84(10):2270-2279 (2018).
Garda, "Structure-function relationships in human apolipoprotein A-I: role of a central helix pair". *Future Lipidol Volume* 2(1):95-104, 2007.
Gibot, et al., "Modulation of the Triggering Receptor Expressed on the Myeloid Cell Type 1 Pathway in Murine Septic Shock." *Infect Immun*, 74(5):2823-2830 (2006).
Gibot, et al., "TREM-1 Promotes Survival During Septic Shock in Mice." *Eur J Immunol*, 37(2):456-466 (2007).
Gibot, et al., "Effects of the TREM 1 Pathway Modulation During Hemorrhagic Shock in Rats." *Shock*, 32(6):633-637 (2009).
Gursky "Hot Spots in Apolipoprotein A-II Misfolding and Amyloidosis in Mice and Men." *FEBS Lett*, 588(6):845-850 (2014).
Joffre, et al., "Genetic and Pharmacological Inhibition of TREM-1 Limits the Development of Experimental Atherosclerosis." *J Am Coll Cardiol*, 68(25):2776-2793 (2016).
Kim, et al., "Targeted delivery of siRNA against hepatitis C virus by apolipoprotein A-I-bound cationic liposomes". *J Hepatol* 50:479-88, 2009.

(56) References Cited

OTHER PUBLICATIONS

Oda, et al., "Reconstituted high-density lipoprotein enriched with the polyene antibiotic amphotericin" B. *J Lipid Res* 47:260-7, 2006.

Rojas, et al., "TREM-1 blockade prevents vitreoretinal neovascularization in a mouse model of retinopathy of prematurity." vol. 58, Issue 8 ARVO Annual Meeting Abstract (2017 ARVO Annual Meeting, held in Baltimore, MD, May 7-11, 2017. *Investigative Ophthalmology & Visual Science* Jun. 2017, vol. 58, 3452, pp. 1-2, 2017.

Rojas, et al., "Blockade of TREM-1 Prevents Vitreoretinal Neovascularization in Mice with Oxygen-Induced Retinopathy." *Biochim Biophys Acta*, 1864(9 Pt B):2761-2768 (2018).

Shen, et al., "Diagnostic Magnetic Resonance Imaging of Atherosclerosis in Apolipoprotein E Knockout Mouse Model Using Macrophage-Targeted Gadolinium-Containing Synthetic Lipopeptide Nanoparticles." *PLoS One*, 10(11):e0143453, pp. 1-15, (2015).

Shen and Sigalov, "SARS Coronavirus Fusion Peptide-Derived Sequence Suppresses Collagen-Induced Arthritis in DBA/1J Mice", *Sci Rep*, 6:28672, pp. 1-15, 2016.

Shen and Sigalov, "Rationally designed ligand-independent peptide inhibitors of TREM-1 ameliorate collagen-induced arthritis", *J Cell Mol Med*, 21:2524-2534. 2017A.

Shen and Sigalov, "Novel TREM-1 Inhibitors Attenuate Tumor Growth and Prolong Survival in Experimental Pancreatic Cancer." *Mol Pharm*, 14(12):4572-4582. 2017B.

Sigalov, "Nature-Inspired Nanoformulations for Contrast-Enhanced in Vivo MR Imaging of Macrophages." *Contrast Media Mol Imaging*, 9(5):372-382, 2014A.

Sigalov, "A novel ligand-independent peptide inhibitor of TREM-1 suppresses tumor growth in human lung cancer xenografts and prolongs survival of mice with lipopolysaccharide-induced septic shock", *Int Immunopharmacol*, 21:208-219. 2014B.

Vlieghe, et al., "Synthetic Therapeutic Peptides: Science and Market." *Drug Discov Today*, 15(1-2):40-56 (2010).

Zhou, et al., "TREM-1 Inhibition Attenuates Inflammation and Tumor within the Colon." *Int Immunopharmacol*, 17(2):155-161 (2013).

International Search Report dated Jul. 29, 2011, PCT 2010-2177.

\* cited by examiner

METHODS AND COMPOSITIONS FOR TARGETED DELIVERY OF PROTEIN FRAGMENTS

CROSS-REFERENCE TO A RELATED APPLICATION

This application is a continuation-in-part of non-provisional U.S. patent application Ser. No. 13/028,238, filed on Feb. 16, 2011, which is a continuation-in-part application of International Patent Application Serial No. PCT/US10/52117, filed on Oct. 10, 2010, which claims priority to U.S. provisional application Ser. No. 61/250,465, filed on Oct. 9, 2009. The entire content of the aforementioned applications is incorporated herein by reference.

A Sequence Listing has been submitted in an ASCII text file named "19903.txt" created on Nov. 3, 2021, consisting of 16,384 bytes, the entire content of which is herein incorporated by reference.

FIELD OF THE INVENTION

The present invention is related to the field of targeted drug delivery. In particular, the particles and compositions described herein are used to deliver drugs to treat the diseases and conditions of interest. These particles and compositions include, but are not limited to, a lipopeptide complex (e.g., a high-density lipoprotein) and contain an apolipoprotein fragment or combinations thereof.

BACKGROUND OF THE INVENTION

The use of non-viral nanoparticulate systems for the delivery of therapeutic agents is receiving considerable attention for medical and pharmaceutical applications. The increasing interest results from the fact that these systems can be designed to meet specific physicochemical requirements, and they display low toxic and immunogenic effects. Among potential cellular targets by drug-loaded nanoparticles, macrophages are considered because they play a central role in inflammation and they act as reservoirs for microorganisms that are involved with deadly infectious diseases. The most common and potent drugs used in the treatment of cancer, bacterial infectious diseases, and other macrophage-mediated diseases often induce unwanted side effects, when applied as a free form, due to the necessity of high doses to induce a satisfactory effect. This could result in their systemic spreading, a lack of bioavailability at the desired sites, and a short half-life. Therefore, the use of drug-loaded nanoparticles represents a good alternative to avoid, or at least decrease, side effects and increase efficacy.

What is needed in the art is a high-affinity macrophage-targeted delivery vehicle that can freely enter macrophage-rich sites of interest, such as atherosclerotic plaques or tumor sites, and that increases drug concentrations at these sites at a significantly reduced dosage and systemic toxicity.

SUMMARY OF THE INVENTION

The present invention is related to the field of targeted drug delivery. In particular, the particles and compositions described herein are used to deliver drugs to treat the diseases and conditions of interest. These particles and compositions include, but are not limited to, a lipopeptide complex (e.g., a high-density lipoprotein) and contain an apolipoprotein fragment or combinations thereof.

In one embodiment, the present invention contemplates a composition comprising a reconstituted lipoprotein nanoparticle comprising: i) a plurality of phospholipids; ii) at least one apolipoprotein fragment comprising a modification, wherein said modification comprises one or two sulfoxidized methionine residues and not a modified tyrosine residue; and iii) at least one therapeutic agent attached to said nanoparticle. In one embodiment, the at least one apolipoprotein fragment further comprises said modification selected from the group consisting of halogenation, hydroxylation, peroxidation, dimerization, sulfoxidation and nitration. In one embodiment, the at least one apolipoprotein fragment is selected from the group consisting of an apolipoprotein A-I, an apolipoprotein A-II and an apolipoprotein A-IV. In one embodiment, the at least one apolipoprotein fragment is selected from the group consisting of an apolipoprotein C-I, an apolipoprotein C-II and an apolipoprotein C-III. In one embodiment, the at least one apolipoprotein fragment is an apolipoprotein E. In one embodiment, the nanoparticle further comprises a targeting agent selected from the group consisting of an apo E-derived lipopeptide, an apo A-I mimetic peptide, a murine MDA2 antibody, a murine E06 antibody, a human IK17 antibody and a gold particle. In one embodiment, the at least one apolipoprotein fragment is an amphipathic apolipoprotein fragment. In one embodiment, the therapeutic agent is selected from the group consisting of anticancer agents, antibacterial agents, antiviral agents, autoimmune agents, anti-inflammatory agents, cardiovascular agents, antioxidant agents, and therapeutic peptide agents. In one embodiment, the therapeutic agent is selected from the group consisting of paclitaxel, valrubicin, doxorubicin, taxotere, campotechin, and etoposide. In one embodiment, the plurality of phospholipids further comprise at least one lipid that is selected from the group consisting of a cholesterol, a cholesteryl ester, a glycolipid, a sphingolipid, a cationic lipid, a diacylglycerol, and a triacylglycerol. In one embodiment, the plurality of phospholipids are selected from the group consisting of phosphatidylcholine (PC), phosphatidylethanolamine (PE), phosphatidylserine (PS), phosphatidylinositol (PI), phosphatidylglycerol (PG), cardiolipin (CL), sphingomyelin (SM), and phosphatidic acid (PA). In one embodiment, the cationic lipid is 1,2-dioleoyl-3-trimethylammonium-propane (DOTAP). In one embodiment, the plurality of phospholipids further comprises polyethylene glycol(PEG)ylated. In one embodiment, the nanoparticle has a diameter of less than about 100 nm. In one embodiment, the composition is a pharmaceutical composition comprising a pharmaceutically acceptable carrier. In one embodiment, the nanoparticle has a diameter ranging between approximately 5-25 nanometers. In one embodiment, the plurality of phospholipids further comprise a chelating agent. In one embodiment, at least one of said plurality of phospholipids is modified. In one embodiment, the modified apolipoprotein fragment comprises a secondary structure that is unchanged as compared to an unmodified apolipoprotein. In one embodiment, the nanoparticle is discoidal.

In one embodiment, the present invention contemplates a reconstituted lipoprotein nanoparticle comprising: i) a triglyceride-cholesterol ester core surrounded by a plurality of phospholipids; ii) at least one apolipoprotein fragment comprising a modification, wherein said modification comprises one or two sulfoxidized methionine residues and not a modified tyrosine residue; and iii) at least one therapeutic agent attached to said nanoparticle. In one embodiment, the at least one apolipoprotein fragment further comprises said modification selected from the group consisting of halogenation, hydroxylation, peroxidation, dimerization, sulfoxidation and nitration. In one embodiment, the at least one apolipoprotein fragment is selected from the group consisting of an apolipoprotein A-I, an apolipoprotein A-II and an apolipoprotein A-IV. In one embodiment, the at least one apolipoprotein fragment is selected from the group consisting of an apolipoprotein C-I, an apolipoprotein C-II and an apolipoprotein C-III. In one embodiment, the at least one apolipoprotein fragment is apolipoprotein E. In one embodiment, the nanoparticle further comprises a targeting agent selected from the group consisting of an apo E-derived lipopeptide, an apo A-I mimetic peptide, a murine MDA2 antibody, a murine E06 antibody, a human IK17 antibody and a gold particle. In one embodiment, at least one said apolipoprotein fragments is an amphipathic apolipoprotein. In one embodiment, the therapeutic agent is selected from the group consisting of anticancer agents, antibacterial agents, antiviral agents, autoimmune agents, anti-inflammatory agents, cardiovascular agents, antioxidant agents, and therapeutic peptide agents. In one embodiment, the therapeutic agent is selected from the group consisting of paclitaxel, valrubicin, doxorubicin, taxotere, campotechin, and etoposide. In one embodiment, the plurality of phospholipids further comprise at least one lipid that is selected from the group consisting of a cholesterol, a cholesteryl ester, a glycolipid, a sphingolipid, a cationic lipid, a diacylglycerol, and a triacylglycerol. In one embodiment, the plurality of phospholipids are selected from the group consisting of phosphatidylcholine (PC), phosphatidylethanolamine (PE), phosphatidylserine (PS), phosphatidylinositol (PI), phosphatidylglycerol (PG), cardiolipin (CL), sphingomyelin (SM), and phosphatidic acid (PA). In one embodiment, the cationic lipid is 1,2-dioleoyl-3-trimethylammonium-propane (DOTAP). In one embodiment, the plurality of phospholipids further comprise polyethylene glycol(PEG)ylated. In one embodiment, the nanoparticle has a diameter of less than about 100 nm. In one embodiment, the nanoparticle is a pharmaceutical composition comprising a pharmaceutically acceptable carrier. In one embodiment, the nanoparticle has a diameter ranging between approximately 5-25 nanometers. In one embodiment, the plurality of phospholipids further comprise a chelating agent. In one embodiment, at least one of said plurality of phospholipids is modified. In one embodiment the modified apolipoprotein fragment comprises a secondary structure that is unchanged as compared to an unmodified apolipoprotein. In one embodiment, the nanoparticle is spherical.

In one embodiment, the present invention contemplates a composition comprising a reconstituted lipoprotein nanoparticle comprising: i) a plurality of phospholipids; ii) at least one apolipoprotein fragment; and iii) at least one therapeutic agent. In one embodiment, the at least one apolipoprotein fragment further comprises a modification selected from the group consisting of halogenation, hydroxylation, oxidation, peroxidation, dimerization, sulfoxidation and nitration. In one embodiment, said sulfoxidation comprises one or two sulfoxidized methionine residues and not a modified tyrosine residue. In one embodiment, the at least one apolipoprotein fragment is selected from the group consisting of an apolipoprotein A-I, an apolipoprotein A-II and an apolipoprotein A-IV. In one embodiment, the at least one apolipoprotein fragment is selected from the group consisting of an apolipoprotein C-I, an apolipoprotein C-II and an apolipoprotein C-III. In one embodiment, the at least one apolipoprotein fragment is an apolipoprotein E. In one embodiment, the nanoparticle further comprises a targeting agent selected from the group consisting of an apo E-derived lipopeptide, an apo A-I mimetic peptide, a murine MDA2 antibody, a murine E06 antibody, a human IK17 antibody and a gold particle. In one embodiment, the at least one apolipoprotein fragment is an amphipathic apolipoprotein fragment. In one embodiment, the therapeutic agent is incorporated within the nanoparticle. In one embodiment, the therapeutic agent is encapsulated within the nanoparticle. In one embodiment, the therapeutic agent is conjugated to the nanoparticle. In one embodiment, the therapeutic agent is attached to the nanoparticle. In one embodiment, the therapeutic agent is selected from the group consisting of anticancer agents, antibacterial agents, antiviral agents, autoimmune agents, anti-inflammatory agents, cardiovascular agents, antioxidant agents, and therapeutic peptide agents. In one embodiment, the therapeutic agent is selected from the group consisting of paclitaxel, valrubicin, doxorubicin, taxotere, campotechin, and etoposide. In one embodiment, the plurality of phospholipids further comprise at least one lipid that is selected from the group consisting of a cholesterol, a cholesteryl ester, a glycolipid, a sphingolipid, a cationic lipid, a diacylglycerol, and a triacylglycerol. In one embodiment, the plurality of phospholipids are selected from the group consisting of phosphatidylcholine (PC), phosphatidylethanolamine (PE), phosphatidylserine (PS), phosphatidylinositol (PI), phosphatidylglycerol (PG), cardiolipin (CL), sphingomyelin (SM), and phosphatidic acid (PA). In one embodiment, the cationic lipid is 1,2-dioleoyl-3-trimethylammonium-propane (DOTAP). In one embodiment, the plurality of phospholipids further comprises polyethylene glycol(PEG)ylated. In one embodiment, the nanoparticle has a diameter of less than about 100 nm. In one embodiment, the composition is a pharmaceutical composition comprising a pharmaceutically acceptable carrier. In one embodiment, the nanoparticle has a diameter ranging between approximately 5-25 nanometers. In one embodiment, the plurality of phospholipids further comprise a chelating agent. In one embodiment, at least one of said plurality of phospholipids is modified. In one embodiment, the modified apolipoprotein fragment comprises a secondary structure that is unchanged as compared to an unmodified apolipoprotein. In one embodiment, the nanoparticle is discoidal.

In one embodiment, the present invention contemplates a reconstituted lipoprotein nanoparticle comprising: i) a triglyceride-cholesterol ester core surrounded by a plurality of phospholipids; ii) at least one apolipoprotein fragment; and iii) at least one therapeutic agent. In one embodiment, the at least one apolipoprotein fragment further comprises a modification selected from the group consisting of halogenation, hydroxylation, oxidation, peroxidation, dimerization, sulfoxidation and nitration. In one embodiment, the sulfoxidation comprises one or two sulfoxidized methionine residues and not a modified tyrosine residue In one embodiment, the at least one apolipoprotein fragment is selected from the group consisting of an apolipoprotein A-I, an apolipoprotein A-II and an apolipoprotein A-IV. In one embodiment, the at least one apolipoprotein fragment is selected from the group consisting of an apolipoprotein C-I, an apolipoprotein C-II and an apolipoprotein C-III. In one embodiment, the at least one apolipoprotein fragment is apolipoprotein E. In one embodiment, the nanoparticle further comprises a targeting agent selected from the group consisting of an apo E-derived lipopeptide, an apo A-I mimetic peptide, a murine MDA2 antibody, a murine E06 antibody, a human IK17 antibody and a gold particle. In one embodiment, at least one said apolipoprotein fragments is an amphipathic apolipoprotein. In one embodiment, the therapeutic agent is incorporated within the nanoparticle. In one embodiment, the therapeutic agent is encapsulated within the nanoparticle. In one embodiment, the therapeutic agent is conjugated to the nanoparticle. In one embodiment, the therapeutic agent is attached to the nanoparticle. In one embodiment, the therapeutic agent is selected from the group consisting of anticancer agents, antibacterial agents, antiviral agents, autoimmune agents, anti-inflammatory agents, cardiovascular agents, antioxidant agents, and therapeutic peptide agents. In one embodiment, the therapeutic agent is selected from the group consisting of paclitaxel, valrubicin, doxorubicin, taxotere, campotechin, and etoposide. In one embodiment, the plurality of phospholipids further comprise at least one lipid that is selected from the group consisting of a cholesterol, a cholesteryl ester, a glycolipid, a sphingolipid, a cationic lipid, a diacylglycerol, and a triacylglycerol. In one embodiment, the plurality of phospholipids are selected from the group consisting of phosphatidylcholine (PC), phosphatidylethanolamine (PE), phosphatidylserine (PS), phosphatidylinositol (PI), phosphatidylglycerol (PG), cardiolipin (CL), sphingomyelin (SM), and phosphatidic acid (PA). In one embodiment, the cationic lipid is 1,2-dioleoyl-3-trimethylammonium-propane (DOTAP). In one embodiment, the plurality of phospholipids further comprise polyethylene glycol(PEG)ylated. In one embodiment, the nanoparticle has a diameter of less than about 100 nm. In one embodiment, the nanoparticle is a pharmaceutical composition comprising a pharmaceutically acceptable carrier. In one embodiment, the nanoparticle has a diameter ranging between approximately 5-25 nanometers. In one embodiment, the plurality of phospholipids further comprise a chelating agent. In one embodiment, at least one of said plurality of phospholipids is modified. In one embodiment the modified apolipoprotein fragment comprises a secondary structure that is unchanged as compared to an unmodified apolipoprotein. In one embodiment, the nanoparticle is spherical.

In one embodiment, the present invention contemplates a method comprising: a) providing; i) a patient exhibiting at least one symptom of a disease or disorder; ii) a pharmaceutically acceptable composition comprising a reconstituted lipoprotein nanoparticle comprising: A) a plurality of phospholipids; B) at least one apolipoprotein fragment comprising a modification, wherein said modification comprises one or two sulfoxidized methionine residues and not a modified tyrosine residue; and C) at least one therapeutic agent attached to said nanoparticle; and b) administering said pharmaceutically acceptable composition to the patient such that said at least one symptom of said macrophage-associated disease or disorder is reduced. In one embodiment, the disease or disorder comprises a macrophage-related disease or disorder. In one embodiment, the macrophage-related disease or disorder includes, but is not limited to, a heart disease, peripheral artery disease, restenosis, stroke, the cancers (e.g., sarcoma, lymphoma, leukemia, carcinoma and melanoma), bacterial infectious diseases, acquired immune deficiency syndrome (AIDS), allergic diseases, autoimmune diseases (e.g., rheumatoid arthritis, Sjogrens, scleroderma, systemic lupus erythematosus, non-specific vasculitis, Kawasaki's disease, psoriasis, type I diabetes, pemphigus vulgaris), granulomatous diseases (e.g., tuberculosis, sarcoidosis, lymphomatoid granulomatosis, Wegener's granulomatosus), Gaucher's disease, inflammatory diseases (e.g., sepsis, inflammatory lung diseases such as interstitial pneumonitis and asthma, inflammatory bowel disease such as Crohn's disease, and inflammatory arthritis), and transplant (e.g., heart/lung transplants) rejection reactions. In one embodiment, the disease or disorder comprises an autoimmune disease. In one embodiment, the autoimmune disease included, but is not limited to, diabetes mellitus, rheumatoid arthritis, multiple sclerosis, systemic lupus erythematosis, myasthenia gravis, scleroderma, Crohn's disease, ulcerative colitis, biliary cirrhosis, chronic active hepatitis, Hashimoto's thyroiditis, Graves' disease, Sjogren's syndrome, polyendocrine failure, vitiligo, peripheral neuropathy, rejection of transplantation, graft-versus-host disease, autoimmune polyglandular syndrome type I, acute glomerulonephritis, Addison's disease, adult-onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barre syndrome, hemochromatosis, Henoch-Schonlein purpura, idiopathic IgA nephropathy, juvenile rheumatoid arthritis, Lambert-Eaton syndrome, linear IgA dermatosis, myocarditis, narcolepsy, necrotizing vasculitis, neonatal lupus erythematosus (NLE) syndrome, nephrotic syndrome, pemphigoid, pemphigus, polymyositis, primary sclerosing cholangitis, psoriasis, rapidly-progressive glomerulonephritis (RPGN), Reiter's syndrome, stiff-man syndrome, thyroiditis, inflammatory bowel disease, skin disorders (e.g., atopic dermatitis, psoriasis, pemphigus vulgaris), cardiovascular problems (e.g., autoimmune pericarditis) and any combination thereof. In one embodiment, the at least one apolipoprotein fragment further comprises said modification selected from the group consisting of halogenation, hydroxylation, peroxidation, dimerization, sulfoxidation and nitration. In one embodiment, the at least one apolipoprotein fragment is selected from the group consisting of an apolipoprotein A-I, an apolipoprotein A-II and an apolipoprotein A-IV. In one embodiment, the at least one apolipoprotein fragment is selected from the group consisting of an apolipoprotein C-I, an apolipoprotein C-II and an apolipoprotein C-III. In one embodiment, the at least one apolipoprotein fragment is an apolipoprotein E. In one embodiment, the nanoparticle further comprises a targeting agent selected from the group consisting of an apo E-derived lipopeptide, an apo A-I mimetic peptide, a murine MDA2 antibody, a murine E06 antibody, a human IK17 antibody and a gold particle. In one embodiment, the at least one apolipoprotein fragment is an amphipathic apolipoprotein fragment. In one embodiment, the therapeutic agent is selected from the group consisting of anticancer agents, antibacterial agents, antiviral agents, autoimmune agents, anti-inflammatory agents, cardiovascular agents, antioxidant agents, and therapeutic peptide agents. In one embodiment, the therapeutic agent is selected from the group consisting of paclitaxel, valrubicin, doxorubicin, taxotere, campotechin, and etoposide. In one embodiment, the plurality of phospholipids further comprise at least one lipid that is selected from the group consisting of a cholesterol, a cholesteryl ester, a glycolipid, a sphingolipid, a cationic lipid, a diacylglycerol, and a triacylglycerol. In one embodiment, the plurality of phospholipids are selected from the group consisting of phosphatidylcholine (PC), phosphatidylethanolamine (PE), phosphatidylserine (PS), phosphatidylinositol (PI), phosphatidylglycerol (PG), cardiolipin (CL), sphingomyelin (SM), and phosphatidic acid (PA). In one embodiment, the cationic lipid is 1,2-dioleoyl-3-trimethylammonium-propane (DOTAP). In one embodiment, the plurality of phospholipids further comprises polyethylene glycol(PEG)ylated. In one embodiment, the nanoparticle has a diameter of less than about 100 nm. In one embodiment, the composition is a pharmaceutical composition comprising a pharmaceutically acceptable carrier. In one embodiment, the nanoparticle has a diameter ranging between approximately 5-25 nanometers. In one embodiment, the plurality of phospholipids further comprise a chelating agent. In one embodiment, at least one of said plurality of phospholipids is modified. In one embodiment, the modified apolipoprotein fragment comprises a secondary structure that is unchanged as compared to an unmodified apolipoprotein. In one embodiment, the nanoparticle is discoidal.

In one embodiment, the present invention contemplates a method, comprising, a) providing: i) a patient exhibiting at least one symptom of a disease or disorder; ii) a pharmaceutically acceptable composition comprising a reconstituted lipoprotein nanoparticle comprising: A) a triglyceride-cholesterol ester core surrounded by a plurality of phospholipids; B) at least one apolipoprotein fragment comprising a modification, wherein said modification comprises one or two sulfoxidized methionine residues and not a modified tyrosine residue; and C) at least one therapeutic agent attached to said nanoparticle; and b) administering said pharmaceutically acceptable composition to the patient such that said at least one symptom of said disease or disorder is reduced. In one embodiment, the disease or disorder comprises a macrophage-related disease or disorder. In one embodiment, the macrophage-related disease or disorder includes, but is not limited to, a heart disease, peripheral artery disease, restenosis, stroke, the cancers (e.g., sarcoma, lymphoma, leukemia, carcinoma and melanoma), bacterial infectious diseases, acquired immune deficiency syndrome (AIDS), allergic diseases, autoimmune diseases (e.g., rheumatoid arthritis, Sjogrens, scleroderma, systemic lupus erythematosus, non-specific vasculitis, Kawasaki's disease, psoriasis, type I diabetes, pemphigus vulgaris), granulomatous diseases (e.g., tuberculosis, sarcoidosis, lymphomatoid granulomatosis, Wegener's granulomatosus), Gaucher's disease, inflammatory diseases (e.g., sepsis, inflammatory lung diseases such as interstitial pneumonitis and asthma, inflammatory bowel disease such as Crohn's disease, and inflammatory arthritis), and transplant (e.g., heart/lung transplants) rejection reactions. In one embodiment, the disease or disorder comprises an autoimmune disease. In one embodiment, the autoimmune disease included, but is not limited to, diabetes mellitus, rheumatoid arthritis, multiple sclerosis, systemic lupus erythematosis, myasthenia gravis, scleroderma, Crohn's disease, ulcerative colitis, biliary cirrhosis, chronic active hepatitis, Hashimoto's thyroiditis, Graves' disease, Sjogren's syndrome, polyendocrine failure, vitiligo, peripheral neuropathy, rejection of transplantation, graft-versus-host disease, autoimmune polyglandular syndrome type I, acute glomerulonephritis, Addison's disease, adult-onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barre syndrome, hemochromatosis, Henoch-Schonlein purpura, idiopathic IgA nephropathy, juvenile rheumatoid arthritis, Lambert-Eaton syndrome, linear IgA dermatosis, myocarditis, narcolepsy, necrotizing vasculitis, neonatal lupus erythematosus (NLE) syndrome, nephrotic syndrome, pemphigoid, pemphigus, polymyositis, primary sclerosing cholangitis, psoriasis, rapidly-progressive glomerulonephritis (RPGN), Reiter's syndrome, stiff-man syndrome, thyroiditis, inflammatory bowel disease, skin disorders (e.g., atopic dermatitis, psoriasis, pemphigus vulgaris), cardiovascular problems (e.g., autoimmune pericarditis) and any combination thereof. In one embodiment, the at least one apolipoprotein fragment further comprises said modification selected from the group consisting of halogenation, hydroxylation, peroxidation, dimerization, sulfoxidation and nitration. In one embodiment, the at least one apolipoprotein fragment is selected from the group consisting of an apolipoprotein A-I, an apolipoprotein A-II and an apolipoprotein A-IV. In one embodiment, the at least one apolipoprotein fragment is selected from the group consisting of an apolipoprotein C-I, an apolipoprotein C-II and an apolipoprotein C-III. In one embodiment, the at least one apolipoprotein fragment is apolipoprotein E. In one embodiment, the nanoparticle further comprises a targeting agent selected from the group consisting of an apo E-derived lipopeptide, an apo A-I mimetic peptide, a murine MDA2 antibody, a murine E06 antibody, a human IK17 antibody and a gold particle. In one embodiment, at least one said apolipoprotein fragments is an amphipathic apolipoprotein. In one embodiment, the therapeutic agent is selected from the group consisting of anti-cancer agents, antibacterial agents, antiviral agents, autoimmune agents, anti-inflammatory agents, cardiovascular agents, antioxidant agents, and therapeutic peptide agents. In one embodiment, the therapeutic agent is selected from the group consisting of paclitaxel, valrubicin, doxorubicin, taxotere, campotechin, and etoposide. In one embodiment, the plurality of phospholipids further comprise at least one lipid that is selected from the group consisting of a cholesterol, a cholesteryl ester, a glycolipid, a sphingolipid, a cationic lipid, a diacylglycerol, and a triacylglycerol. In one embodiment, the plurality of phospholipids are selected from the group consisting of phosphatidylcholine (PC), phosphatidylethanolamine (PE), phosphatidylserine (PS), phosphatidylinositol (PI), phosphatidylglycerol (PG), cardiolipin (CL), sphingomyelin (SM), and phosphatidic acid (PA). In one embodiment, the cationic lipid is 1,2-dioleoyl-3-trimethylammonium-propane (DOTAP). In one embodiment, the plurality of phospholipids further comprise polyethylene glycol(PEG)ylated. In one embodiment, the nanoparticle has a diameter of less than about 100 nm. In one embodiment, the nanoparticle is a pharmaceutical composition comprising a pharmaceutically acceptable carrier. In one embodiment, the nanoparticle has a diameter ranging between approximately 5-25 nanometers. In one embodiment, the plurality of phospholipids further comprise a chelating agent. In one embodiment, at least one of said plurality of phospholipids is modified. In one embodiment the modified apolipoprotein fragment comprises a secondary structure that is unchanged as compared to an unmodified apolipoprotein. In one embodiment, the nanoparticle is spherical.

In one embodiment, the present invention contemplates a method: a) providing; i) a patient exhibiting at least one symptom of a disease or disorder; and ii) a pharmaceutically acceptable composition comprising a reconstituted lipoprotein nanoparticle comprising: A) a plurality of phospholipids; B) at least one apolipoprotein fragment; and C) at least one therapeutic agent; and b) administering said pharmaceutically acceptable composition to the patient such that said at least one symptom of said disease or disorder is reduced. In one embodiment, the disease or disorder comprises a macrophage-related disease or disorder. In one embodiment, the macrophage-related disease or disorder includes, but is not limited to, a heart disease, peripheral artery disease, restenosis, stroke, the cancers (e.g., sarcoma, lymphoma, leukemia, carcinoma and melanoma), bacterial infectious diseases, acquired immune deficiency syndrome (AIDS), allergic diseases, autoimmune diseases (e.g., rheumatoid arthritis, Sjogrens, scleroderma, systemic lupus erythematosus, non-specific vasculitis, Kawasaki's disease, psoriasis, type I diabetes, pemphigus vulgaris), granulomatous diseases (e.g., tuberculosis, sarcoidosis, lymphomatoid granulomatosis, Wegener's granulomatosus), Gaucher's disease, inflammatory diseases (e.g., sepsis, inflammatory lung diseases such as interstitial pneumonitis and asthma, inflammatory bowel disease such as Crohn's disease, and inflammatory arthritis), and transplant (e.g., heart/lung transplants) rejection reactions. In one embodiment, the disease or disorder comprises an autoimmune disease. In one embodiment, the autoimmune disease included, but is not limited to, diabetes mellitus, rheumatoid arthritis, multiple sclerosis, systemic lupus erythematosis, myasthenia gravis, scleroderma, Crohn's disease, ulcerative colitis, biliary cirrhosis, chronic active hepatitis, Hashimoto's thyroiditis, Graves' disease, Sjogren's syndrome, polyendocrine failure, vitiligo, peripheral neuropathy, rejection of transplantation, graft-versus-host disease, autoimmune polyglandular syndrome type I, acute glomerulonephritis, Addison's disease, adult-onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barre syndrome, hemochromatosis, Henoch-Schonlein purpura, idiopathic IgA nephropathy, juvenile rheumatoid arthritis, Lambert-Eaton syndrome, linear IgA dermatosis, myocarditis, narcolepsy, necrotizing vasculitis, neonatal lupus erythematosus (NLE) syndrome, nephrotic syndrome, pemphigoid, pemphigus, polymyositis, primary sclerosing cholangitis, psoriasis, rapidly-progressive glomerulonephritis (RPGN), Reiter's syndrome, stiff-man syndrome, thyroiditis, inflammatory bowel disease, skin disorders (e.g., atopic dermatitis, psoriasis, pemphigus vulgaris), cardiovascular problems (e.g., autoimmune pericarditis) and any combination thereof. In one embodiment, the at least one apolipoprotein fragment further comprises a modification selected from the group consisting of halogenation, hydroxylation, oxidation, peroxidation, dimerization, sulfoxidation and nitration. In one embodiment, said sulfoxidation comprises one or two sulfoxidized methionine residues and not a modified tyrosine residue. In one embodiment, the at least one apolipoprotein fragment is selected from the group consisting of an apolipoprotein A-I, an apolipoprotein A-II and an apolipoprotein A-IV. In one embodiment, the at least one apolipoprotein fragment is selected from the group consisting of an apolipoprotein C-I, an apolipoprotein C-II and an apolipoprotein C-III. In one embodiment, the at least one apolipoprotein fragment is an apolipoprotein E. In one embodiment, the nanoparticle further comprises a targeting agent selected from the group consisting of an apo E-derived lipopeptide, an apo A-I mimetic peptide, a murine MDA2 antibody, a murine E06 antibody, a human IK17 antibody and a gold particle. In one embodiment, the at least one apolipoprotein fragment is an amphipathic apolipoprotein fragment. In one embodiment, the therapeutic agent is incorporated within the nanoparticle. In one embodiment, the therapeutic agent is encapsulated within the nanoparticle. In one embodiment, the therapeutic agent is conjugated to the nanoparticle. In one embodiment, the therapeutic agent is attached to the nanoparticle. In one embodiment, the therapeutic agent is selected from the group consisting of anticancer agents, antibacterial agents, antiviral agents, autoimmune agents, anti-inflammatory agents, cardiovascular agents, antioxidant agents, and therapeutic peptide agents. In one embodiment, the therapeutic agent is selected from the group consisting of paclitaxel, valrubicin, doxorubicin, taxotere, campotechin, and etoposide. In one embodiment, the plurality of phospholipids further comprise at least one lipid that is selected from the group consisting of a cholesterol, a cholesteryl ester, a glycolipid, a sphingolipid, a cationic lipid, a diacylglycerol, and a triacylglycerol. In one embodiment, the plurality of phospholipids are selected from the group consisting of phosphatidylcholine (PC), phosphatidylethanolamine (PE), phosphatidylserine (PS), phosphatidylinositol (PI), phosphatidylglycerol (PG), cardiolipin (CL), sphingomyelin (SM), and phosphatidic acid (PA). In one embodiment, the cationic lipid is 1,2-dioleoyl-3-trimethylammonium-propane (DOTAP). In one embodiment, the plurality of phospholipids further comprises polyethylene glycol(PEG)ylated. In one embodiment, the nanoparticle has a diameter of less than about 100 nm. In one embodiment, the composition is a pharmaceutical composition comprising a pharmaceutically acceptable carrier. In one embodiment, the nanoparticle has a diameter ranging between approximately 5-25 nanometers. In one embodiment, the plurality of phospholipids further comprise a chelating agent. In one embodiment, at least one of said plurality of phospholipids is modified. In one embodiment, the modified apolipoprotein fragment comprises a secondary structure that is unchanged as compared to an unmodified apolipoprotein. In one embodiment, the nanoparticle is discoidal.

In one embodiment, the present invention contemplates a method, comprising: a) providing; i) a patient exhibiting at least one symptom of a disease or disorder; and ii) a pharmaceutically acceptable composition comprising a reconstituted lipoprotein nanoparticle comprising: A) a triglyceride-cholesterol ester core surrounded by a plurality of phospholipids; B) at least one apolipoprotein fragment; and C) at least one therapeutic agent; and b) administering said pharmaceutically acceptable composition to the patient such that the at least one symptom of said disease or disorder is reduced. In one embodiment, the disease or disorder comprises a macrophage-related disease or disorder. In one embodiment, the macrophage-related disease or disorder includes, but is not limited to, a heart disease, peripheral artery disease, restenosis, stroke, the cancers (e.g., sarcoma, lymphoma, leukemia, carcinoma and melanoma), bacterial infectious diseases, acquired immune deficiency syndrome (AIDS), allergic diseases, autoimmune diseases (e.g., rheumatoid arthritis, Sjogrens, scleroderma, systemic lupus erythematosus, non-specific vasculitis, Kawasaki's disease, psoriasis, type I diabetes, pemphigus vulgaris), granulomatous diseases (e.g., tuberculosis, sarcoidosis, lymphomatoid granulomatosis, Wegener's granulomatosus), Gaucher's disease, inflammatory diseases (e.g., sepsis, inflammatory lung diseases such as interstitial pneumonitis and asthma, inflammatory bowel disease such as Crohn's disease, and inflammatory arthritis), and transplant (e.g., heart/lung transplants) rejection reactions. In one embodiment, the disease or disorder comprises an autoimmune disease. In one embodiment, the autoimmune disease included, but is not limited to, diabetes mellitus, rheumatoid arthritis, multiple sclerosis, systemic lupus erythematosis, myasthenia gravis, scleroderma, Crohn's disease, ulcerative colitis, biliary cirrhosis, chronic active hepatitis, Hashimoto's thyroiditis, Graves' disease, Sjogren's syndrome, polyendocrine failure, vitiligo, peripheral neuropathy, rejection of transplantation, graftversus-host disease, autoimmune polyglandular syndrome type I, acute glomerulonephritis, Addison's disease, adult-onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barre syndrome, hemochromatosis, Henoch-Schonlein purpura, idiopathic IgA nephropathy, juvenile rheumatoid arthritis, Lambert-Eaton syndrome, linear IgA dermatosis, myocarditis, narcolepsy, necrotizing vasculitis, neonatal lupus erythematosus (NLE) syndrome, nephrotic syndrome, pemphigoid, pemphigus, polymyositis, primary sclerosing cholangitis, psoriasis, rapidly-progressive glomerulonephritis (RPGN), Reiter's syndrome, stiff-man syndrome, thyroiditis, inflammatory bowel disease, skin disorders (e.g., atopic dermatitis, psoriasis, pemphigus vulgaris), cardiovascular problems (e.g., autoimmune pericarditis) and any combination thereof. In one embodiment, the at least one apolipoprotein fragment further comprises a modification selected from the group consisting of halogenation, hydroxylation, oxidation, peroxidation, dimerization, sulfoxidation and nitration. In one embodiment, the sulfoxidation comprises one or two sulfoxidized methionine residues and not a modified tyrosine residue In one embodiment, the at least one apolipoprotein fragment is selected from the group consisting of an apolipoprotein A-I, an apolipoprotein A-II and an apolipoprotein A-IV. In one embodiment, the at least one apolipoprotein fragment is selected from the group consisting of an apolipoprotein C-I, an apolipoprotein C-II and an apolipoprotein C-III. In one embodiment, the at least one apolipoprotein fragment is apolipoprotein E. In one embodiment, the nanoparticle further comprises a targeting agent selected from the group consisting of an apo E-derived lipopeptide, an apo A-I mimetic peptide, a murine MDA2 antibody, a murine E06 antibody, a human IK17 antibody and a gold particle. In one embodiment, at least one said apolipoprotein fragments is an amphipathic apolipoprotein. In one embodiment, the therapeutic agent is incorporated within the nanoparticle. In one embodiment, the therapeutic agent is encapsulated within the nanoparticle. In one embodiment, the therapeutic agent is conjugated to the nanoparticle. In one embodiment, the therapeutic agent is attached to the nanoparticle. In one embodiment, the therapeutic agent is selected from the group consisting of anticancer agents, antibacterial agents, antiviral agents, autoimmune agents, anti-inflammatory agents, cardiovascular agents, antioxidant agents, and therapeutic peptide agents. In one embodiment, the therapeutic agent is selected from the group consisting of paclitaxel, valrubicin, doxorubicin, taxotere, campotechin, and etoposide. In one embodiment, the plurality of phospholipids further comprise at least one lipid that is selected from the group consisting of a cholesterol, a cholesteryl ester, a glycolipid, a sphingolipid, a cationic lipid, a diacylglycerol, and a triacylglycerol. In one embodiment, the plurality of phospholipids are selected from the group consisting of phosphatidylcholine (PC), phosphatidylethanolamine (PE), phosphatidylserine (PS), phosphatidylinositol (PI), phosphatidylglycerol (PG), cardiolipin (CL), sphingomyelin (SM), and phosphatidic acid (PA). In one embodiment, the cationic lipid is 1,2-dioleoyl-3-trimethylammonium-propane (DOTAP). In one embodiment, the plurality of phospholipids further comprise polyethylene glycol(PEG)ylated. In one embodiment, the nanoparticle has a diameter of less than about 100 nm. In one embodiment, the nanoparticle is a pharmaceutical composition comprising a pharmaceutically acceptable carrier. In one embodiment, the nanoparticle has a diameter ranging between approximately 5-25 nanometers. In one embodiment, the plurality of phospholipids further comprise a chelating agent. In one embodiment, at least one of said plurality of phospholipids is modified. In one embodiment the modified apolipoprotein fragment comprises a secondary structure that is unchanged as compared to an unmodified apolipoprotein. In one embodiment, the nanoparticle is spherical.

Definitions

The terms "APOA1_HUMAN", "Apolipoprotein A-I", "Apolipoprotein A-1", "APOA1", "ApoA-I", "Apo-AI", "ApoA-1", "apo-A1", "apoA-1" and "Apo-A1" refer to the naturally occurring human protein listed in the UniProt Knowledgebase (UniProtKB, www.uniprot.org) under the name "APOA1_HUMAN". The protein amino acid sequence can be found under the entry UniProt KB/Swiss-Prot P02647 (uniprot.org/uniprot/P02647). The terms "APOA2_HUMAN", "Apolipoprotein A-II", Apolipoprotein "APOA2", "ApoA-II", "Apo-AII", "ApoA-2", "apo-A2", "apoA-2" and "Apo-A2" refer to the naturally occurring human protein listed in the UniProt Knowledgebase (UniProtKB, uniprot.org) under the name "APOA2_HUMAN". The protein amino acid sequence can be found under the entry UniProt KB/Swiss-Prot P02652 (uniprot.org/uniprot/P02652). These peptides are generally considered to be full length peptides.

The terms "APOC1_HUMAN", 'Apolipoprotein C-1", 'Apolipoprotein C-1", "APOC1", "ApoC-I", "Apo-CI", "ApoC-1", "apo-C1", "apoC-1" and "Apo-C1" refer to the naturally occurring human protein listed in the UniProt Knowledgebase (UniProtKB, uniprot.org) under the name "APOC1_HUMAN". The protein amino acid sequence can be found under the entry UniProt KB/Swiss-Prot P02654 (uniprot.org/uniprot/P02654). The terms "APOC2_HUMAN", 'Apolipoprotein C-2", 'Apolipoprotein C-2", "APOC2", "ApoC-II", "Apo-CII", "ApoC-2", "apo-C2", "apoC-2" and "Apo-C2" refer to the naturally occurring human protein listed in the UniProt Knowledgebase (UniProtKB, uniprot.org) under the name "APOC2_HUMAN". The protein amino acid sequence can be found under the entry UniProt KB/Swiss-Prot P02655 (uniprot.org/uniprot/P02655). The terms "APOC3_HUMAN", 'Apolipoprotein C-3", 'Apolipoprotein C-3", "APOC3", "ApoC-III", "Apo-CIII", "ApoC-3", "apo-C3", "apoC-3" and "Apo-C3" refer to the naturally occurring human protein listed in the UniProt Knowledgebase (UniProtKB, uniprot.org) under the name "APOC3_HUMAN". The protein amino acid sequence can be found under the entry UniProt KB/Swiss-Prot P02656 (uniprot.org/uniprot/P02656). These peptides are generally considered to be full length peptides.

The term "recombinant protein", as used herein describes a protein obtained from bacterial or other sources using the recombinant DNA technology. Furthermore, a suffix or a prefix indicating the species from which the protein is derived is added to the protein's name when a non-human protein such as non-human apo A-I or apo A-II is described (U.S. Pat. No. 6,953,840; uniprot.org/uniprot/Q00623; uniprotorg/uniprot/P09813). In special cases, a suffix or a prefix may also indicate a well-known apoA-1 variant, e.g. apo A-I Milano (U.S. Pat. No. 7,435,717).

As used herein, the term "aptamer" or "specifically binding oligonucleotide" refers to an oligonucleotide that is capable of forming a complex with an intended target substance.

The term "modified protein" as used herein describes a protein subjected to a chemical or enzyme, or chemically and enzymatically modified oligopeptides, oligopseudopeptides, polypeptides, pseudopolypeptides, and native proteins (synthetic or otherwise derived), regardless of the nature of the chemical and/or enzymatic modification. For example, a modified protein can be an oxidized protein. "Modified proteins" have utility in many biomedical applications because of their increased stability against in vivo degradation, superior pharmacokinetics, and altered immunogenicity compared to their native counterparts.

The term "pseudopeptide" refers to a peptide where one or more peptide bonds are replaced by non-amido bonds such as ester or one or more amino acids are replaced by amino acid analogs.

The term "peptides" refers not only to those comprised of all natural amino acids, but also to those which contain unnatural amino acids or other non-coded structural units. The terms "peptides", when used alone, include pseudopeptides.

The term "full length" peptide refers to a peptide having the number of amino acid residues encoded by a wild type gene.

The term "peptide fragment" refers a peptide that is at least one amino acid residue shorter in length in comparison to that encoded by a wild type gene.

The term "oxidized protein" refers to a protein in which at least one amino acid residue is oxidized.

The term "oxidized protein fragment" refers to a protein fragment in which at least one amino acid residue is oxidized.

The term "oxidation status" refers to a metric of the extent to which specific amino acid residues are replaced by corresponding oxidized amino acid residues in a protein or a protein fragment.

The term "extent of oxidation" refers to the degree to which potentially oxidizable amino acids in a protein or fragment have undergone oxidation. For example, if the protein fragment contains a single tyrosine residue which is potentially oxidized to 3-chlorotyrosine, then an increase in mass of about 34 Dalton (i.e., the approximate difference in mass between chlorine and hydrogen) indicates oxidation of tyrosine to 3-chlorotyrosine. Similarly, if the protein fragment contains a single methionine residue which is potentially oxidized to methionine sulfoxide, then an increase in mass of 16 Dalton (i.e., the difference in mass between methionine and methionine containing one extra oxygen) indicates oxidation of methionine to methionine sulfoxides. The oxidation status can be measured by metrics known to the arts of protein and peptide chemistry (US Pat Appl 20080020400; US Pat Appl 20050239136) including, without limitation, assay of the number of oxidized residues, mass spectral peak intensity, mass spectral integrated area, and the like. In some embodiments of any of the aspects provided herein, oxidation status is reported as a percentage, wherein 0% refers to no oxidation and 100% refers to complete oxidation of potentially oxidizable amino acid residues within apo A-I or apo A-II or fragments thereof.

The term "potentially subject to oxidation," "potentially oxidizable amino acid residues", and the like refer to an amino acid which can undergo oxidation, for example by nitration or chlorination.

The term "encapsulation" as used herein refers to the enclosure of a molecule, such as a contrast agent or therapeutics, inside the nanoparticle. Such encapsulation may be generated, according to an embodiment, by synthesis of nanoparticles in the presence of a liquid solution containing a contrast agent or therapeutics.

The term "incorporation" as used herein refers to imbibing or adsorbing the contrast agent or therapeutics onto the nanoparticle.

The terms "reconstituted" and "recombinant" as used herein both refer to synthetic HDL-type particles that represent both discoidal and spherical nanoparticles.

A "site of interest" on a target as used herein is a site to which modified proteins and protein fragments of the present invention bind.

The term "target site", as used herein, refers to sites/tissue areas of interest. As used in this invention, The terms "target cells" or "target tissues" refer to those cells or tissues, respectively that are intended to be targeted using the compositions of the present invention delivered in accord with the invention. Target cells or target tissues take up or link with the modified proteins or protein fragments of the invention. Target cells are cells in target tissue, and the target tissue includes, but is not limited to, atherosclerotic plaques, vascular endothelial tissue, abnormal vascular walls of tumors, solid tumors, tumor-associated macrophages, and other tissues or cells related to cancer, cardiovascular, inflammatory, autoimmune diseases, and the like. Further, target cells include virus-containing cells, and parasite-containing cells. Also included among target cells are cells undergoing substantially more rapid division as compared to non-target cells. The term "target cells" also includes, but is not limited to, microorganisms such as bacteria, viruses, fungi, parasites, and infectious agents. Thus, the term "target cell" is not limited to living cells but also includes infectious organic particles such as viruses. "Target compositions" or "target biological components" include, but are not be limited to: toxins, peptides, polymers, and other compounds that may be selectively and specifically identified as an organic target that is intended to be visualized in imaging techniques using the compositions of the present invention.

The terms "macrophage-associated", "macrophage-mediated", and "macrophage-related diseases" include diseases associated with macrophages (U.S. Pat. No. 7,740,854 and PCT Pat Appl PCT/US10/52117). The term "plaque" includes, for example, an atherosclerotic plaque.

The term, "amino acid domain", as used herein refers to is a contiguous polymer of at least two (2) amino acids joined by peptide bond(s). The domain may be joined to another amino acid or amino acid domain by one or more peptide bonds. An amino acid domain can constitute at least two amino acids at the N-terminus or C-terminus of a peptide or can constitute at least two amino acids in the middle of a peptide.

A "biologically active peptide motif" is a peptide that induces a phenotypic response or change in an appropriate cell type when the cell is contacted with the peptide. The peptide may be present either in isolated form or as part of a larger polypeptide or other molecule. The ability of the peptide to elicit the response may be determined, for example, by comparing the relevant parameter in the absence of the peptide (e.g., by mutating or removing the peptide when normally present within a larger polypeptide). Phenotypic responses or changes include, but are not limited to, enhancement of cell spreading, attachment, adhesion, proliferation, secretion of an extracellular matrix (ECM)

molecule, or expression of a phenotype characteristic of a particular differentiated cell type.

As used herein, "naturally occurring" means found in nature. A naturally occurring biomolecule is, in general, synthesized by an organism that is found in nature and is unmodified by the hand of man, or is a degradation product of such a molecule. A molecule that is synthesized by a process that involves the hand of man (e.g., through chemical synthesis not involving a living organism or through a process that involves a living organism that has been manipulated by the hand of man or is descended from such an organism) but that is identical to a molecule that is synthesized by an organism that is found in nature and is unmodified by the hand of man is also considered a naturally occurring molecule.

The term, "subject" or "patient", as used herein, refers to any individual organism. For example, the organism may be a mammal such as a primate (i.e., for example, a human). Further, the organism may be a domesticated animal (i.e., for example, cats, dogs, etc.), livestock (i.e., for example, cattle, horses, pigs, sheep, goats, etc.), or a laboratory animal (i.e., for example, mouse, rabbit, rat, guinea pig, etc.).

The term "sample," as used herein, refers to a composition that is obtained or derived from a subject that contains a cellular and/or other molecular entity that is to be characterized, quantitated, and/or identified, for example based on physical, biochemical, chemical and/or physiological characteristics.

The term, "therapeutically effective amount", "therapeutically effective dose" or "effective amount", as used herein, refers to an amount needed to achieve a desired clinical result or results (e.g. inhibiting receptor-mediated cell activation) based upon trained medical observation and/or quantitative test results. The potency of any administered peptide or compound determines the "effective amount" which can vary for the various compositions that inhibit myeloid cell activation (i.e., for example, compositions inhibiting TREM ligand-induced myeloid cell activation). Additionally, the "effective amount" of a compound may vary depending on the desired result, for example, the level of myeloid cell activation inhibition desired. The "therapeutically effective amount" necessary for inhibiting differentiation of primary monocytes into immature dendritic cells may differ from the "therapeutically effective amount" necessary for preventing or inhibiting cytokine production.

The term, "agent", as used herein, refers to any natural or synthetic compound (i.e., for example, a peptide, a peptide variant, or a small molecule).

The term, "composition", as used herein, refers to any mixture of substances comprising a peptide and/or compound contemplated by the present invention. Such a composition may include the substances individually or in any combination.

The term "therapeutic agent" or "drug", as used herein, refers to any compound or composition having preventive, therapeutic or diagnostic activity, primarily but not exclusively in the treatment of patients with myeloid cell-related diseases. Also any pharmacologically active substance capable of being administered which achieves a desired effect. Drugs or compositions can be synthetic or naturally occurring, non-peptide, proteins or peptides, oligonucleotides or nucleotides, polysaccharides or sugars. Drugs or compositions may have any of a variety of activities, which may be stimulatory or inhibitory, such as antibiotic activity, antiviral activity, antifungal activity, steroidal activity, cytotoxic, cytostatic, anti-proliferative, anti-inflammatory, analgesic or anesthetic activity, or can be useful as contrast or other diagnostic agents.

The term "effective dose" as used herein refers to the concentration of any compound or drug contemplated herein that results in a favorable clinical response. In solution, an effective dose may range between approximately 1 ng/ml and 100 mg/ml, preferably between 100 ng/ml and 10 mg/ml, but more preferably between 500 ng/ml and 1 mg/ml.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

A "pharmaceutically acceptable carrier" or "pharmaceutically acceptable composition" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

BRIEF DESCRIPTION OF THE FIGURES

The following figures form part of the present specification and are included to further illustrate aspects of the present invention. The invention may be better understood by reference to the figures in combination with the detailed description of the specific embodiments presented herein.

FIG. 14(A): Mean fluorescence intensities of cell lysates normalized to cell protein content (mean±SD, n=3): J774 macrophages were incubated at 37° C. for 4 h with medium only (white bars) or with 4 μM Rho-B fluorescent GF9-HDL(A-I) or GF9-HDL(PE22:PA22; 1:1 molar ratio) of discoidal or spherical morphology. Unmodified and oxidized apo A-I protein and apo A-I synthetic fragments PE22 and PA22 are depicted by light and dark gray bars, respectively. ***, P=0.0001 to 0.001 as compared with unmodified apo A-I protein/peptides.

FIG. 14(B): Mean fluorescence intensities of cell lysates normalized to cell protein content (mean±SD, n=3): J774 macrophages were incubated at 37° C. for 4, 12 and 24 h (white, light gray and dark gray bars, respectively) with 4 μM Rho-B fluorescent GF9-HDL(A-Iox) or GF9-HDL (PE22ox:PA22ox; 1:1 molar ratio) of discoidal or spherical morphology that contain oxidized apo A-I or oxidized apo A-I synthetic fragments PE22 and PA22. ***, P=0.0001 to 0.001 as compared with 4 h time point. Abbreviations: apo, apolipoprotein; HDL, high density lipoproteins; HDL(A-I), HDL with apo A-I protein; HDL(PE22+PA22), HDL with a 1:1 mixture of synthetic peptides PE22 and PA22 that correspond to apo A-I helixes 4 and 6, respectively (SEE FIG. 1); dHDL and sHDL, discoidal and spherical HDL, respectively; LPC, lipoprotein/lipopeptide complexes; Rho-B, rhodamine B; SLP, synthetic lipoprotein/lipopeptide particles; TREM-1, triggering receptor expressed on myeloid cells-1.

FIG. 15(A): TREM-1 inhibitory peptide GF9 was incorporated into synthetic (recombinant) macrophage-targeted HDL that contain oxidized human apo A-I protein (A-Iox) and inhibits tumor growth in the A549 xenograft mouse model of NSCLC.

FIG. 15(B): TREM-1 inhibitory peptide GF9 was incorporated into macrophage-targeted HDL that contain an equimolar mixture of oxidized apo A-I synthetic fragments PE22 and PA22 (PE22ox and PA22ox, respectively) and inhibits tumor growth in the A549 xenograft mouse model of NSCLC.

Figure 12:
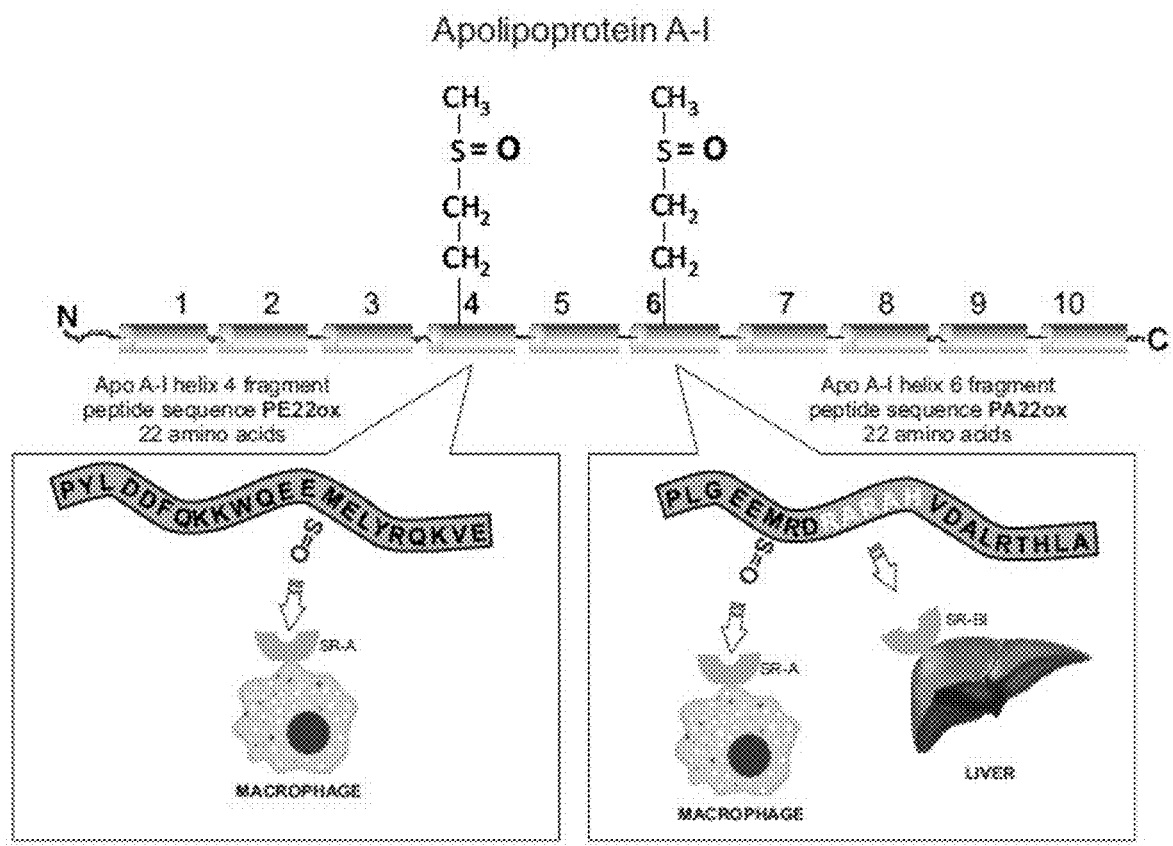
FIG. 12 presents a schematic representation of one embodiment of a human apolipoprotein (apo) A-I protein comprising ten (10) amphipathic α-helical repeats (helixes) with methionine sulfoxide residues in helixes 4 and 6.
Figure 16:
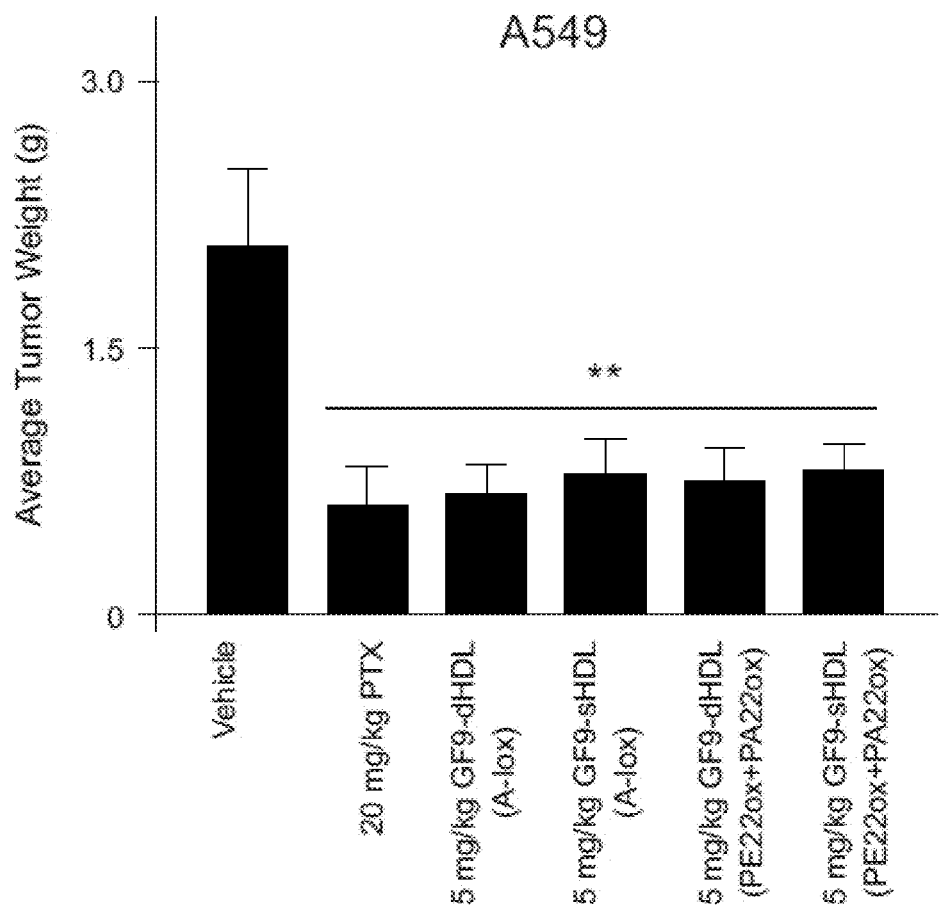

FIG. 16 presents exemplary data showing that in drug-containing synthetic (recombinant) HDL (SLP, LPC), apolipoprotein can be replaced by synthetic apolipoprotein fragments without compromising the drug antitumor activity in an animal model. Bars, SEM. For statistical analysis, each treatment was compared with the vehicle control using Student's t test. **, P 0.001 to 0.01. Abbreviations: apo, apolipoprotein; HDL, high density lipoproteins; HDL (A-Iox), HDL with oxidized human apo A-I; HDL (PE22ox+PA22ox), HDL with a 1:1 mixture of synthetic peptides PE22ox and PA22ox that correspond to apo A-I helixes 4 and 6, respectively (SEE FIG. 12); dHDL and sHDL, discoidal and spherical HDL, respectively; LPC, lipoprotein/lipopeptide complexes; NSCLC, non-small cell lung cancer; PTX, paclitaxel; SLP, synthetic lipoprotein/lipopeptide particles; TREM-1, triggering receptor expressed on myeloid cells-1.

Figure 17:
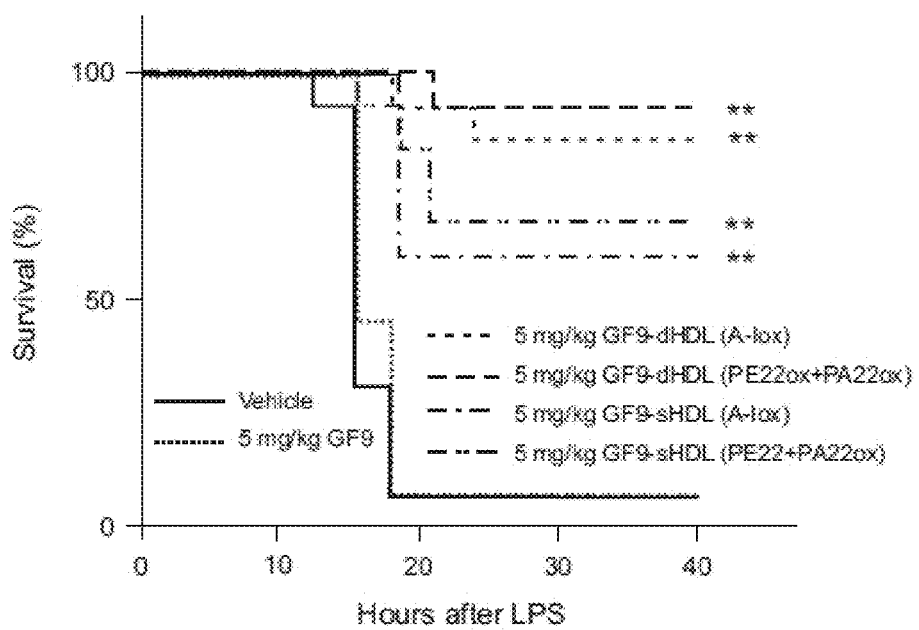
Figure 17:
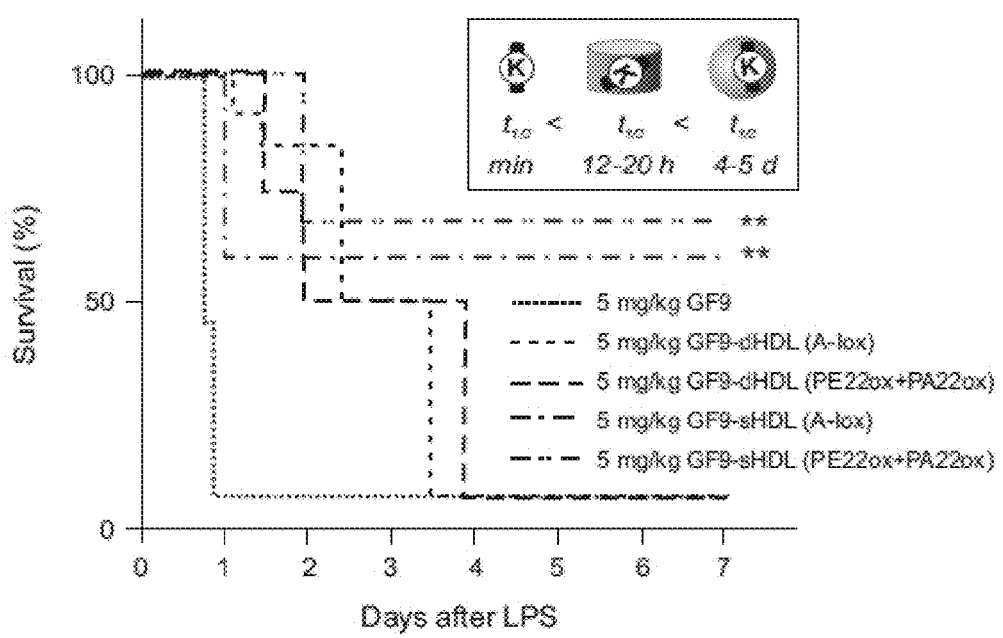

FIG. 17 presents exemplary data showing that, in drug-containing synthetic (recombinant) HDL (e.g, SLP, LPC), full length apolipoprotein can be replaced by synthetic apolipoprotein fragments without compromising the drug activity in an animal model of sepsis. C57BL/6 mice (n=10) were intraperitoneally administered with vehicle (HDL containing no GF9) or the indicated doses of GF9-dHDL (A-Iox), GF9-dHDL (A-Iox), GF9-sHDL (A-Iox) and GF9-sHDL (PE22ox+PA22ox) 1 h before LPS administration (30 mg/kg).

FIG. 17(A): Survival curve over 40-h after LPS injection.

FIG. 17 (B) Survival curve over seven (7) days after LPS injection. Inset: Expected apparent half-lives of agents in circulation.

The Kaplan-Meier survival curves were analyzed using the log-rank test. **, P=0.001 to 0.01 as compared with vehicle-treated animals. Abbreviations: apo, apolipoprotein; HDL, high density lipoproteins; dHDL and sHDL, discoidal and spherical HDL, respectively; LPC, lipoprotein/lipopeptide complexes; LPS, lipopolysaccharide; SLP, synthetic lipoprotein/lipopeptide particles; TREM-1, triggering receptor expressed on myeloid cells-1.

Figure 18:
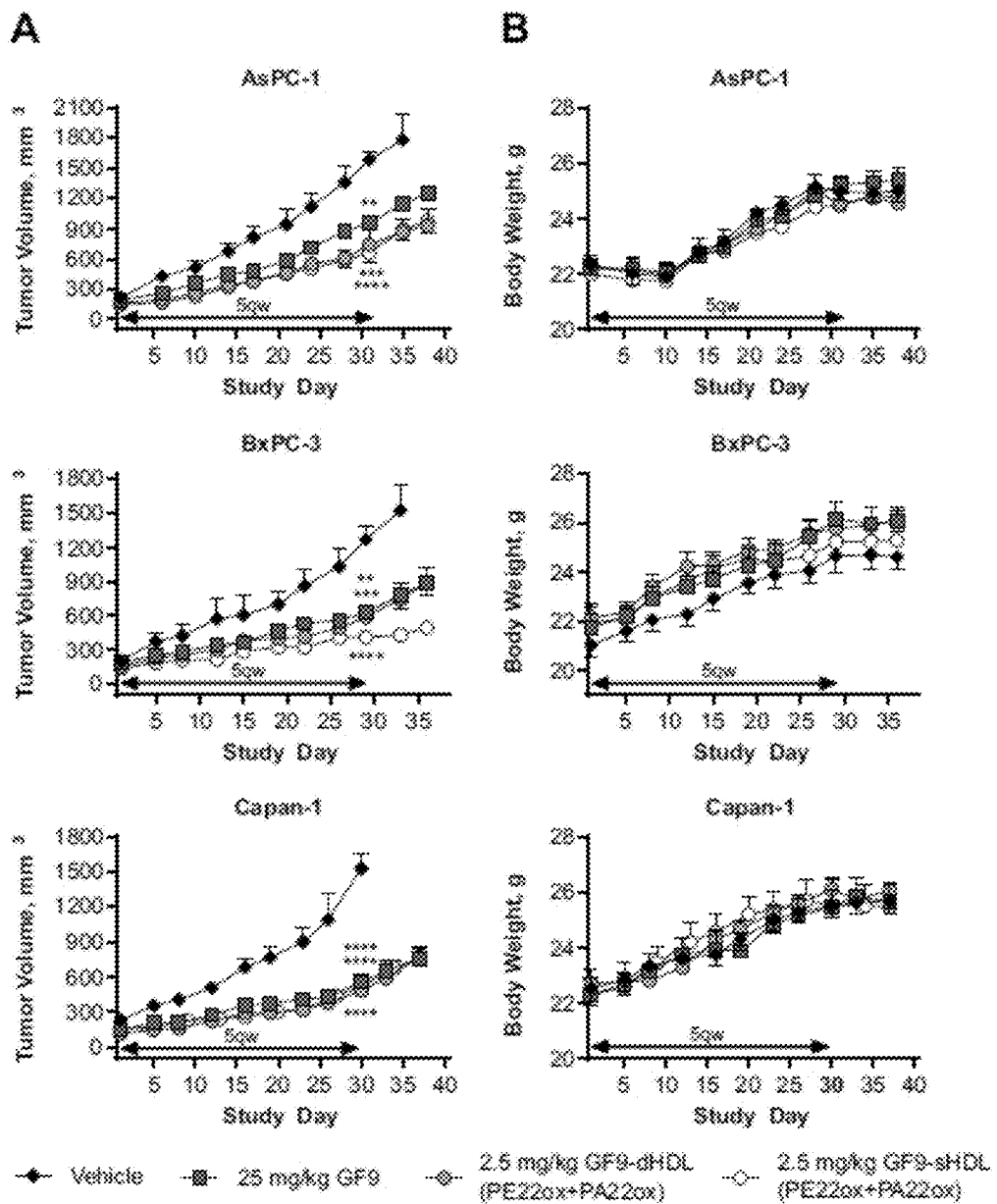

FIG. 18 presents exemplary data showing that drug-containing synthetic (recombinant) HDL (SLP, LPC) with synthetic apolipoprotein fragments exhibit drug antitumor activity in animal models of pancreatic cancer and are well-tolerated.

FIG. 18(A): Mean tumor volumes.

FIG. 18(B): Body weights.

Vehicle—(black diamonds); Free GF9 (dark gray squares); GF9-dHDL (PE22ox+PA22ox) (light gray circles); and GF9-sHDL (PE22ox+PA22ox) (white circles) at indicated doses. Treatment persisted for 31, 29, and 29 days for mice containing AsPC-1, BxPC-3, and Capan-1 tumor xenografts, respectively.

All results are expressed as the mean±SEM (n=6 mice per group). On the final day of treatment, tumor volumes and body weights were compared between the drug-treated and control groups. , p<0.01; *, p<0.001; ****, p<0.0001 (versus vehicle). Abbreviations: apo, apolipoprotein; HDL, high density lipoproteins; dHDL and sHDL, discoidal and spherical HDL, respectively; LPC, lipoprotein/lipopeptide complexes; SLP, synthetic lipoprotein/lipopeptide particles; TREM-1, triggering receptor expressed on myeloid cells-1.

Figure 19:
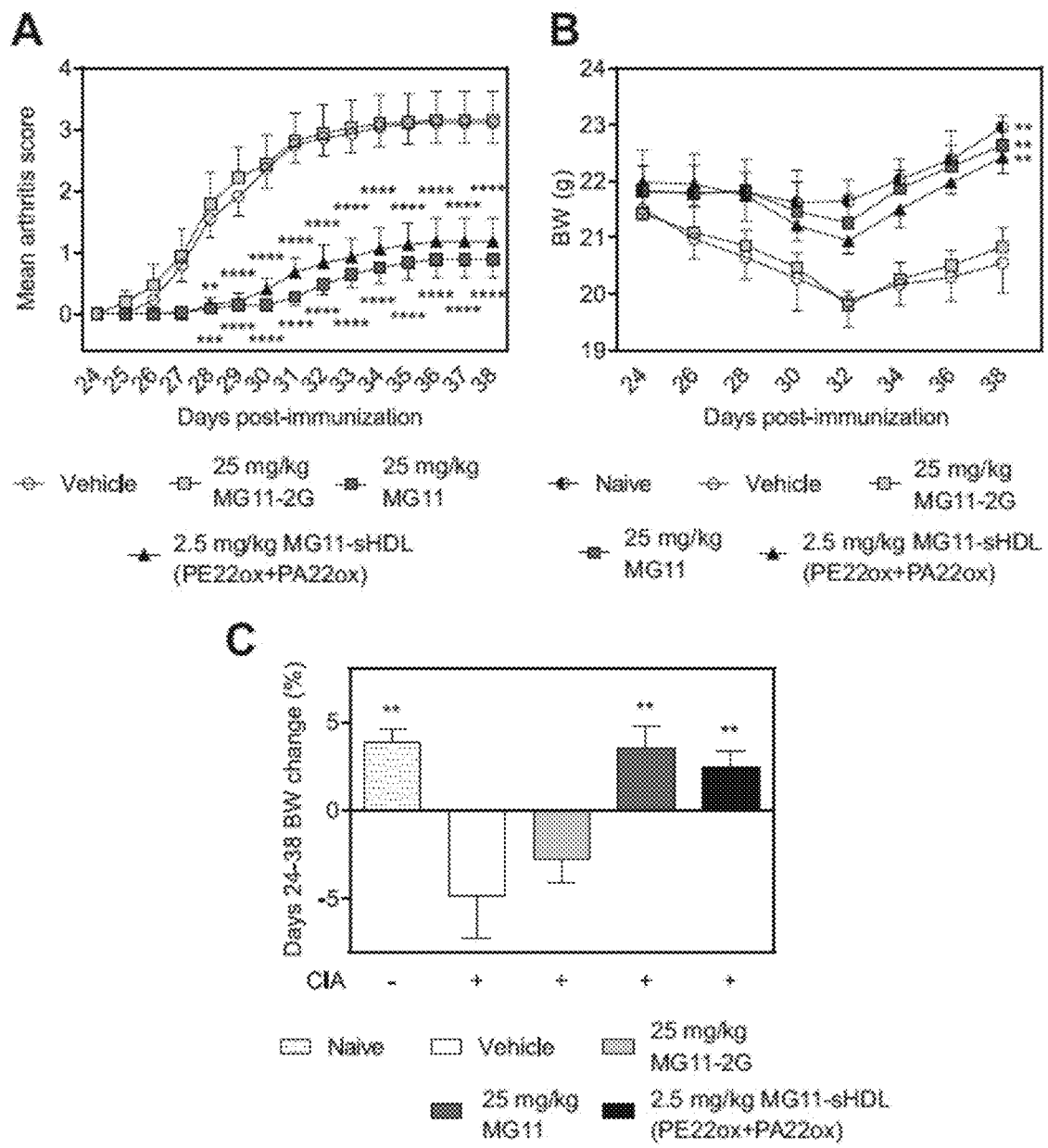

FIG. 19 presents exemplary data showing that drug-containing synthetic (recombinant) sHDL (SLP, LPC) with synthetic apolipoprotein fragments exhibit a drug antiarthritic activity in an animal model of rheumatoid arthritis and are well-tolerated.

FIG. 19(A): On day 24 post immunization, different groups of mice with CIA were intraperitoneally (i.p.) administered daily with either vehicle, control peptide MG11-2G (25 mg/kg), MG11 (25 mg/kg) or sHDL(PE22ox+PA22ox)-bound MG11 (2.5 mg/kg) for 14 days. Development of arthritis was monitored daily and clinical arthritis was scored.

FIG. 19(B): Mouse BW was measured every other day from day 24 to day 38. (C) Percentage in BW change at day 38 compared with day 24. All results are expressed as the mean±SEM (n=10 mice per group). , P<0.01; *, P<0.005; and ****, P<0.001 versus vehicle. Abbreviations: apo, apolipoprotein; BW, body weight; CIA, collagen-induced arthritis; HDL, high density lipoproteins; sHDL, spherical HDL; LPC, lipoprotein/lipopeptide complexes; SARS-CoV-1, severe acute respiratory syndrome coronavirus 1; SLP, synthetic lipoprotein/lipopeptide particles; TCR, T cell receptor.

Figure 20:
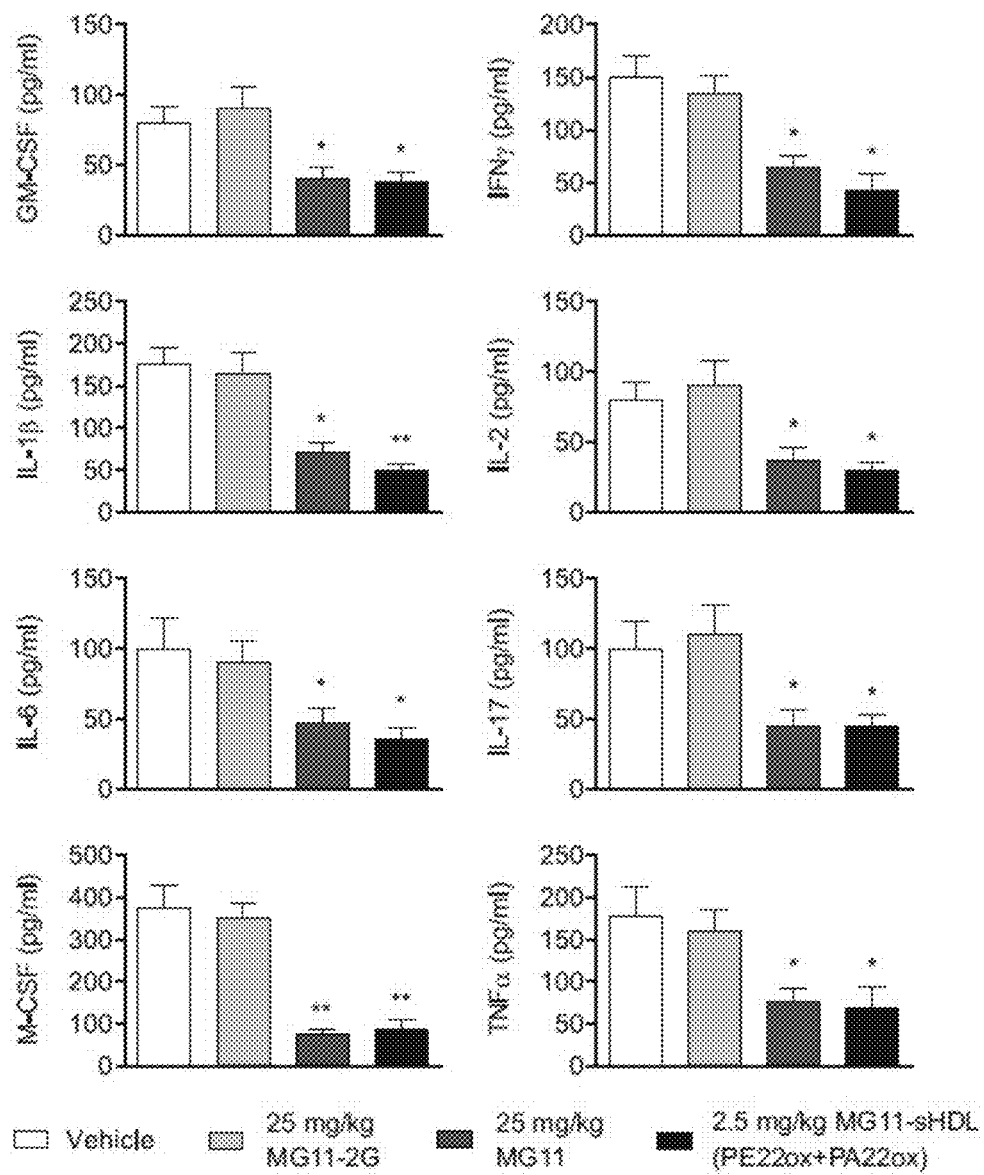

FIG. 20 presents exemplary data showing that drug-containing synthetic (recombinant) HDL (SLP, LPC) with synthetic apolipoprotein fragments exhibit the cytokine-reducing activity of the drug in an animal model of rheumatoid arthritis. Serum was collected at the end of treatment on day 38 from different groups of mice with CIA intraperitoneally (i.p.) administered daily with either vehicle, control peptide MG11-2G (25 mg/kg), MG11 (25 mg/kg) or sHDL(PE22ox+PA22ox)-bound MG11 (2.5 mg/kg). Serum samples were analyzed for concentrations of GM-CSF, IFNγ, IL-1β, IL-2, IL-6, IL-17, (M-CSF and TNFα. Results are expressed as the mean±SEM (n=5 mice per group). * P<0.05; ** P<0.01. Abbreviations: apo, apolipoprotein; BW, body weight; CIA, collagen-induced arthritis; HDL, high density lipoproteins; sHDL, spherical HDL; LPC, lipoprotein/lipopeptide complexes; SARS-CoV-1, severe acute respiratory syndrome coronavirus 1; SLP, synthetic lipoprotein/lipopeptide particles; TCR, T cell receptor; GM-CSF, granulocyte-macrophage colony-stimulating factor; IFNγ, interferon-γ; IL-1β, interleukin-1β; M-CSF, macrophage colony-stimulating factor; TNFα, tumor necrosis factor-α.

DETAILED DESCRIPTION OF THE INVENTION

The present invention is related to the field of targeted drug delivery. In particular, the particles and compositions described herein are used to deliver drugs to treat the diseases and conditions of interest. These particles and compositions include, but are not limited to, a lipopeptide complex (e.g., a high-density lipoprotein) and contain an apolipoprotein fragment or combinations thereof.

Numerous formulation approaches have been developed, including solid lipid particles, emulsions, liposomes, etc., however, the delivery of the poorly water soluble (hydrophobic, or lipophilic) pharmaceuticals remains especially problematic as most of the body compartments, including the blood circulation and intracellular fluids, represent an aqueous environment. As a result, the direct injection of hydrophobic TAs often results in harmful side effects due to hypersensitivity, hemolysis, cardiac and neurological symptoms. Consequently, there is need for more effective formulations of hydrophobic drugs to improve their targeted delivery, biocompatibility and therapeutic efficiency.

Chemical or enzymatic modification of fully assembled HDL particles enhances their absorption by the macrophages. However, in the modified HDL particle both, the protein and the lipid portion of the particle can undergo the chemical modification. The prior art (U.S. Pat. Nos. 6,306,433, 7,824,709, and 6,514,523; US Pat Appls 20090110739 and 20070243136) neither suggests nor teaches one of ordinary skill in the art to investigate the drug delivery performance of HDL particles in which only the apolipoprotein portion has been chemically altered.

As described herein, it is surprisingly found that oxidative modification of only protein constituents or peptide fragments thereof of HDL is sufficient to convert these particles to substrates for macrophage scavenger receptors and provide targeted delivery, biocompatibility and therapeutic efficiency of TAs. Compositions of the invention are synthetic HDL or HDL-like particles, protein constituents of which, apolipoproteins (apo) A-I and/or A-II or fragments thereof are modified. Certain controlled chemical or enzymatic modification of apo A-I or A-II or fragments thereof converts these apolipoproteins to substrates for macrophage scavenger receptors and results in the improvement of association of the TA-(HDL/modified apolipoprotein)-particle with macrophages and/or absorption (uptake) of the TA-(HDL/modified apolipoprotein)-particle by macrophages when compared to that of the TA-(HDL/apolipoprotein)-particle constructed with non-modified naturally occurring apo A-I, apo A-II or fragments thereof. These advantageous compositions are demonstrated by the present invention to solve numerous problems which otherwise are associated with high dosages of TAs required and the lack of control and reproducibility of formulations, especially in large-scale production.

A. Apolipoproteins and Apolipoprotein Peptides

In one embodiment of the present invention, the lipoproteins of interest are HDLs and their synthetic reconstituted analogues. The functional characteristics of HDL particles are mainly determined by their major protein components such as full length or fragments of apolipoproteins (e.g., apo A-I and A-II). Each HDL particle usually comprises at least 1 molecule, and usually 2 to 4 molecules, of apo A-I.

Examples of suitable full length of fragments of apolipoproteins include, but are not limited to, preproapolipoprotein forms of apo A-I and apo A-II; pro- and mature forms of human apo A-I and apo A-II; and active polymorphic forms, isoforms, variants, mutants as well as truncated forms, the most common of which are apo A-I$_{Milano}$ and apo A-I$_P$, as disclosed in US Pat Appl 20060217312. Apolipoprotein mutants containing cysteine residues are also known, and can also be used (see, e.g., US Pat Appl 20030181372). The apolipoproteins may be in the form of monomers or dimers, which may be homodimers or heterodimers. For example, homo- and heterodimers (where feasible) of pro- and mature apo A-I, apoA-I$_{Milano}$, apoA-I$_P$, and apo A-II may be used. The apolipoproteins may include residues corresponding to elements that facilitate their isolation, such as His tags, or other elements designed for other purposes, so long as the apolipoprotein retains some biological activity when included in a complex.

As it is well-known in the art, such apolipoproteins can be purified from animal sources (and in particular from human sources) or produced recombinantly (PCT Pat Appl PCT/US10/52117, U.S. Pat. Nos. 5,059,528, 5,128,318, 6,617,134, and U.S. Pat Appls 20020156007, 20040067873, 20040077541, and 20040266660).

Non-limiting examples of peptides and peptide analogs that correspond to apo A-I, apo A-I$_{Milano}$, and apo A-II, and are suitable for enzymatic and/or chemical modifications and subsequent use as peptide fragments of modified apolipoproteins in the complexes and compositions described herein are disclosed in U.S. Pat. Nos. 6,004,925, 6,037,323 and 6,046,166, 5,840,688, US Appls 20040266671, 20040254120, 20030171277, 20030045460, 20030087819, and 20060217312. These peptides and peptide analogues can be composed of L-amino acid or D-amino acids or mixture of L- and D-amino acids. They may also include one or more non-peptide or amide linkages, such as one or more well-known peptide/amide isosteres. Such "peptide and/or peptide mimetic" apolipoproteins can be synthesized or manufactured using any technique for peptide synthesis known in the art, including, e.g., the techniques described in U.S. Pat. Nos. 6,004,925, 6,037,323 and 6,046,166.

The complexes and compositions of the present invention may include a single type of apolipoprotein and/or peptide fragments thereof, or mixtures of two different apolipoproteins and peptide fragments thereof, which may be derived from the same or different species. Although not required, the charged lipoprotein complexes will preferably comprise apolipoproteins that are derived from, or correspond in amino acid sequence to, the animal species being treated, in order to avoid inducing an immune response to the therapy. The use of peptide mimetic apolipoproteins may also reduce or avoid an immune response.

B. Modified Apolipoproteins and Apolipoprotein Peptides

Figure 1:
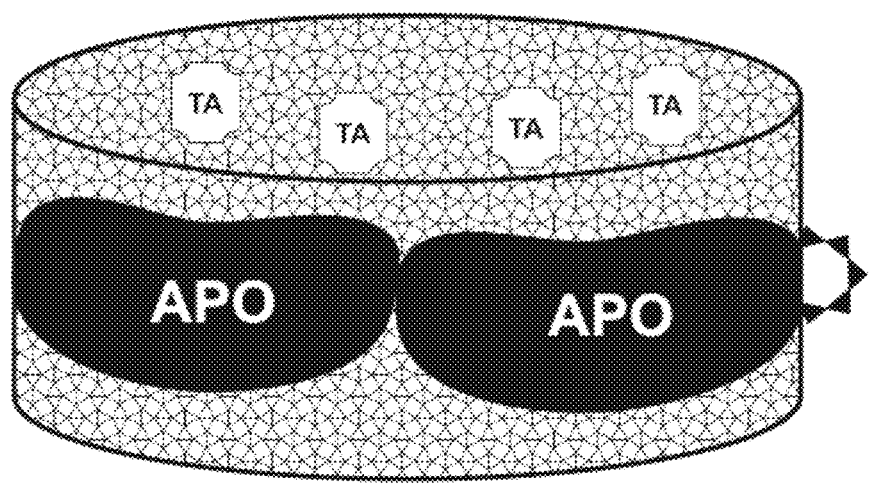
FIG. 1 presents a schematic representation of one embodiment of a discoidal composition of the present invention with a therapeutic agent attached to said composition.
Figure 2A:
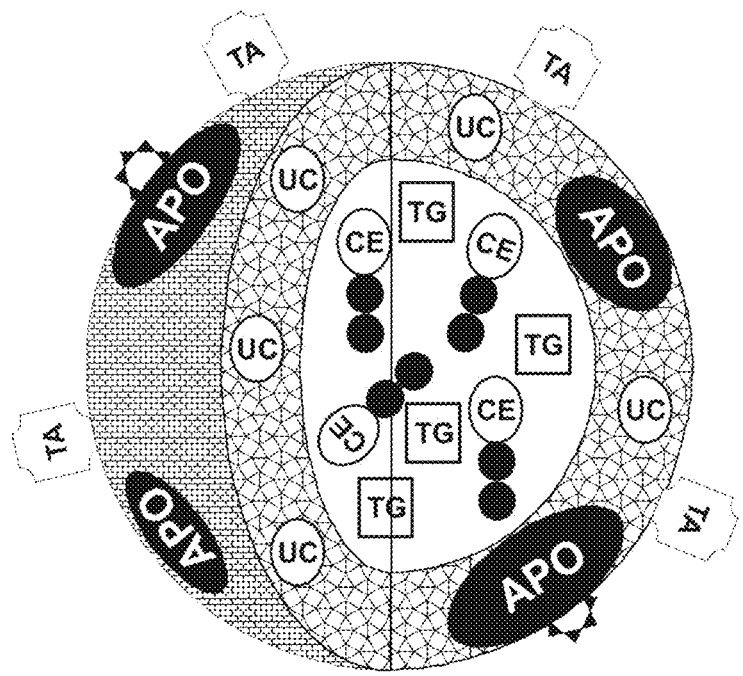
FIG. 2A presents a schematic representation of one embodiment of a spherical composition of the present invention with a therapeutic agent attached to said composition.
Figure 2B:
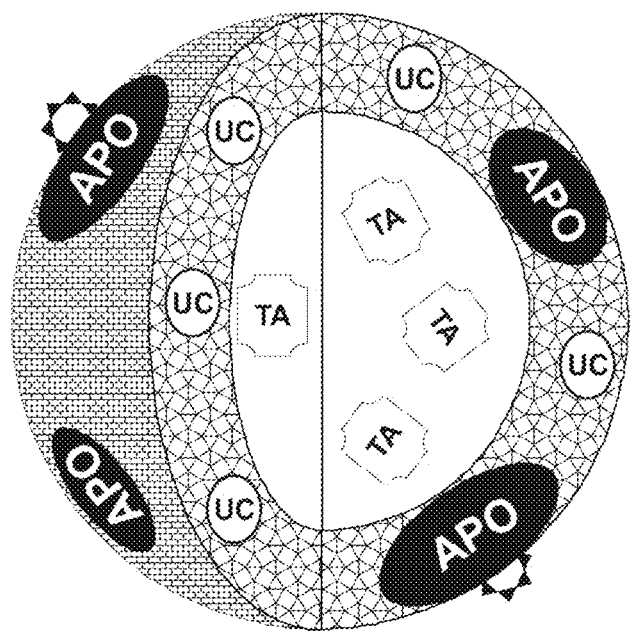
FIG. 2B presents a schematic representation of one embodiment of a spherical composition of the present invention with encapsulated therapeutic agents.

In one embodiment, the present invention contemplates a composition comprising a nanoparticle containing at least one modified molecule of apo A-I and/or apo A-II and/or fragments thereof as described herein. FIGS. 1, 2A, 2B. Although it is not necessary to understand the mechanism of an invention, it is believed that being incorporated into the compositions of the present invention, the modified apo A-I and/or apo A-II and/or fragments thereof, in addition to keeping the structural integrity of the nanoparticles of the invention, also target the nanoparticles to sites of interest such, for example, as atherosclerotic plagues or tumor sites.

Figure 4:
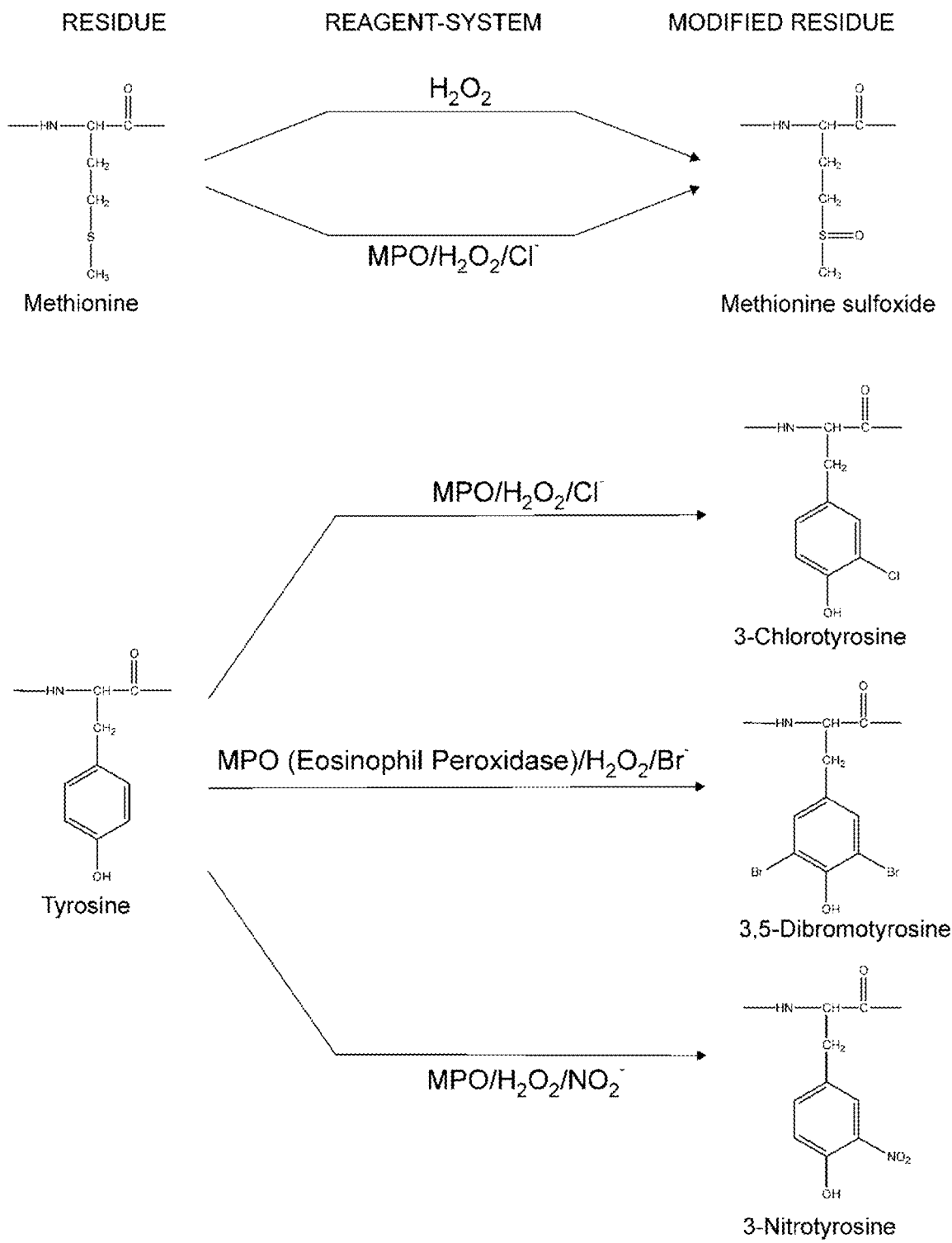
FIG. 4 contains examples of naturally occurring chemical and enzymatic modifications of amino acid residues of proteins including, but not limiting to, apolipoproteins of the present invention and fragments thereof. Abbreviation used: MPO—myeloperoxidase.

In preferred embodiments, the modified apolipoprotein is selected from a modified apo A-I or a fragment thereof and a modified apo A-II or a fragment thereof. In preferred embodiments, the modified apolipoprotein is any combination of a modified apo A-I and a modified A-II and fragments thereof. In still preferred embodiments, a modified apo A-I is an oxidized apo A-I or an oxidized apo A-I fragment that comprises one or more of the following amino acid residues: 3-chlorotyrosine, 3-nitrotyrosine, 3,5-dibromotyrosine, dityrosine, trihydroxyphenylalanine, dihydroxyphenylalanine, methionine sulfoxide, and tyrosine peroxide, or any combination thereof. FIG. 4 shows examples of such modified amino acid residues. In still other preferred embodiments, a modified apo A-II is an oxidized apo A-II or an oxidized apo A-II fragment that comprises one or more of the following amino acid residues: methionine sulfoxide, trihydroxyphenylalanine, dihydroxyphenylalanine, 3-chlorotyrosine, 3-nitrotyrosine, 3,5-dibromotyrosine, dityrosine, and tyrosine peroxide, or any combination thereof.

Those of skill in the art are aware that apo A-I contains three methionines that can potentially undergo sulfoxidation, Met-86, Met-112, and Met-148. As well known in the art and described in PCT Pat Appl PCT/US10/52117, sulfoxidation of apo A-I methionines 112 and 148 occurs in vivo and affects many HDL functions including uptake by macrophages. This and other naturally occurring apo A-I modifications (e.g. tyrosine chlorination, bromination and nitrosylation) can convert native HDL into a macrophage substrate (PCT Pat Appl PCT/US10/52117). See, FIG. 5.

Figure 5:
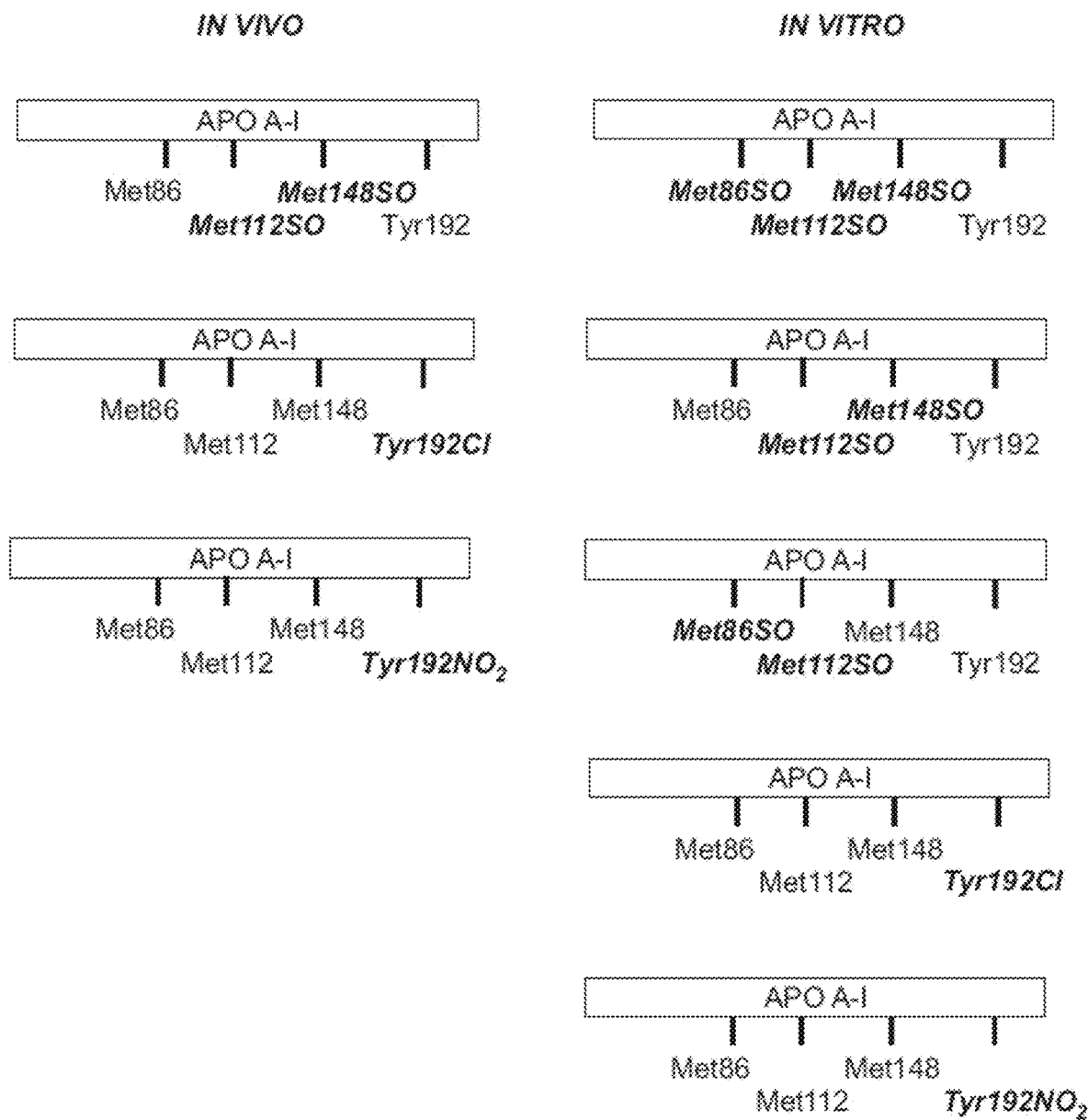
FIG. 5 presents a schematic representation of several modifications of apolipoprotein (apo) A-I naturally occurring in vivo and artificially produced in vitro. While not being bound to any particular theory, it is believed that Met residues at positions 112 and 148 are the major sites of sulfoxidation by hydrogen peroxide alone or in combination with myeloperoxidase in vivo, whereas sulfoxides of all three Met residues of apo A-I can be produced in different combinations in vitro, depending on the oxidant used. It is also believed that Tyr residue at the position 192 is the major of nitration and chlorination by myeloperoxidase in vivo and in vitro.
Figure 6:
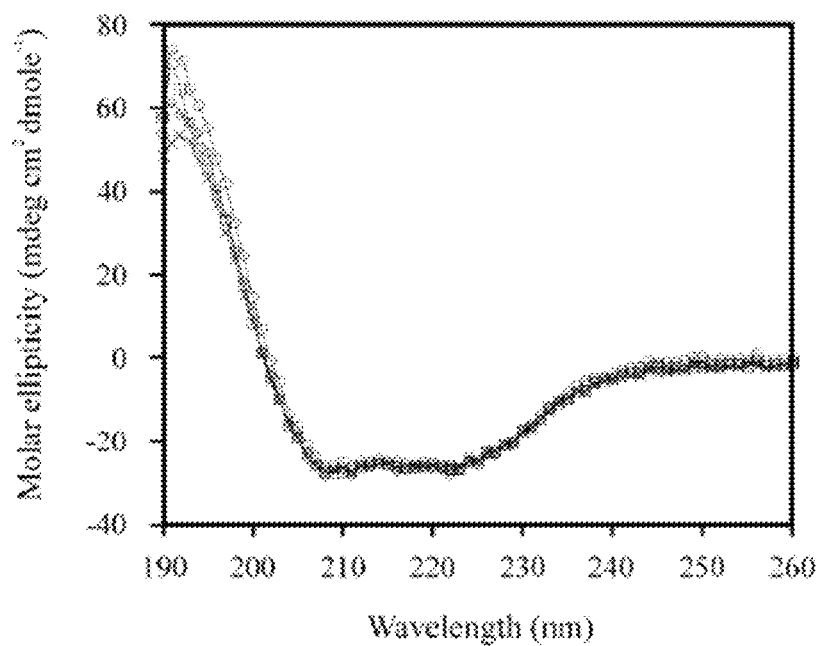
FIG. 6 presents exemplary data showing far-UV circular dichroism spectra of apo A-I on different rHDL particles. The spectra of lipid-associated apo A-I in rHDL-1 (open circles), rHDL-2 (open squares), rHDL-3 (open diamonds) and rHDL-4 (crossings) are shown.
Figure 7:
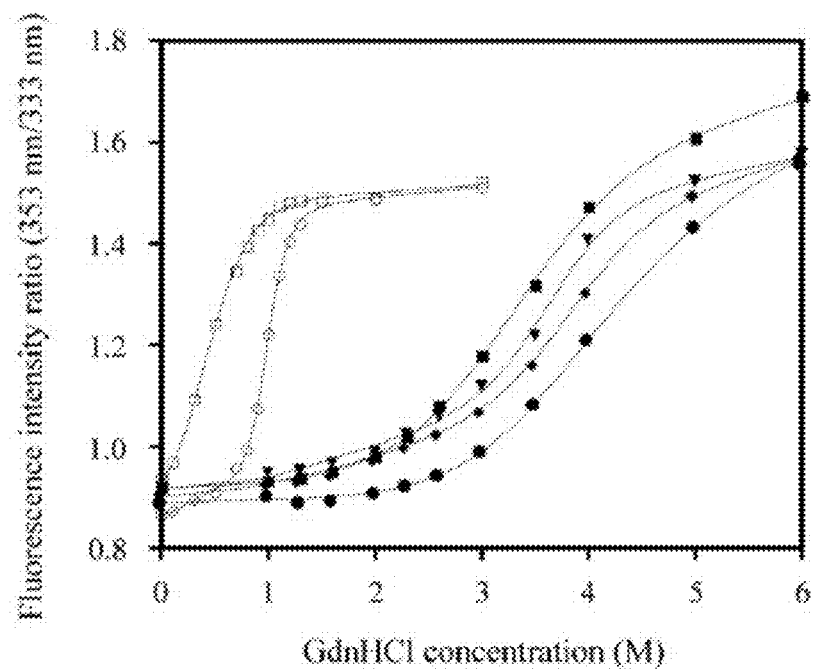
FIG. 7 presents exemplary data showing denaturation of lipid-free apo A-I and rHDL complexes by GdnHCl. Aliquots of unoxidized (open circles) and oxidized (open squares) lipid-free apo A-I proteins or prepared rHDL-1 (filled circles), rHDL-2 (filled squares), rHDL-3 (filled diamonds) and rHDL-4 (filled upside-down triangles) complexes were incubated at 4° C. with 0-6 M GdnHCl in 10 mM TBS, pH 7.4 for 72 h. The fluorescence intensities at 353 and 333 nm were measured with sample protein concentrations between 0.05 and 0.1 mg of protein/ml. The ratio of fluorescence intensity at 353 nm to that at 333 nm is plotted against the GdnHCl molar concentration.
Figure 8:
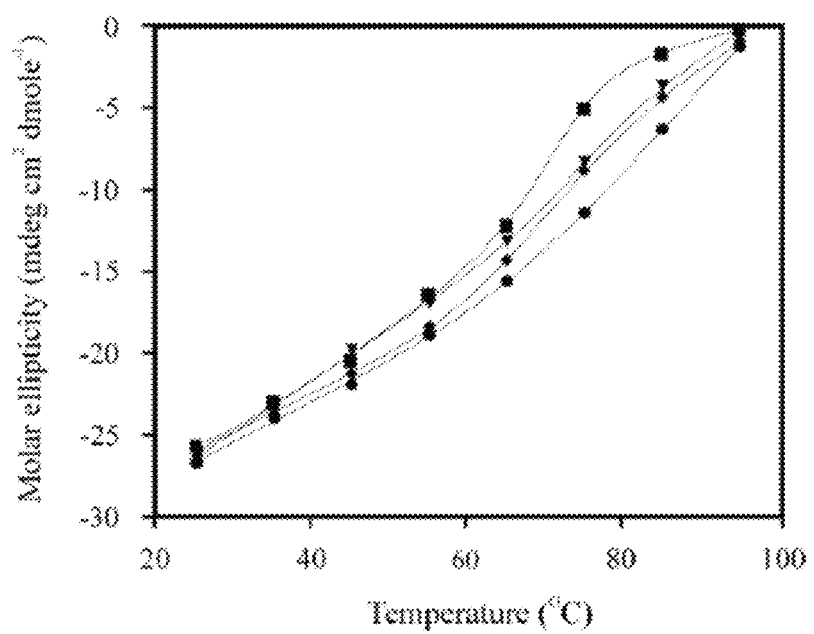
FIG. 8 presents exemplary data showing temperature-induced unfolding of rHDL complexes. The circular dichroic data were collected on solutions of rHDL-1 (filled circles), rHDL-2 (filled squares), rHDL-3 (filled diamonds) and rHDL-4 (filled upside-down triangles).
Figure 9:
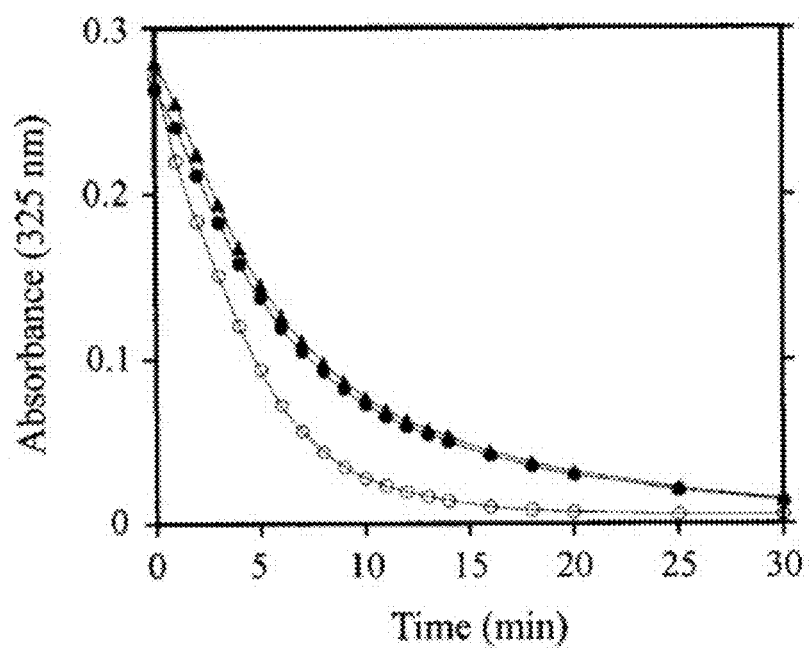
FIG. 9 presents exemplary data showing 1,2-dimyristoyl-sn-glycero-3-phosphocholine (DMPC) kinetic binding with unoxidized, oxidized, and reduced apo A-I proteins.

In particularly preferred embodiments, a modified apo A-I is an oxidized apo A-I or an oxidized apo A-I fragment that comprises methionine sulfoxide at any one of positions 86, 112, 148, or any combination of said positions (FIG. 5). In still particularly preferred embodiments, a modified apo A-II is an oxidized apo A-II or an oxidized apo A-II fragment that comprises methionine sulfoxide at position 26. In still preferred embodiments, apo A-I$_{unox}$, is unoxidized apo A-I contained in initial serum apo A-I. In other preferred embodiments apo A-II$_{unox}$, is unoxidized apo A-II contained in initial serum apo A-II. In other preferred embodiments, apo A-I$_{ox}$ is oxidized apo A-I (with sulfoxidized methionines at positions 112 and 148) contained in serum apo A-I or obtained from unoxidized apo A-I using hydrogen peroxide.

In certain embodiments, methionine sulfoxidation and the functional changes associated with the oxidation can be reversed by peptide methionine sulfoxide reductase (PMSR) in the presence of physiologically important universal antioxidant dihydrolipoic acid (DHLA) as a cofactor (PCT Pat Appl PCT/US10/52117). In preferred embodiments; apo A-I$_{red}$ is reduced apo A-I obtained by reduction of oxidized apo A-I (with sulfoxidized methionines at positions 112 and 148) using PMSR.

In preferred embodiments, apo A-I, apo A-II or fragments thereof are first chemically or enzymatically modified and then the synthetic nanoparticle of the invention is assembled using this modified apolipoprotein. It might be possible, however, to selectively modify only apolipoprotein portion of the fully assembled synthetic nanoparticle of the invention.

It is understood by those of ordinary skill in the art that the modified apo A-I and apo A-II molecules can be prepared and purified using the standard procedures well known in the art (see e.g. PCT Pat Appl PCT/US10/52117). It should be also understood by those of ordinary skill in the art that apo A-I and apo A-II peptide fragments containing modified amino acid residues can be easily synthesized or manufactured by any technique for peptide synthesis known in the art, including, e.g., the techniques described in U.S. Pat. Nos. 6,004,925, 6,037,323 and 6,046,166, and the modified peptides can be purified by any method known in the art, including high performance liquid chromatography (HPLC).

C. Reconstituted High Density Lipoproteins (rHDLs)

The preferred particles of the invention comprise an rHDL having at least one modified apo A-I and/or A-II or peptide fragments thereof and at least one amphipathic lipid, to form a particle that can be spherical or discoidal. The inclusion of an amphipathic apolipoprotein or peptide aids the structural stability of the particle, particularly when the particle has a discoidal shape. Exemplary proteins or peptides are selected from the major protein constituents of HDL, apo A-I and apo A-II, and peptide fragments thereof.

Those of skill in the art are aware of methods and compositions for producing reconstituted lipoproteins (US Pat Appls 20070243136; 20060217312; and 20060205643; U.S. Pat. No. 5,652,339), in general, and as delivery vehicles for imaging agents (US Pat Appl 20070243136 and PCT/US10/52117) and drugs (US Pat Appl 20090110739; U.S. Pat. Nos. 6,306,433, 7,824,709 and 6,514,523), in particular. Such methods include detergent mediated synthesis, cosonication of HDL components, or through the spontaneous interaction of apolipoproteins with lipids and are described below in more detail. Schematically, the rHDLs and HDL-like compositions of the present invention that contain modified apolipoproteins or fragments thereof are depicted in FIGS. 1, 2A and 2B.

Figure 10:
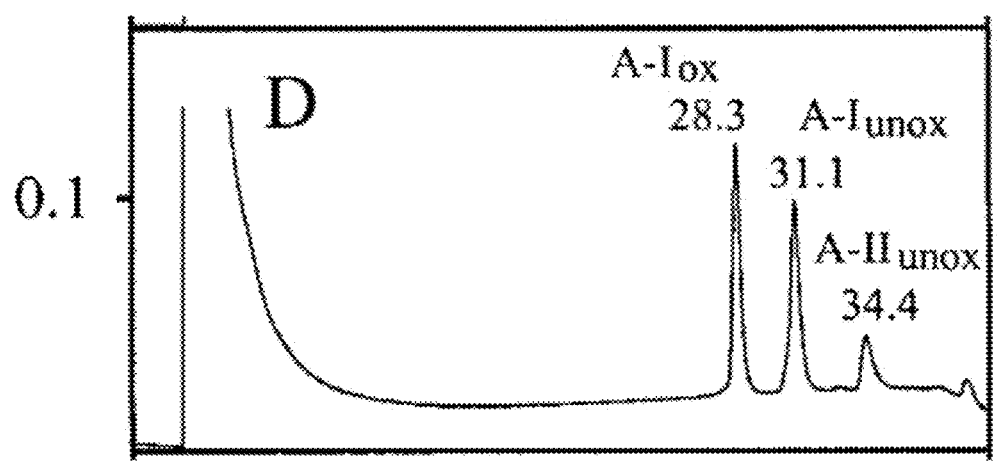
FIG. 10 presents exemplary data showing an analytical reversed-phase HPLC profile of apo A-I in rHDL particles containing apo A-I$_{unox}$, apo A-I$_{ox}$, and apo A-II$_{unox}$ with a molar ratio of 3:3:1 (rHDL-4). The retention times (in minutes) are shown above each peak.
Figure 11:
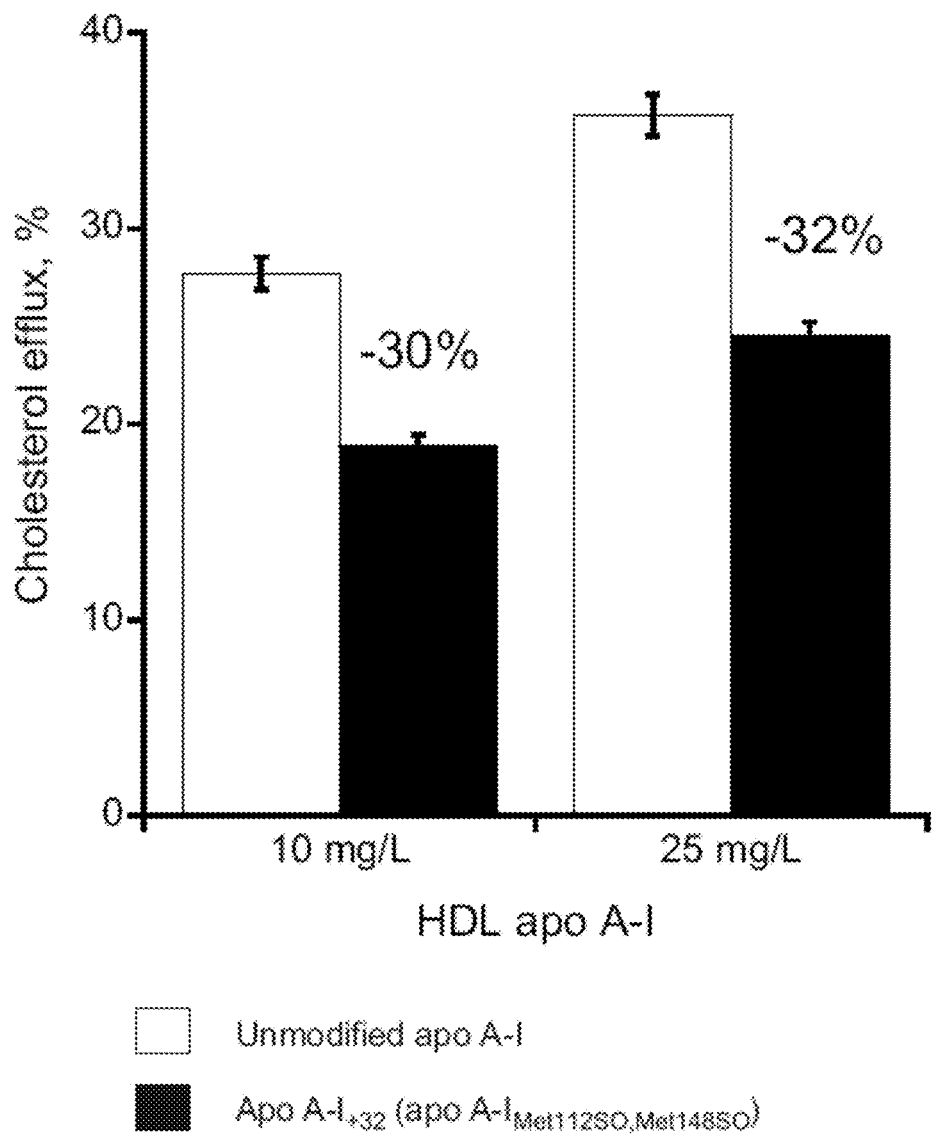
FIG. 11 presents exemplary data showing observed values of relative cholesterol efflux from cholesterol-loaded human skin fibroblasts promoted by HDL containing unmodified (unoxidized) apo A-I (empty bars) and oxidized (apo A-I$_{+32}$, or apo A-I$_{Met112SO,Met148SO}$) apo A-I (solid bars).

As described herein and disclosed in PCT Pat Appl PCT/US10/52117, modification of apolipoproteins does not significantly affect on their ability to interact with lipids and on the structure, stability, and other physico-chemical properties of the formed rHDL particles (FIGS. 6, 7, 8, and 9), and compositions of these particles can be analyzed using the standard methods well-known in the art, including HPLC. FIG. 10. Also, modification does not substantially impair the antiatherogenic ability of rHDL to promote cholesterol efflux. FIG. 11. Thus, the standard methods and compositions well-known in the art can be used to produce, characterize and use the compositions of the present invention.

In preferred embodiments, rHDL-1 are reconstituted HDL particles containing only apo A-I$_{unox}$. In preferred embodiments, rHDL-2 are reconstituted HDL particles containing only apo A-I$_{ox}$. In preferred embodiments, rHDL-3 are reconstituted HDL particles containing apo A-I$_{unox}$ and apo A-I$_0$ with a molar ratio of 1:1. In preferred embodiments, rHDL-4 are reconstituted HDL particles containing apo A-I$_{unox}$, apo A-I$_{ox}$ and apo A-II$_{unox}$ with a molar ratio of 3:3:1.

The compositions of the present invention have all known advantages of synthetic HDL-based imaging and drug delivery vehicles (US Pat Appls 20070243136 and 20090110739; PCT Pat Appl PCT/US10/52117; U.S. Pat. No. 7,824,709). A distinctive advantage of the methods and compositions of the present invention relative to other lipoprotein-based delivery vehicles known in the art, is that in the particles of the invention, modified apolipoproteins and fragments thereof serve not only as structural proteins that keep stability, integrity and functionality of rHDL and HDL-like compositions but importantly, as specific molecules that target the compositions of the invention to sites of interest. In specific embodiments, modified apolipoproteins and fragments thereof are substrates for macrophage scavenger receptors.

Figure 3A:
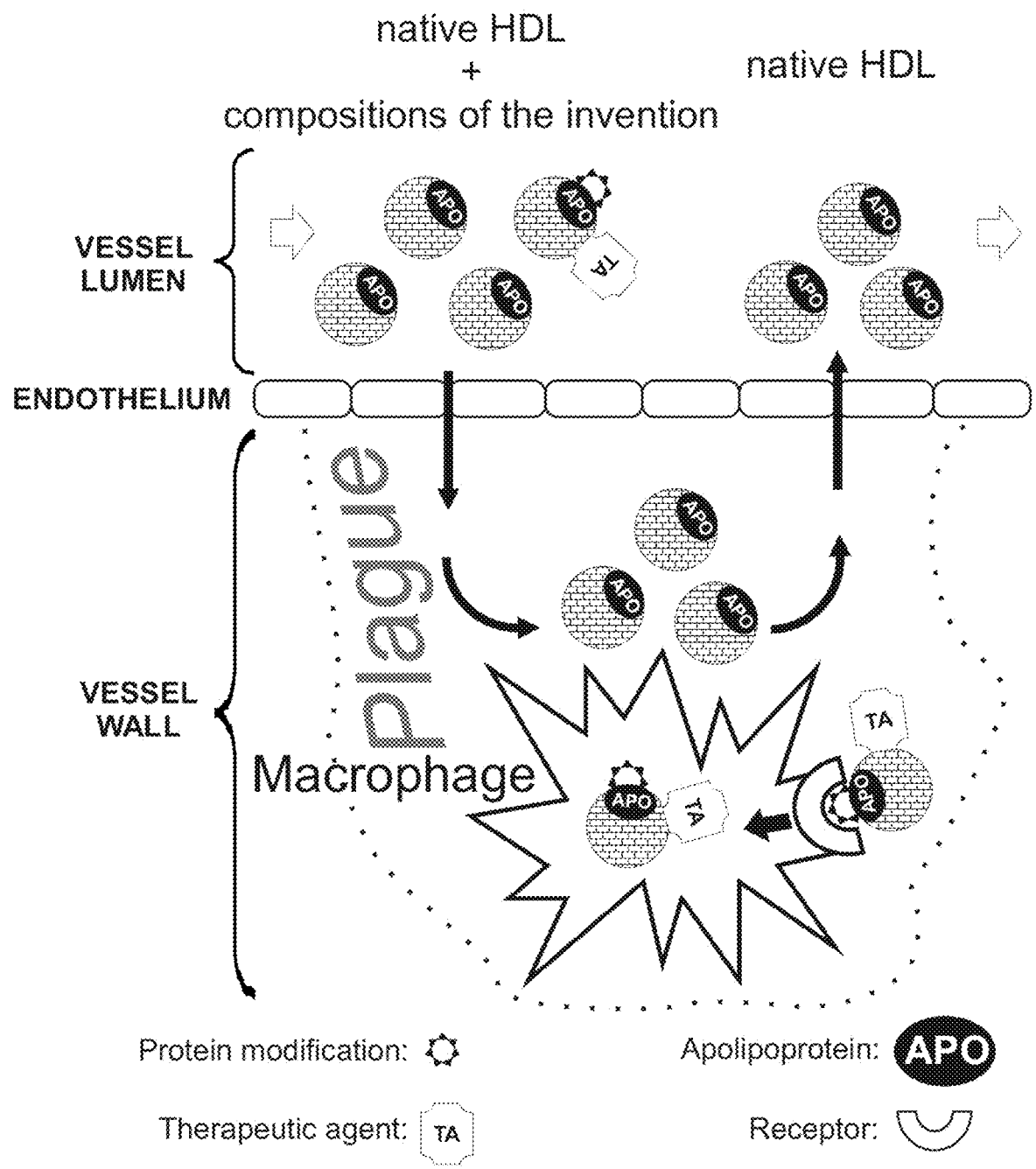
FIG. 3A illustrates a hypothesized molecular mechanism of action of a composition of the present invention with a therapeutic agent attached to said composition as applied to the treatment of atherosclerosis. While not being bound to any particular theory, it is believed that chemical and/or enzymatic modification of protein constituents of high density lipoprotein (HDL) and HDL-like particles of the present invention leads to the recognition of these particles by the macrophage scavenger receptors and results in an irreversible binding to and consequent uptake by macrophages of such particles. It is further believed that accumulation of these particles in the macrophages is accompanied by accumulation of therapeutic agents (TAs) covalently or non-covalently bound to the particles. In contrast, HDL particles that contain only unmodified apolipoprotein molecules are not recognized by macrophages and return to the circulation.
Figure 3B:
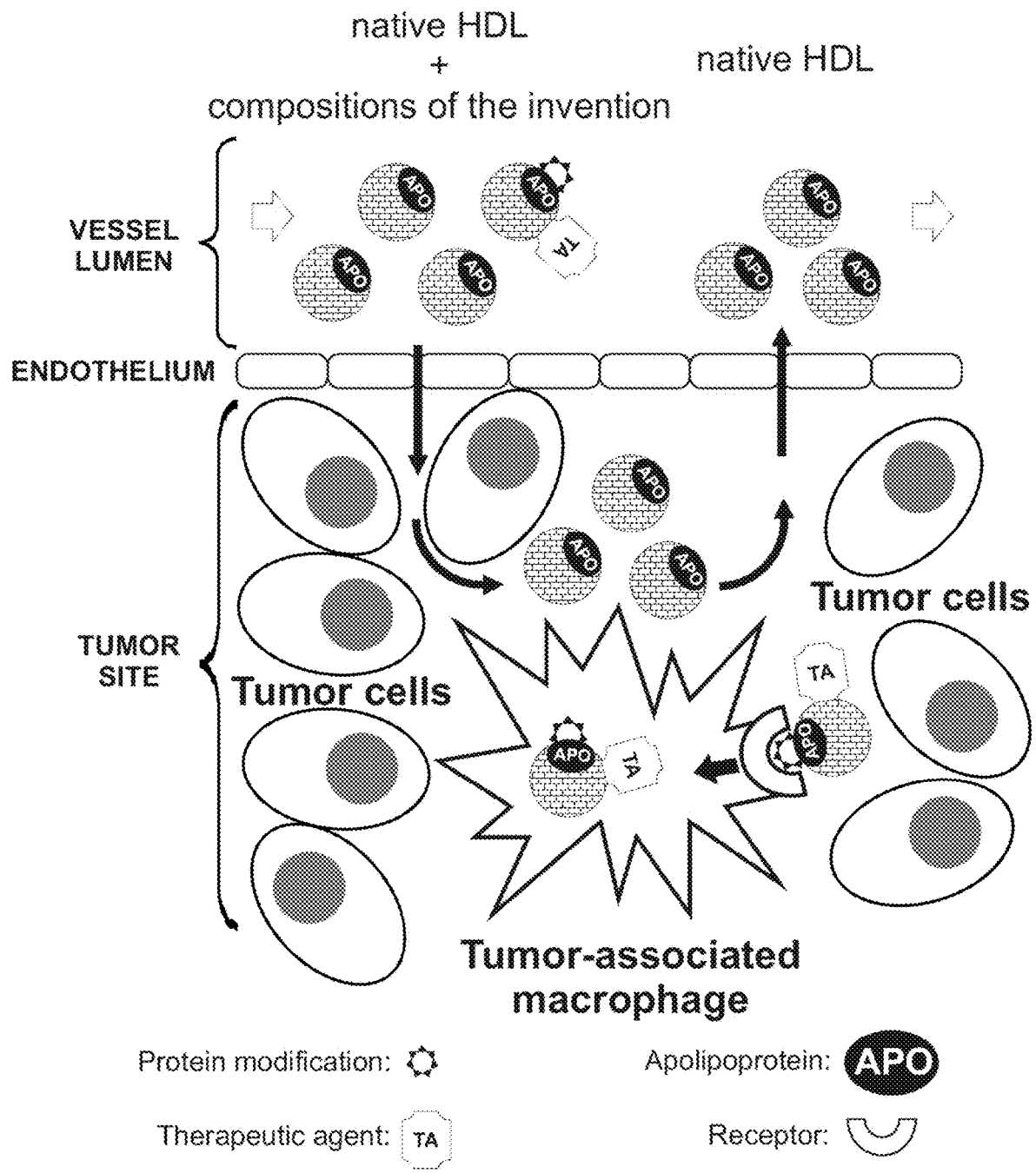
FIG. 3B illustrates a hypothesized molecular mechanism of action of a composition of the present invention with a therapeutic agent attached to said composition as applied to the treatment of cancer. While not being bound to any particular theory, it is believed that chemical and/or enzymatic modification of protein constituents of high density lipoprotein (HDL) and HDL-like particles of the present invention leads to the recognition of these particles by the macrophage scavenger receptors and results in an irreversible binding to and consequent uptake by tumor-associated macrophages of such particles. It is further believed that accumulation of these particles in the macrophages is accompanied by accumulation of therapeutic agents (TAs) covalently or non-covalently bound to the particles. In contrast, HDL particles that contain only unmodified apolipoprotein molecules are not recognized by macrophages and return to the circulation.

In treating cancer, this causes TA-rHDL particles (e.g., paclitaxel-rHDL particles) to be delivered to tumor-associated macrophages and retained in tumor sites (FIG. 3B). Similarly, in preventing and treating atherosclerosis, this causes TA-rHDL particles to be delivered to an atherosclerotic plaque (FIG. 3A). In one embodiment, additional targeting moieties can be used to further facilitate targeting of the compositions of the present invention to a specific site in vivo.

The present teachings disclose various nanoparticles that contain chemically and/or enzymatically modified apolipoproteins and are used for the targeted delivery of a therapeutic agent. The compositions of the present teachings include, but are not limited to, a synthetic nanoparticle, the synthetic nanoparticle comprising at least one chemically and/or enzymatically modified apolipoprotein A-I and/or A-II, at least one amphipathic lipid, and at least one therapeutic agent attached to said nanoparticle by a means selected from the group consisting of adsorption, incorporation, covalent bonding, chelating, and encapsulation. While the size of the nanoparticles is preferably between 5 nm and 25 nm, the diameter may be up to 150 nm. The disclosed nanoparticles may be spherical, discoidal or a distorted disc shape, e.g., ellipsoidal. In one embodiment, a chemotherapeutic drug, including but not limiting to, doxorubicin, doxorubicin derivatives, paclitaxel, as well as any combination of these agents, may be attached to said nanoparticle for the tumor-targeted delivery in the treatment of cancer. In another embodiment, the teachings provides a method and composition of targeted delivery of therapeutic agents in treating atherosclerosis and restenosis. In yet another aspect, the teachings provide a method and composition of the targeted delivery of therapeutic agents in treating bacterial infectious diseases.

Therefore, further disclosed herein is a synthetic nanoparticle. The synthetic nanoparticle comprises at least one modified apolipoprotein, at least one lipid; and at least one therapeutic agent. The therapeutic agent is attached to the nanoparticle by a means selected from the group consisting of adsorption, incorporation, covalent bonding, chelating, and encapsulation. The synthetic nanoparticle is discoidal or spherical in shape and has a diameter of from about 5 nm to about 150 nm. The modified apolipoprotein of the nanoparticle may contain at least one amino acid residue which is chemically or enzymatically modified. The modified apolipoprotein may be an oxidized apolipoprotein. The oxidized apolipoprotein may contain at least one amino acid residue which is oxidized. The oxidized residue may be a methionine. The modified apolipoprotein may contain at least one amino acid residue which is oxidized, halogenated, or nitrated. The modified apolipoprotein may include an amphipathic apolipoprotein or a fragment thereof. The modified apolipoprotein may include a modified apolipoprotein A-I, A-II, A-IV, B, C-I, C-II, C-III, or E. In another aspect, the synthetic nanoparticle may comprise any protein. The protein may comprise apolipoprotein A-I, A-II, A-IV, B, C-I, C-II, C-III, or E. In yet another aspect, the synthetic nanoparticle may comprise a targeting moiety to enhance the targeting efficacy of the therapeutic agent. The targeting moiety may include a protein, a polypeptide, an antibody, a receptor, a ligand, a peptidomimetic agent, an aptamer or a product of phage display. In still another aspect, the synthetic nanoparticle may comprise a therapeutic agent selected from the group anticancer, antibacterial, antiviral, autoimmune, anti-inflammatory and cardiovascular agents, antioxidants, therapeutic peptides. The therapeutic agent may also be selected from the group comprising paclitaxel, valrubicin, doxorubicin, taxotere, campotechin, etoposide, and any combination thereof. The lipid of the synthetic nanoparticle may include cholesterol, a cholesteryl ester, a phospholipid, a glycolipid, a sphingolipid, a cationic lipid, a diacylglycerol, or a triacylglycerol. And further, the phospholipid may include phosphatidylcholine (PC), phosphatidylethanolamine (PE), phosphatidylserine (PS), phosphatidylinositol (PI), phosphatidylglycerol (PG), cardiolipin (CL), sphingomyelin (SM), or phosphatidic acid (PA). And even further, the cationic lipid can be 1,2-dioleoyl-3-trimethylammonium-propane (DOTAP). The lipid of the synthetic nanoparticle may be polyethylene glycol(PEG)ylated.

The disclosure further provides for a method of making a synthetic nanoparticle. The method comprises co-dissolving a predetermined amount of a mixture of neutral and/or charged lipids with a predetermined amount of a therapeutic agent and a predetermined amount of modified apolipoprotein. The co-dissolving is conducted for a time period sufficient to allow the mixture to coalesce into structures whereby particles are formed incorporating the therapeutic agent. The method further comprises isolating structures that have a size of between about 5 to about 50 nm diameter. The lipid of the method may include PC, PE, PS, PI, PG, CL, SM, DOTAP or PA. The modified apolipoprotein of the method may include modified apolipoprotein A-I, A-II, A-IV, B, C-I, C-II, C-III, or E.

The disclosure also provided for a method of making a synthetic nanoparticle comprising co-dissolving a predetermined amount of a mixture of neutral and/or charged lipids with a predetermined amount of cholesterol, a predetermined amount of HDL core lipids comprising triglycerides and/or cholesteryl ester, and a predetermined amount of a therapeutic agent. The method further comprises drying the mixture under nitrogen. The method even further comprises co-dissolving the dried mixture of with a predetermined amount of sodium cholate and a predetermined amount of modified apolipoprotein. The co-dissolving is conducted for a time period sufficient to allow the components to coalesce into structures. The method still further comprises removing sodium cholate from the mixture, and isolating structures that have a size of between about 5 to about 100 nm diameter. The lipid of the method may include PC, PE, PS, PI, PG, CL, SM, DOTAP, or PA. The modified apolipoprotein of the method may include modified apolipoprotein A-I, A-II, A-IV, B, C-I, C-II, C-III, or E.

D. Reconstituted Lipoprotein Particles (rLPSs) for Targeted Delivery

The disclosure also provides for a method of generating a therapeutic agent-incorporated synthetic nanoparticle. The method comprises co-dissolving a predetermined amount of a lipid with a predetermined amount of cholesterol, a predetermined amount of modified apolipoprotein, and a predetermined amount of a therapeutic agent. The co-dissolving is conducted for a time period sufficient to allow the mixture to coalesce into structures whereby particles are formed incorporating the therapeutic agent. The method further comprises isolating structures that have a size of between about 5 to about 150 nm diameter. The lipid of the method may comprise DOTAP. The modified apolipoprotein of the method may include modified apolipoprotein A-I, A-II, A-IV, B, C-I, C-II, C-III, or E.

The disclosure also provides for a method of treating a macrophage-related condition. The method comprises providing a composition comprising a synthetic nanoparticle of the present disclosure, a patient having at least one symptom of a disease or condition in which macrophages are involved or recruited, and administering the composition to the patient under conditions such that said one symptom is reduced. The macrophage-related condition of the method may include a heart disease, peripheral artery disease, restenosis, stroke, the cancers (e.g., sarcoma, lymphoma, leukemia, carcinoma and melanoma), bacterial infectious diseases, acquired immune deficiency syndrome (AIDS), allergic diseases, autoimmune diseases (e.g., rheumatoid arthritis, Sjogrens, scleroderma, systemic lupus erythematosus, non-specific vasculitis, Kawasaki's disease, psoriasis, type I diabetes, pemphigus vulgaris), granulomatous diseases (e.g., tuberculosis, sarcoidosis, lymphomatoid granulomatosis, Wegener's granulomatosus), Gaucher's disease, inflammatory diseases (e.g., sepsis, inflammatory lung diseases such as interstitial pneumonitis and asthma, inflammatory bowel disease such as Crohn's disease, and inflammatory arthritis), and transplant (e.g., heart/lung transplants) rejection reactions.

The use of non-viral nanoparticulate systems for the delivery of therapeutic agents is receiving considerable attention for medical and pharmaceutical applications. The increasing interest results from the fact that these systems can be designed to meet specific physicochemical requirements, and they display low toxic and immunogenic effects. Among potential cellular targets by drug-loaded nanoparticles, macrophages are considered because they play a central role in inflammation and they act as reservoirs for microorganisms that are involved with deadly infectious diseases. The most common and potent drugs used in the treatment of cancer, bacterial infectious diseases, and other macrophage-mediated diseases often induce unwanted side effects, when applied as a free form, due to the necessity of high doses to induce a satisfactory effect. This could result in their systemic spreading, a lack of bioavailability at the desired sites, and a short half-life. Therefore, the use of drug-loaded nanoparticles represents a good alternative to avoid, or at least decrease, side effects and increase efficacy.

Lipoprotein particles (lipoproteins) have been used previously as delivery vehicles for drugs (U.S. Pat. Nos. 6,306,433, 7,824,709 and 6,514,523; US Pat Appl 20090110739). Lipoproteins are the native transporters in the circulation of a variety of lipophilic and hydrophilic compounds and are classified into four main categories depending on size and composition (i.e., in order of decreasing diameter: chylomicrons, very low density lipoproteins (VLDL), low- and high-density lipoproteins (LDL and HDL, respectively). With the exception of HDLs, the lipoproteins suffer the same drawbacks as micelles, conventional emulsions and liposomes, in that the entities are too large to serve as good vehicles for the delivery of therapeutic agents. In comparison to other drug delivery platforms, HDL or HDL-like lipoprotein particles have several advantages: 1) the protein constituent of HDL, apolipoprotein (apo) A-I, is an endogenous protein component and does not trigger immunoreactions, 2) the small size of the HDL particle (8-12 nm) allows to pass through blood vessel walls, 3) the small particle size also allows for intravenous, intramuscular and subcutaneous applications, and 4) a variety of therapeutic and imaging agents can be incorporated into this platform (U.S. Pat. Nos. 6,306,433, 7,824,709 and 6,514,523; US Pat Appls 20070243136 and 20090110739; PCT Pat Appl PCT/US10/52117). There has been increased activity in the patenting of lipoprotein-like formulations in the last several years, primarily with the aim of developing enhanced delivery vehicles for therapeutics and diagnostics.

Synthetic HDL (recombinant, or reconstituted HDL; rHDL) have been used as a vehicle for tumor-targeted delivery of PTX (US Pat Appl 20090110739). One of the major limitations of the suggested PTX-rHDL formulations includes low specificity of drug delivery to the tumor in vivo. The uptake of PTX from drug-loaded rHDL particles is facilitated by the scavenger receptor B type I (SR-BI), the receptor that is found in numerous cell types/tissues, including the liver and adrenal. Also, delivery of therapeutic agents by these particles to the tumor strongly depends on SR-BI expression level on cancer cells that may differ in various types of cancer and for patients at different stages of cancer.

It is well understood by those of skill in the art that the standard methods well-known in the art can be used to synthesize reconstituted lipoprotein and lipoprotein-like particles that contain imaging agents (US Pat Appl 20070243136 and PCT Pat Appl PCT/US10/52117) or drugs (US Pat Appl 20090110739; U.S. Pat. Nos. 6,306,433, 7,824,709 and 6,514,523; Oda et al. J Lipid Res 2006; 47:260-7; Kim et al. J Hepatol 2009; 50:479-88).

As described in Kim et al. J Hepatol 2009; 50:479-88, and disclosed in PCT Pat Appl PCT/US10/52117, U.S. Pat. Nos. 6,306,433, 7,824,709 and 6,514,523; US Pat Appls 20070243136 and 20090110739, the lipoprotein complexes described herein can be prepared in a variety of forms, including, but not limited to vesicles, liposomes, proteoliposomes, micelles, discoidal and spherical particles.

In preferred embodiments, the rHDL complexes are prepared by the sodium cholate dialysis method with an initial molar ratio of sodium cholate-POPC-cholesterol-apo A-I of 150:80:4:1. This method has been used previously to prepare rHDL with 2 or 3 apo A-I per particle and 9-11 nm diameter.

An aliquot of the resulting reconstituted preparation can be characterized to confirm that the complexes in the preparation have the desired size distribution; e.g., the size distribution of HDL. Characterization of the reconstituted preparation can be performed using any standard method known in the art, including, but not limited to, HPLC (see e.g., FIG. 10), size exclusion chromatography, gel filtration, column filtration, gel permeation chromatography, and non-denaturating gel electrophoresis.

In one embodiment, macrophage scavenger receptors can be used in a functional assay to identify which complex is the most effective in being absorbed and/or taken-up by macrophages. In one assay, the complexes can be tested for their ability to bind macrophage scavenger receptors. Such an assay can differentiate macrophage scavenger receptor-dependent on independent binding to and/or uptake by macrophages. Standard assays that are well known in the art can be used herein to assess binding, uptake and degradation of the compositions of the present invention by macrophages.

The preferred particles of the invention comprise at least one modified apolipoprotein or peptide fragments thereof, at least one amphipathic lipid, and at least one drug attached to these particles by a means selected from the group consisting of adsorption, incorporation, covalent bonding, chelating, and encapsulation.

In one embodiment, the TA comprises the chemotherapeutic agent useful for treating cancer may preferably be selected from the group consisting of doxorubicin (DOX), doxorubicin derivatives (e.g., epirubicin, idarubicin and zyn-linked doxorubicin), paclitaxel (PTX, Taxol®), Taxotere®, campotechin, cisplatin, and the like, as well as of combinations of these agents. In other embodiments, TAs that can be incorporated into the compositions of the present inventions include, but are not limited to, antibiotic agents (bleomycin, mitomycin, amphotericin B, plicamycin, and the like, as well as combinations of these agents), alkylating agents (busulfan, carmustin, lomustine, melphatan, chlorambucil, cyclophosphamide, mechlorethamine, semustine, and the like, as well as combinations of these agents), azidothymidine (AZT), antioxidants (e.g. DHLA), anti-metabolic agents (floxuridine, mercaptopurine, fluorouracil, methotrexate, and the like, as well as combinations of these agents), and mitotic inhibitor agents (etoposide, vinblastine, vindesine, and the like, as well as combinations of these agents).

In preferred embodiments, the TA may preferably be selected from the group of therapeutic proteins and peptides that include, but are not limited to, human growth hormone, bovine growth hormone, vascular endothelial growth factor, fibroblast growth factors, bone morphogenic protein, tumor necrosis factors, erythropoietin, thrombopoietin, tissue plasminogen activator, insulin, antibodies, type-1 interferon, luteinizing hormone releasing hormone (LHRH) inhibitor peptides, vasopressins, platelet aggregate inhibitors, calcitonins, somatostatins, etc. These and other therapeutic proteins and peptides including, but not limiting to, those that are disclosed in US Pat Appl 20070172653 and described in Vlieghe et al. Drug Discov Today 2010; 15:40-56, can be used in the present invention. In still preferred embodiments, the therapeutic peptides include, but are not limited to, peptide inhibitors of immune receptors, T cell receptor (TCR) and triggering receptor 1 expressed on myeloid cells (TREM-1) designed using a novel model of transmembrane signaling, the Signaling Chain HOmoOLigomerization (SCHOOL) model, as disclosed in U.S. patent application Ser. No. 12/895,454 and PCT Pat Appl PCT/US10/52566, other SCHOOL peptide inhibitors (see e.g., US Pat Appl 20090075899), and the like, as well as combinations of these peptide inhibitors.

In preferred embodiments, imaging agents are attached to synthetic nanoparticles of the present invention by a means selected from the group consisting of adsorption, incorporation, covalent bonding, chelating, and encapsulation as described in US Pat Appl 20070243136 and PCT Pat Appl PCT/US10/52117.

In one embodiment, the TA is conjugated to a lipid component of the synthetic nanoparticle. Such a lipid component of the synthetic nanoparticle may be selected from the group consisting of a sterol, a phospholipid, a sterol ester, a diacylglycerol and a triacylglycerol. In certain embodiments, the sterol of the compositions of the present invention is cholesterol. In other embodiments, the sterol ester is cholesteryl ester. In still preferred embodiments, the TA is encapsulated into the synthetic lipoprotein-like nanoparticle.

It is contemplated that the TA may alternatively be conjugated to a modified protein component of the synthetic nanoparticle. Such a modified protein may be selected from the group consisting of a modified apo A-I or fragments thereof, a modified A-II or fragments thereof, and any combination of a modified apo A-I and a modified A-II and fragments thereof.

For the compositions of the present invention, it is critical that the synthetic nanoparticle contain at least one modified molecule of apo A-I and/or apo A-II and/or fragments thereof (FIGS. 1, 2A, 2B). In certain embodiments, the compositions of the present inventions may also comprise unmodified apo A-I and/or apo A-II and/or fragments thereof. In other embodiment, the synthetic nanoparticle of the invention may optionally contain other modified and/or unmodified apolipoproteins including, but not limiting to, A-IV, B, C-I, C-II, C-III, and E, and any combination thereof. In some embodiments, the compositions of the present inventions may optionally comprise protein fragments of modified and/or unmodified apolipoproteins including, but not limiting to, A-IV, B, C-I, C-II, C-III, and E, and any combination thereof.

According to the present invention, HDL-like particle is particularly preferred which has a molar ratio of a modified apolipoprotein (selected the group consisting of a modified apo A-I or fragments thereof, a modified A-II or fragments thereof, and any combination of a modified apo A-I and a modified A-II and fragments thereof) and phospholipid in the range of 1:50 to 1:250, particularly about 1:150. Further, rHDL may optionally contain additional lipids such as cholesterol, cholesterol esters, triglycerides and/or sphingolipids, preferably in a molar ratio of up to 1:20, e.g. 1:5 to 1:20 based on the apolipoprotein. Preferred rHDL is disclosed in U.S. Pat. Nos. 6,306,433, 7,662,410; 7,824,709 and 6,514,523; US Pat Appl 20090110739, PCT Pat Appl PCT/US10/52117, and described in Kim et al. J Hepatol 2009; 50:479-88.

In some aspects of the present invention, rHDL may be prepared from a modified apolipoprotein (selected the group consisting of a modified apo A-I or fragments thereof, a modified A-II or fragments thereof, and any combination of a modified apo A-I and a modified A-II and fragments thereof), and soybean-derived PC, mixed in molar ratios of approximately 1:150 apolipoprotein:PC. In preferred embodiments, egg yolk-derived PC can be used to synthesize the TA-containing HDL-like particles of the invention (US Pat Appl 20090110739).

In still preferred embodiments, HDL-like particle may comprise 1,2-dioleoyl-3-trimethylammonium-propane (DOTAP) and cholesterol.

In preferred embodiments, the synthetic nanoparticle of the invention comprises a phospholipid:sterol:apolipoprotein ratio of 180:5:3 (mol:mol:mol). In other preferred embodiments, the synthetic nanoparticle of the invention comprises a phospholipid:apolipoprotein ratio of 100:3 (mol:mol). In still preferred embodiments, the synthetic nanoparticle of the invention comprises a phospholipid:steryl ester:sterol:triglycerides (TG):apo A-I ratio (w/w) of 100:62:25:11:2. In other preferred embodiments, the synthetic nanoparticle comprises a DOTAP:cholesterol ratio of 1:1 (mol:mol) and a lipid/apo A-I protein ratio of 10:1 (w/w). In still other preferred embodiments, the particle of the invention comprises phospholipid bilayers of phosphatidylcholines (PC) and/or phosphatidylglycerol (PG) synthesized as disclosed in U.S. Pat. No. 7,824,709.

The compositions of the invention may comprise between about 80 and about 180 phospholipids per synthetic nanoparticle. Other embodiments define the composition as comprising 2, 3 or 4 apolipoprotein molecules and/or fragments thereof per synthetic nanoparticle. In still further embodiments, the synthetic nanoparticle comprises 1 apolipoprotein molecule and/or fragments thereof to between about 30 and about 60 phospholipid molecules.

The compositions of the invention may further comprise an additional moiety to further facilitate targeting of the agent to a specific site in vivo. The additional targeting moiety may be any moiety that is conventionally used to target an agent to a given in vivo site and may include but is not limited to, an antibody, a receptor, a ligand, a peptidomimetic agent, an aptamer, a polysaccharide, a drug and a product of phage display. In particular embodiments, the targeting moiety may be conjugated to a detectable label. For example, apo E-derived lipopeptide, an apo A-I mimetic peptide, murine (MDA2 and E06) or human (IK17) antibodies that bind unique oxidation-specific epitopes, and gold particles may be used in the present invention to further improve specific targeting macrophages and decrease the required dosage of administered TAs.

Preferably, the diameter or the longest dimension of the nanoparticle is between about 5 nm to about 18 nm. The diameter may be between about 5 to about 12 nm. In particularly preferred embodiments, the diameter is less than 10 nm. In some embodiments the diameter is more than 100 nm.

The composition of the invention may be one which comprises two or more different TAs. In additional embodiments, the composition may further comprise the imaging agents to be delivered together with a TA to sites of interest in vivo and in vitro. In one embodiment, these imaging agents may be selected from the metallic and non-metallic contrast agents disclosed in US Pat Appl 20070243136 and PCT Pat Appl PCT/US10/52117 as well as from any combinations of the imaging and therapeutic agents.

The present invention provides rHDL compositions and HDL-like compositions. These particles can be discoidal and spherical in shape. The compositions of the present invention all contain modified apolipoproteins or fragments thereof (FIGS. 1, 2A, 2B). The particles of the invention are used for targeted delivery of TAs to sites of interest in vivo and in vitro. The TAs are attached to synthetic nanoparticles of the present invention by a means selected from the group consisting of adsorption, incorporation, covalent bonding, chelating, and encapsulation.

Thus, the compositions of the present invention comprise a TA-containing synthetic HDL moiety, the major protein structural components of which, apolipoproteins, or fragments thereof are modified in a means for converting them into specific moieties (for example, into substrates for macrophages) for targeted delivery of HDL-associated TAs to sites of interest (for example, atherosclerotic plaques or tumor sites). The use of synthetic HDL particles that contain modified apolipoproteins or fragments thereof for the targeted drug delivery in vivo is advantageous because after administration, most of these particles get bound and/or taken-up by cells at sites of interest (FIGS. 3A and 3B). This allows a significant reduction in the TA dosage required and thereby limits concerns related to systemic toxicity, which is especially important for chemotherapeutic anticancer agents.

Native HDL particles that contain unmodified lipids and apolipoproteins are not recognized by macrophage scavenger receptors. As a result, native HDL do not irreversibly bind to macrophages and are not taken-up by macrophages. In contrast, modified (for example, oxidized) HDL are readily absorbed by macrophages resulting to accumulation of the modified HDL and their components in macrophage-rich sites such as an atherosclerotic plaque and tumor sites. As described herein, it is unexpectedly found that oxidative modification of only protein constituents or peptide fragments thereof of rHDL is sufficient to convert these particles to substrates for macrophage scavenger receptors and to result therefore in the improvement of association of the TA-(HDL/modified apolipoprotein)-particle with macrophages and/or absorption (uptake) of TA-(HDL/modified apolipoprotein)-particle by macrophages when compared to that of the TA-(HDL/apolipoprotein)-particle constructed with naturally occurring unmodified apo A-I, apo A-II or fragments thereof. Compositions of the invention contain certain chemical or enzymatic modification of apolipoproteins (apo) A-I or A-II or fragments thereof and can be easily and reproducibly produced. The preferred modifications of the apolipoprotein components of the compositions of the invention are those that occur in vivo (e.g., methionine sulfoxidation).

The preferred particles of the invention comprise at least one modified apo A-I and/or A-II or peptide fragments thereof and at least one amphipathic lipid, to form a structure that can be spherical or discoidal. To readily penetrate into the interstitial fluid, the particles must be 25 nm or less in diameter, if spherical, or 25 rim or less in their longest dimension, if discoidal. For structural stability, ease of manufacture, and ability to carry significant amounts of contrast and/or targeting agents, the particles should be at least 5 nm in their largest dimension.

In particularly preferred aspects of the invention the synthetic HDL are reconstituted with the therapeutic agent, modified apolipoproteins and/or fragments thereof, and a second agent that allows the additional targeting of the composition to a specific site. While some of the discussion herein focuses on atherosclerotic plaques and tumor sites, it should be understood that other sites in the body also may be targeted with the compositions of the invention.

As described herein it is unexpectedly found that the TA-containing synthetic HDL composition can be specifically targeted to macrophage-rich sites of interest by chemical or enzymatic modification of the major protein constituents of HDL, apo A-I and A-II, or fragments thereof, solving therefore numerous problems which otherwise are associated with high dosages of TA required and low specificity of formulations in macrophage-targeted drug delivery.

It is contemplated that the compositions of the present invention, in addition to comprising a therapeutic agent and/or a metallic or non-metallic contrast agent (PCT Pat Appl PCT/US10/52117), also may comprise a third agent that is being delivered to affect a therapeutic outcome. Any agent can be delivered in this manner and methods of using lipoproteins to deliver drugs are well known to those of skill in the art (see e.g., U.S. Pat. Nos. 6,306,433, 7,824,709 and 6,514,523; US Pat Appl 20090110739). The therapeutic agent that may be used in the compositions of the invention is limited only by the features that it should not destroy the structural integrity of the rHDL or HDL-like particle.

In specific embodiments, the compositions of the present invention may contain naturally occurring dihydrolipoic acid (DHLA) or its precursor, lipoic acid (LA) to deliver these therapeutic agents to sites of interest in vitro and in vivo (e.g., an atherosclerotic plague). DHLA is formed in vivo from LA, which is widely used as a therapeutic agent in a variety of diseases (see e.g., US Pat Appls 20090068264, 20020110604, and 20020177558). Several lines of evidence suggest that the antioxidant properties of LA and more importantly, its reduced form, DHLA, are at least in part responsible for the therapeutic effect.

DHLA is known in the art to serve as a cofactor for peptide methionine sulfoxide reductase (PMSR), the enzyme that reduces sulfoxidized methionines back to their native form. Therefore, it is contemplated, the compositions of the present invention, in addition to comprising a TA and/or imaging agent (PCT Pat Appl PCT/US10/52117), also may comprise DHLA and/or LA that is being delivered to effect a therapeutic outcome (for example, to reduce methionine sulfoxides in human apo A-I and A-II of atherosclerotic plagues back to their native form). In certain embodiments, the modified apolipoproteins of the compositions of the invention are methionine sulfoxide-containing apo A-I, A-II and/or fragments thereof. Incorporation of DHLA and/or LA in these compositions may result in reducing apolipoprotein methionine sulfoxides of the rHDL compositions back to native methionines after delivery of TAs to sites of interest such, for example, as atherosclerotic plagues and tumor sites.

E. Apolipoprotein Fragments

In one embodiment, the synthesized rHDLs are discoidal (GF9-dHDL). In one embodiment, the synthesized rHDLs are spherical (GF9-sHDL). This suggests that a full length apolipoprotein molecule can be replaced by an apolipoprotein fragment without compromising rHDL activity in an macrophage uptake assay. In one embodiment, combinations of different apolipoprotein fragments and compositions of the invention are contemplated.

The present teachings disclose various nanoparticles that contain chemically and/or enzymatically modified apolipoprotein fragments and are used for the targeted delivery of a therapeutic agent. The compositions of the present teachings include, but are not limited to, a synthetic nanoparticle, the synthetic nanoparticle comprising at least one chemically and/or enzymatically modified fragments of apolipoprotein A-I and/or A-II, at least one lipid, and at least one therapeutic agent attached to said nanoparticle by a means selected from the group consisting of adsorption, incorporation, covalent bonding, chelating, and encapsulation. While the size of the nanoparticles is preferably between 5 nm and 25 nm, the diameter may be up to 200 nm. The disclosed nanoparticles may be spherical, discoidal or a distorted disc shape, e.g., ellipsoidal. In one embodiment, a chemotherapeutic drug, including but not limiting to, doxorubicin, doxorubicin derivatives, paclitaxel, as well as any combination of these agents, may be attached to said nanoparticle for the tumor-targeted delivery in the treatment of cancer. In another embodiment, the teachings provides a method and composition of targeted delivery of therapeutic agents in treating atherosclerosis and restenosis. In yet another aspect, the teachings provide a method and composition of the targeted delivery of therapeutic agents in treating bacterial infectious diseases. In yet another aspect, the teachings provide a method and composition of the targeted delivery of therapeutic agents in treating inflammation-associated diseases.

Therefore, further disclosed herein is a synthetic nanoparticle. The synthetic nanoparticle comprises at least one modified apolipoprotein fragment, at least one lipid; and at least one therapeutic agent. The therapeutic agent is attached to the nanoparticle by a means selected from the group consisting of adsorption, incorporation, covalent bonding, chelating, and encapsulation. The synthetic nanoparticle is discoidal or spherical in shape and has a diameter of from about 5 nm to about 200 nm. The modified apolipoprotein fragment of the nanoparticle may contain at least one amino acid residue which is chemically or enzymatically modified. The modified apolipoprotein fragment may be an oxidized apolipoprotein fragment. The oxidized apolipoprotein fragment may contain at least one amino acid residue which is oxidized. The oxidized residue may be a methionine. The modified apolipoprotein fragment may contain at least one amino acid residue which is oxidized, halogenated, or nitrated. The modified apolipoprotein fragment may include an amphipathic apolipoprotein fragment. The modified apolipoprotein fragment may include a modified fragment of apolipoprotein A-I, A-II, A-IV, B, C-I, C-II, C-III, or E or combinations thereof. In yet another embodiment, the synthetic nanoparticle may comprise a targeting moiety to enhance the targeting efficacy of the therapeutic agent. The targeting moiety may include a protein, a polypeptide, an antibody, a receptor, a ligand, a peptidomimetic agent, an aptamer or a product of phage display. In still another aspect, the synthetic nanoparticle may comprise a therapeutic agent selected from the group anticancer, antibacterial, antiviral, autoimmune, anti-inflammatory and cardiovascular agents, antioxidants, therapeutic peptides and combinations thereof. The therapeutic agent may also be selected from the group comprising paclitaxel, valrubicin, doxorubicin, taxotere, campotechin, etoposide, and any combination thereof. The therapeutic agent may also comprise therapeutic peptides (including but not limited to the therapeutic peptides disclosed in U.S. Pat. Nos. 8,278,271; 8,513,185; 8,614,188; 9,981,004; 10,138,276; and 10,538,558) and combinations thereof. The lipid of the synthetic nanoparticle may include cholesterol, a cholesteryl ester, a phospholipid, a glycolipid, a sphingolipid, a cationic lipid, a diacylglycerol, or a triacylglycerol. And further, the phospholipid may include phosphatidylcholine (PC), phosphatidylethanolamine (PE), phosphatidyl serine (PS), phosphatidylinositol (PI), phosphatidylglycerol (PG), cardiolipin (CL), sphingomyelin (SM), or phosphatidic acid (PA). And even further, the cationic lipid can be 1,2-dioleoyl-3-trimethylammonium-propane (DOTAP). The lipid of the synthetic nanoparticle may be polyethylene glycol(PEG)y-lated.

The disclosure further provides for a method of making a synthetic nanoparticle. The method comprises co-dissolving a predetermined amount of a mixture of neutral and/or charged lipids with a predetermined amount of a therapeutic agent and a predetermined amount of modified apolipoprotein fragment or combination of modified apolipoprotein fragments. The co-dissolving is conducted for a time period sufficient to allow the mixture to coalesce into structures whereby particles are formed incorporating the therapeutic agent. The method further comprises isolating structures that have a size of between about 5 to about 200 nm diameter. The lipid of the method may include PC, PE, PS, PI, PG, CL, SM, DOTAP or PA. The modified apolipoprotein fragment of the method may include synthetic modified apolipoprotein fragments of apo A-I, A-II, A-IV, B, C-I, C-II, C-III, or E.

The disclosure also provided for a method of making a synthetic nanoparticle comprising co-dissolving a predetermined amount of a mixture of neutral and/or charged lipids with a predetermined amount of cholesterol, a predetermined amount of HDL core lipids comprising triglycerides and/or cholesteryl ester, and a predetermined amount of a therapeutic agent. The method further comprises drying the mixture under nitrogen. The method even further comprises co-dissolving the dried mixture of with a predetermined amount of sodium cholate and a predetermined amount of modified apolipoprotein fragment. The co-dissolving is conducted for a time period sufficient to allow the components to coalesce into structures. The method still further comprises removing sodium cholate from the mixture, and isolating structures that have a size of between about 5 to about 200 nm diameter. The lipid of the method may include PC, PE, PS, PI, PG, CL, SM, DOTAP, or PA. The modified apolipoprotein fragment of the method may include modified apolipoprotein fragment of A-I, A-II, A-IV, B, C-I, C-II, C-III, or E or combination thereof.

The disclosure also provides for a method of generating a therapeutic agent-incorporated synthetic nanoparticle. The method comprises co-dissolving a predetermined amount of a lipid with a predetermined amount of cholesterol, a predetermined amount of modified apolipoprotein fragment, and a predetermined amount of a therapeutic agent. The co-dissolving is conducted for a time period sufficient to allow the mixture to coalesce into structures whereby particles are formed incorporating the therapeutic agent. The method further comprises isolating structures that have a size of between about 5 to about 200 nm diameter. The lipid of the method may comprise DOTAP. The modified apolipoprotein fragment of the method may include modified fragments of apolipoprotein A-I, A-II, A-IV, B, C-I, C-II, C-III, or E or combination thereof.

The disclosure also provides for a method of treating a macrophage-related condition. The method comprises providing a composition comprising a synthetic nanoparticle of the present disclosure, a patient having at least one symptom of a disease or condition in which macrophages are involved or recruited, and administering the composition to the patient under conditions such that said one symptom is reduced. The macrophage-related condition of the method may include a heart disease, peripheral artery disease, restenosis, stroke, the cancers (e.g., sarcoma, lymphoma, leukemia, carcinoma and melanoma), bacterial infectious diseases, acquired immune deficiency syndrome (AIDS), allergic diseases, autoimmune diseases (e.g., rheumatoid arthritis, Sjogrens, scleroderma, systemic lupus erythematosus, non-specific vasculitis, Kawasaki's disease, psoriasis, type I diabetes, pemphigus vulgaris), granulomatous diseases (e.g., tuberculosis, sarcoidosis, lymphomatoid granulomatosis, Wegener's granulomatosus), Gaucher's disease, inflammatory diseases (e.g., sepsis, inflammatory lung diseases such as interstitial pneumonitis and asthma, inflammatory bowel disease such as Crohn's disease, and inflammatory arthritis), and transplant (e.g., heart/lung transplants) rejection reactions.

The disclosure further provides for a method of treating an autoimmune disease wherein the autoimmune disease is one or more of diabetes mellitus, rheumatoid arthritis, multiple sclerosis, systemic lupus erythematosis, myasthenia gravis, scleroderma, Crohn's disease, ulcerative colitis, biliary cirrhosis, chronic active hepatitis, Hashimoto's thyroiditis, Graves' disease, Sjogren's syndrome, polyendocrine failure, vitiligo, peripheral neuropathy, rejection of transplantation, graft-versus-host disease, autoimmune polyglandular syndrome type I, acute glomerulonephritis, Addison's disease, adult-onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barre syndrome, hemochromatosis, Henoch-Schonlein purpura, idiopathic IgA nephropathy, juvenile rheumatoid arthritis, Lambert-Eaton syndrome, linear IgA dermatosis, myocarditis, narcolepsy, necrotizing vasculitis, neonatal lupus erythematosus (NLE) syndrome, nephrotic syndrome, pemphigoid, pemphigus, polymyositis, primary sclerosing cholangitis, psoriasis, rapidly-progressive glomerulonephritis (RPGN), Reiter's syndrome, stiff-man syndrome, thyroiditis, inflammatory bowel disease, skin disorders (e.g., atopic dermatitis, psoriasis, pemphigus vulgaris), cardiovascular problems (e.g., autoimmune pericarditis) and any combination thereof.

Apolipoprotein fragments and compositions of the present invention can be made synthetically and may include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_n COOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Naturally occurring residues are divided into groups based on common side chain properties: (1) hydrophobic: norleucine, methionine (Met), Alanine (Ala), Valine (Val), Leucine (Leu), Isoleucine (Ile), Histidine (His), Tryptophan (Trp), Tyrosine (Tyr), Phenylalanine (Phe); (2) neutral hydrophilic: Cysteine (Cys), Serine (Ser), Threonine (Thr); (3) acidic/negatively charged: Aspartic acid (Asp), Glutamic acid (Glu); (4) basic: Asparagine (Asn), Glutamine (Gln), Histidine (His), Lysine (Lys), Arginine (Arg); (5) residues that influence chain orientation: Glycine (Gly), Proline (Pro); (6) aromatic: Tryptophan (Trp), Tyrosine (Tyr), Phenylalanine (Phe), Histidine (His); (7) polar: Ser, Thr, Asn, Gln; (8) basic positively charged: Arg, Lys, His; and; 40 (9) charged: Asp, Glu, Arg, Lys, His.

Amino acid analogues may be generated by substitutional mutagenesis and retain the biological activity of the original trifunctional peptides. Examples of substitutions identified as "conservative substitutions" are shown in TABLE 1. If such substitutions result in a change not desired, then other type of substitutions, denominated "exemplary substitutions" in Table 1, or as further described herein in reference to amino acid classes, are introduced and the products screened for their capability of executing three functions.

TABLE 1

Amino Acid Substitutions

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Ara |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

In one embodiment, the preferred apolipoprotein fragments and compositions of the invention further comprise at least one modified or unmodified peptide fragment of amphipathic apolipoprotein (eg, apo A-I and apo A-II) capable upon interaction with lipid and/or lipid mixtures, to form synthetic lipopeptide particles (SLP) structures (also called herein as synthetic or recombinant high density lipoproteins (rHDLs), or as lipoprotein/lipopeptide complexes (LPCs) that can be spherical or discoidal. Sigalov. Contrast Media Mol Imaging 2014, 9:372-382; Sigalov. Int Immunopharmacol 2014, 21:208-219; Sigalov. US 20110256224; Sigalov. US 20130045161; Sigalov. US 20130039948; Shen, et al. PLoS One 2015, 10:e0143453; Shen and Sigalov. Sci Rep 2016, 6:28672; Shen and Sigalov. J Cell Mol Med 2017, 21:2524-2534; Shen and Sigalov. Mol Pharm 2017, 14:4572-4582; Rojas, et al. Biochim Biophys Acta 2018, 1864:2761-2768, Gursky. FEBS Lett 2014, Garda Future Lipidol 2007. The inclusion of an amphipathic apolipoprotein fragment sequences in the compositions of the invention further aids the ability to provide targeted delivery to the cells of interest. It further aids the ability to interact with lipids and/or lipoproteins in a bloodstream in vivo and form LP that mimic native lipoproteins (eg, high density lipoproteins, HDL). It further aids the ability to cross the blood-brain barrier (BBB), blood-retinal barrier (BRB) and blood-tissue barrier (BTB).

TABLE 2

Exemplary Apolipoprotein Fragments and Compositions

| Amino Acid Sequence | SEQ ID NO: |
|---|---|
| PYLDDFQKKWQEEM(O)ELRQKVE | 1 |
| PLGEEM(O)RDRARAHVDALRTHLA | 2 |
| PYLDDFQKKWQEEMELYRQKVE | 3 |
| PLGEEMRDRARAHVDALRTHLA | 4 |
| PYLDDFQKKWQEEM(O)ELYRQKVERGD | 5 |
| PLGEEM(O)RDRARAHVDALRTHLARGD | 6 |

TABLE 2-continued

Exemplary Apolipoprotein Fragments and Compositions

| Amino Acid Sequence | SEQ ID NO: |
|---|---|
| PYLDDFQKKWQEEMELYRQKVERGD | 7 |
| PLGEEMRDRARAHVDALRTHLARGD | 8 |
| LKLLDNWDSVTSTFSKLREQLG | 9 |
| PVTQEFWDNLEKETEGLRQEMS | 10 |
| PVTQEFWDNLEKETEGLRQEM(O)S | 11 |
| KDLEEVKAKVQ | 12 |
| PLRAELQEGARQKLHELQEKLS | 13 |
| PYSDELRQRLAARLEALKENGG | 14 |
| ARLAEYHAKATEHLSTLSEKAK | 15 |
| PALEDLRQGLL | 16 |
| PVLESFKVSFLSALEEYTKKLN | 17 |
| SLVSQYFQTVTDYGKDLMEKVK | 18 |
| SLVSQYFQTVTDYGKDLM(O)EKVK | 19 |
| SYFEKSKEQLT | 20 |
| PLIKKAGTELVNFLSYFVEL | 21 |
| GSVQTIVFQPQLASRTPTGQS | 22 |
| LKLLDNWDSVTSTFSKLREQLGRGD | 23 |
| PVTQEFWDNLEKETEGLRQEMSRGD | 24 |
| PVTQEFWDNLEKETEGLRQEM(O)SRGD | 25 |
| KDLEEVKAKVQRGD | 26 |
| PLRAELQEGARQKLHELQEKLSRGD | 27 |
| PYSDELRQRLAARLEALKENGGRGD | 28 |
| ARLAEYHAKATEHLSTLSEKAKRGD | 29 |
| PALEDLRQGLLRGD | 30 |
| PVLESFKVSFLSALEEYTKKLNRGD | 31 |
| SLVSQYFQTVTDYGKDLMEKVKRGD | 32 |
| SLVSQYFQTVTDYGKDLM(O)EKVKRGD | 33 |
| SYFEKSKEQLTRGD | 34 |
| PLIKKAGTELVNFLSYFVELRGD | 35 |
| GSVQTIVFQPQLASRTPTGQSRGD | 36 |
| SEAEDASLLSFMQGYMKH | 37 |
| SEAEDASLLSFMQGYM(O)KH | 38 |
| TAKDALSSV | 39 |
| QESQVAQQARGWV | 40 |
| FSSLKDYWSTVKDKFSEF | 41 |
| TPNVSSALEKLK | 42 |
| FGNTLDEKARDLISRIK | 43 |
| KMRDWFSDTFQKVKDKLK | 44 |

TABLE 2-continued

Exemplary Apolipoprotein Fragments and Compositions

| Amino Acid Sequence | SEQ ID NO: |
|---|---|
| KM(O)RDWFSDTFQKVKDKLK | 44 |
| TQVKESLSSYWESAKTAAQNLYEK | 45 |
| DEKLRDLYSKSTAAMSTYTGIFTDQV | 46 |
| DEKLRDLYSKSTAAM(O)STYTGIFTDQV | 47 |

Although it is not necessary to understand the mechanism of an invention, it is believed that apolipoprotein fragments of the present invention function to assist in the self-assembly of synthetic lipoprotein/lipopeptide particles (e.g., SLP or HDL) upon binding to lipid or lipid mixtures. In one embodiment, an SLP or an HDL comprises a combination of different apolipoprotein fragments. In one embodiment, the self-assembly of SLP or HDL is accompanied by encapsulation or incorporation of a therapeutic drug or agent of interest.

In one embodiment, an apolipoprotein fragment contains a modified amino acid. In one embodiment, a modified amino acid comprises sulfoxidized methionine residue. In one embodiment, the modified apolipoprotein fragment is PYLDDFQKKWQEEM(O)ELRQKVE (SEQ ID NO 1; PE22ox). See FIG. 12. In one embodiment, the PE22ox apolipoprotein fragment is derived from an apolipoprotein A-I helix 4. In one embodiment, a PE22ox apolipoprotein fragment comprises a sulfoxidized methionine residue. In one embodiment, a PE22ox apolipoprotein A-I fragment provides a targeted delivery to cells (e.g., macrophages) via interaction with a scavenger receptor (e.g., SR-A expressed on macrophages). In one embodiment, the modified apolipoprotein fragment is PLGEEM(O)RDR-ARAHVDALRTHLA (SEQ ID NO 2; PA22ox). See FIG. 12. In one embodiment, a PA22ox apolipoprotein fragment is derived from an apolipoprotein A-I helix 6. In one embodiment, a PA22ox apolipoprotein fragment comprises a sulfoxidized methionine residue. In one embodiment, a PA22ox apolipoprotein A-I fragment provides a targeted delivery to cells (e.g., macrophages) via interaction with a scavenger receptor (e.g., SR-A expressed on macrophages). In one embodiment, PA22ox interacts with a hepatocyte SR-BI binding site that induces clearance of drug-containing synthetic LPC (HDL, SLP) via interaction with SR-BI expressed on hepatocytes. In one embodiment, PA22ox provides targeted delivery to a cancer cells via interaction with a cancer cell SR-BI binding site.

Figure 13:
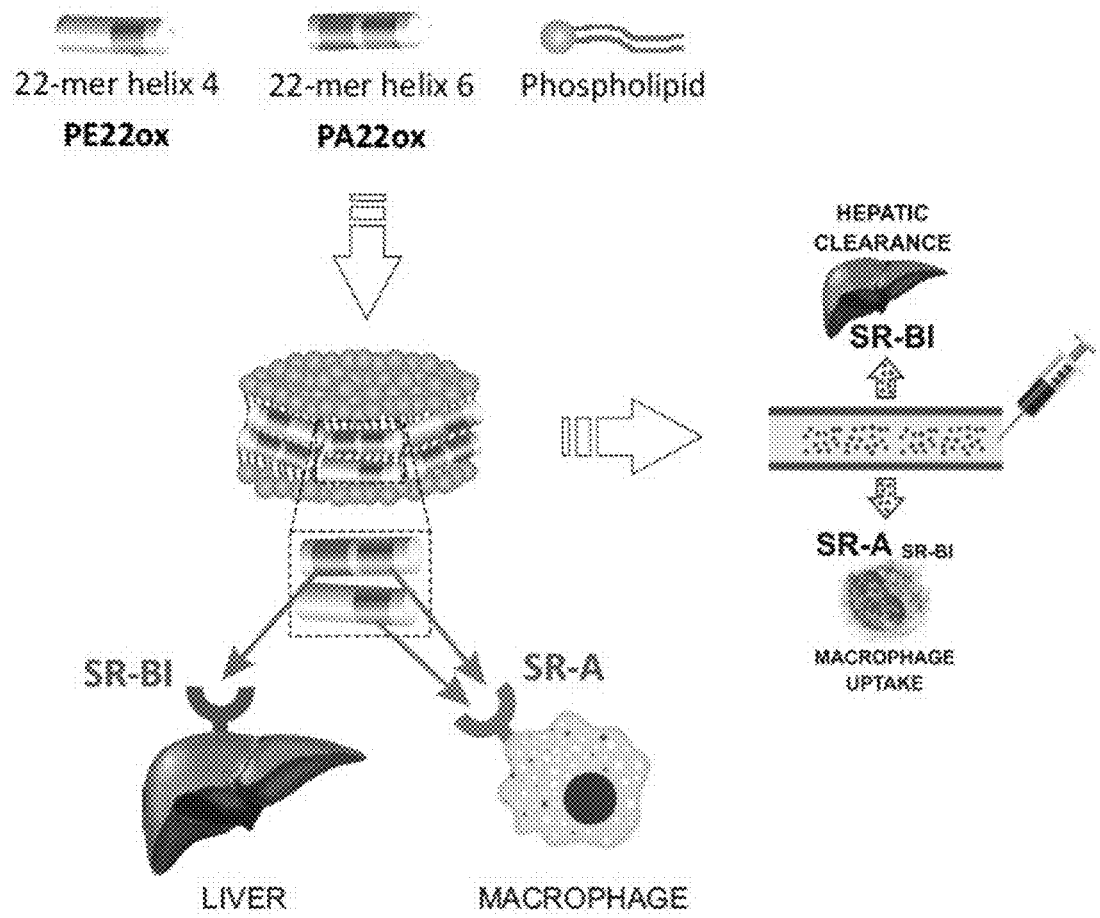
FIG. 13 presents a schematic representation of one embodiment of discoidal synthetic (recombinant) HDL (dHDL, or discoidal synthetic lipoprotein/lipopeptide particles, dSLP; or discoidal synthetic lipoprotein/lipopeptide complexes, dLPC).

In one embodiment, an apolipoprotein fragment with a modified amino acid residue targets a discoidal HDL (dHDL) particle to cells of interest (eg, macrophages). See FIG. 13. In one embodiment, the synthesized dHDL comprise a phospholipid and 1:1 equimolar mixture of PE22ox apolipoprotein A-I fragments and PA22ox apolipoprotein A-I fragments. In one embodiment, upon systemic administration, sulfoxidized methionine residues of PE22ox and PA22ox provide targeted delivery of dHDL to cells (e.g., macrophages). In one embodiment, the dHDL targeted macrophage delivery is mediated by scavenger receptor A (SR-A), in particular targeting a binding site for scavenger receptor B type I (SR-BI) to induce hepatic clearance of dHDL. In one embodiment, the synthetic (recombinant) HDL is a spherical HDL (sHDL, sLPC, or sSLP). Although it is not necessary to understand the mechanism of an invention, it is believed that targeting to macrophages by sHDLs can be mediated by scavenger receptor A (SR-A).

In one embodiment, an apolipoprotein fragment contains an epitope that binds to a cell surface receptor. In one embodiment, the epitope binds to a scavenger receptor B type I (SRBI). In one embodiment, an apolipoprotein fragment comprising an SRBI epitope comprises PA22

(PLGEEMRDRARAHVDALRTHLA, SEQ ID NO 4).

In one embodiment, an apolipoprotein fragment with an epitope that binds to SRBI targets an SLP (e.g., HDL) particle to a cell of interest including, but not limited to, hepatocytes, macrophages or cancer cells. In one embodiment, an apolipoprotein fragment comprises a modified amino acid residue and an SRBI epitope. In one embodiment, an apolipoprotein fragment that comprises a modified amino acid residue and an SRBI epitope is PA22ox (PLGEEM(O)RDRARAHVDALRTHLA; SEQ ID NO 2).

Figure 14:
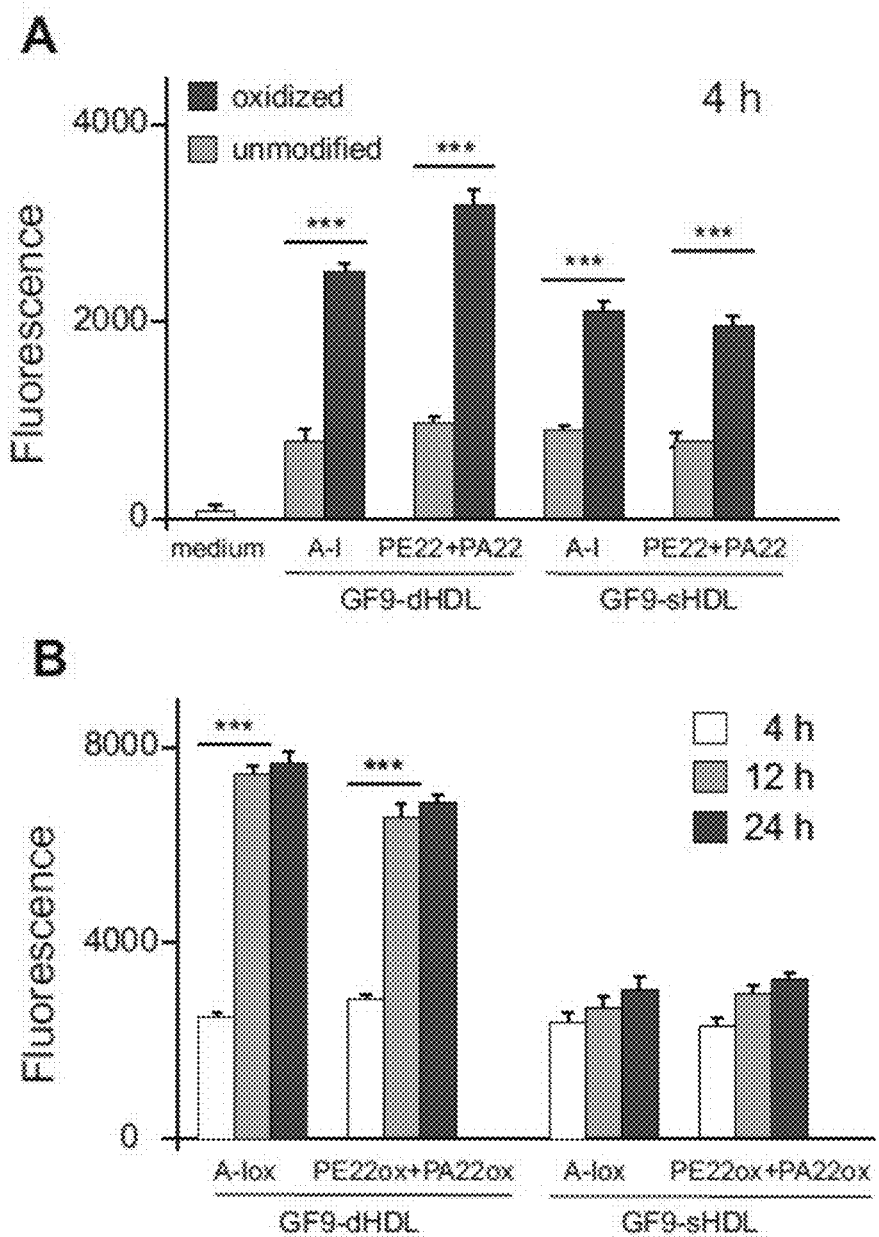
FIG. 14 presents exemplary data showing that in drug-containing synthetic (recombinant) HDL (SLP, LPC), apolipoprotein can be replaced by synthetic apolipoprotein fragments without compromising HDL activity in macrophage uptake assay.

In one embodiment, an apo A-I peptide fragment (e.g., PA22 or PE22) comprise oxidized methionine residues. The data presented herein shows that oxidized apo A-I fragments enhance in vitro macrophage uptake of an rHDL. See, FIG. 14. The rHDLs comprising oxidized apo A-I fragments were synthesized by using an equimolar (1:1) mixture of PA22ox and PE22ox to an extent similar to that observed for rHDLs synthesized by using oxidized human full length apo A-I protein as disclosed herein. These data show that oxidation of methionine residues of native human apo A-I protein or synthetic apo A-I peptide fragments PA22 and PE22 enhances in vitro macrophage uptake of HDL synthesized by using either apo A-I or an equimolar (1:1) mixture of PA22 and PE22. In one embodiment, an oxidized apo A-I peptide fragment rHDL comprises an encapsulated or incorporated therapeutic drug and a TREM-1 inhibitory peptide GF9 (GF9-HDL).

In one embodiment, the compositions of the present invention are used to deliver the triggering receptor expressed on myeloid cells (TREM-1) inhibitory peptide sequence. In one embodiment, the TREM-1 inhibitory peptide sequence is GF9 (GLRILLLKV) (SEQ ID NO: 48); LR12 (LQEEDAGEYGCM) (SEQ ID NO: 49) or LP17 (LQVTDSGLYRCVIYHPP) (SEQ ID NO: 50). Sigalov (2014); Rojas et al. (2017); Shen and Sigalov (2017); U.S. Pat. Nos. 8,513,185; 9,981,004; Gibot, et al. Infect Immun (2006) 74:2823-2830; Gibot, et al. Shock (2009) 32:633-637; Gibot, et al. Eur J Immunol (2007) 37:456-466; Joffre, et al. J Am Coll Cardiol (2016) 68:2776-2793; Cuvier, et al. Br J Clin Pharmacol (2018); Zhou, et al. Int Immunopharmacol (2013) 17:155-161; Faure, et al., U.S. Pat. No. 8,013,116; Faure, et al., U.S. Pat. No. 9,273,111; Gibot, et al., 10 U.S. Pat. No. 9,657,081; Gibot and Derive, U.S. Pat. No. 9,815,883; and Gibot and Derive, U.S. Pat. No. 9,255,136).

Figure 15:
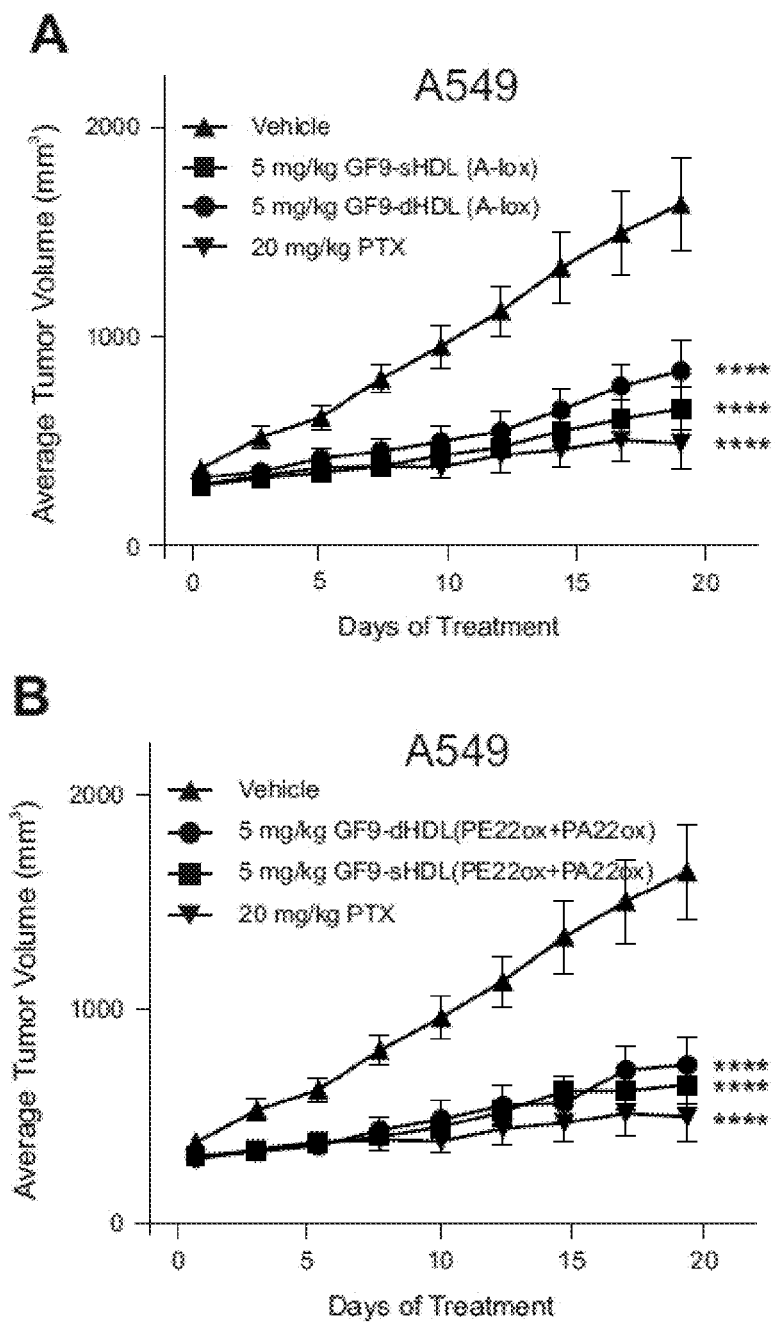
FIG. 15 presents exemplary data showing that in drug-containing synthetic (recombinant) HDL (SLP, LPC), apolipoprotein can be replaced by synthetic apolipoprotein fragments without compromising the drug antitumor activity in an animal model. ****, P<0.0001. Abbreviations: apo, apolipoprotein; HDL, high density lipoproteins; HDL (A-Iox), HDL with oxidized human apo A-I; HDL (PE22ox+PA22ox), HDL with a 1:1 mixture of synthetic peptides PE22ox and PA22ox that correspond to apo A-I helixes 4 and 6, respectively (SEE FIG. 12); dHDL and sHDL, discoidal and spherical HDL, respectively; LPC, lipoprotein/lipopeptide complexes; NSCLC, non-small cell lung cancer; PTX, paclitaxel; SLP, synthetic lipoprotein/lipopeptide particles; TREM-1, triggering receptor expressed on myeloid cells-1.

The data presented herein demonstrate that a GF9 peptide encapsulated within a macrophage-targeted HDL comprising an equimolar mixture of oxidized apo A-I synthetic fragments PE22 and PA22 (PE22ox and PA22ox, respectively) inhibits tumor growth and was well-tolerated in and in the A549 xenograft mouse model (NSCLC). These data show a tumor inhibition that is similar to that observed for a GF9 peptide incorporated in an oxidized human full length apo A-I protein HDL (A-lox). See, FIGS. 15 and 16. Here, A549 cells were injected subcutaneously into nude mice and randomized into treatment groups (n=10) once tumors reached an average of 200 mm$^3$. The treatment groups were: i) Vehicle (HDL containing no GF9); ii) paclitaxel (PTX) as a positive control; iii) GF9-dHDL (A-Iox); iv) GF9-sHDL (A-Iox); v) GF9-dHDL(PE22ox+PA22ox); and vi) GF9-sHDL(PE22ox+PA22ox) where each group received intraperitoneal injections twice a week. For statistical analysis, each treatment was compared with the vehicle control using repeated measures ANOVA followed by Bonferroni test. See, FIG. 15. Post necropsy excised tumors weights were averaged from mice in each group treated with PTX (positive control) and GF9-HDL that contain either oxidized full length apo A-I protein (A-Iox) or oxidized apo A-I synthetic fragments PE22 and PA22 (PE22ox and PA22ox, respectively) were significantly lower compared to the vehicle-treated group. See, FIG. 16. These data suggest that a full length oxidized apolipoprotein molecule can be replaced by an oxidized apolipoprotein fragment without compromising antitumor GF9-HDL activity.

The data presented herein demonstrate that a GF9 peptide encapsulated within a macrophage-targeted HDL comprising an equimolar mixture of oxidized apo A-I synthetic fragments PE22 and PA22 (PE22ox and PA22ox, respectively) extends LPS-induced septic shock survival and was well-tolerated in mice. The data show survival curves that were similar to that observed for a GF9 peptide incorporated in an oxidized human full length apo A-I protein HDL. See, FIG. 17. These data show that a TREM-1 inhibitory peptide GF9 incorporated into a synthetic (recombinant) macrophage-targeted oxidized full length human apo A-I protein (A-lox) HDL or a macrophage-targeted HDL comprising an equimolar mixture of apo A-I peptide fragments (e.g., PE22ox and PA22ox) similarly prolong survival of mice with LPS-induced septic shock. It should be noted that free GF9 (5 mg/kg dose) has no effect on LPS-induced septic shock survival suggesting that targeted delivery of the same dose of GF9 by using HDL with 1:1 PE22ox:PA22ox increases the therapeutic activity of GF9. This suggests that a full length apolipoprotein peptide can be replaced by apolipoprotein fragments without compromising GF9-HDL therapeutic activity in the animal model of sepsis.

The data presented herein show that a GF9 peptide encapsulated into a macrophage-targeted HDL comprising an equimolar mixture of oxidized apo A-I synthetic fragments PE22 and PA22 (PE22ox and PA22ox, respectively) inhibits pancreatic cancer tumor growth and was well-tolerated in a xenograft mouse model. After tumors in AsPC-1-, BxPC-3-, or Capan-1-bearing mice reached a volume of 150-200 mm$^3$, mice were randomized into treatment groups and intraperitoneally (ip) administered once daily 5 times per week (5qw). The treatment groups were: i) Vehicle; ii) Free GF9; iii) GF9-dHDL(PE22ox+PA22ox); and iv) GF9-sHDL These data showed 10-fold reduction in an effective GF9 peptide dose between free GF9 and GF9-HDL(PE22ox+PA22ox) (i.e., 25 mg/kg vs. 2.5 mg/kg). See, FIG. 18. The data show that treatment with either free GF9 or GF9-HDL(PE22ox+PA22ox) suppresses tumor growth in experimental pancreatic cancer without affecting body weight. This suggests that targeted delivery of GF9 can be provided by rHDLs comprising apolipoprotein fragments to treat pancreatic cancer.

In one embodiment, the compositions of the present invention are used to deliver the T cell receptor (TCR) inhibitory peptide sequence. In one embodiment, the TCR inhibitory peptide sequence is MG11 (MWKTPTLKYFG) (SEQ ID NO: 51). Shen and Sigalov (2016).

The data herein demonstrate that a MG11 peptide encapsulated by a macrophage-targeted sHDL comprising an equimolar mixture of oxidized apo A-I synthetic fragments PE22 and PA22 (PE22ox and PA22ox, respectively) exhibited significant antiarthritic activity and was well-tolerated in a rheumatoid arthritis animal model. This data shows a 10-fold reduction in effective MG11 dose by MG11-sHDL (PE22ox:PA22ox) as compared to a free MG11 peptide (25 mg/kg free MG11 vs. 2.5 mg/kg MG11-sHDL(PE22ox+PA22ox). See, FIG. 19. Treatment with either free MG11 (e.g., MWKTPTLKYFG) (SEQ ID NO: 51) or an MG11-sHDL(PE22ox and PA22ox) strikingly ameliorates clinical severity of CIA in mice without affecting body weight. In contrast, free control peptide MG11-2G (e.g., MWGTPTLGYFG) (SEQ ID NO: 52) has no effect on disease severity as compared to vehicle-treated CIA mice. This suggests that targeted delivery of MG11 can be provided by rHDLs comprising apolipoprotein fragments to treat arthritis.

The data presented herein show that an MG11 peptide encapsulated within a macrophage-targeted HDL comprising an equimolar mixture of oxidized apo A-I synthetic fragments PE22 and PA22 (PE22ox and PA22ox, respectively) significantly reduces serum cytokine releases in a rheumatoid arthritis animal model. The data show a 10-fold reduction in effective MG11 peptide dose with MG11-HDL (PE22ox:PA22ox) as compared to a free MG11 peptide (25 mg/kg free MG11 vs. 2.5 mg/kg MG11-sHDL(PE22ox+PA22ox). See, FIG. 20. Treatment with free MG11 (e.g., MWKTPTLKYFG) (SEQ ID NO: 51) or a MG11-HDL (PE22ox and PA22ox) significantly reduced serum cytokine release in mice with CIA. In contrast, a free control peptide MG11-2G (e.g., MWGTPTLGYFG) (SEQ ID NO: 52) had no effect on the serum cytokine release as compared to vehicle-treated CIA mice. This suggests that targeted delivery of MG11 can be provided by HDL with synthetic apolipoprotein fragments to treat arthritis conditions.

Although it is not necessary to understand the mechanism of an invention, it is believed that the rHDL particles and compositions of the present invention may cross the blood brain barrier (BBB), blood retinal barrier (BRB) and blood tumor barrier (BTB), thus delivering the incorporated therapeutic agents to areas of interest in the brain, retina and tumor. As such, in one embodiment, the particles and compositions of the present invention can be used to formulate the drug to treat and/or prevent diseases and conditions, where delivery of the drug to the brain, retina and/or tumor is needed.

F. Clinical Applications

This is especially important for anticancer chemotherapeutic agents most of which are lipophilic and thus cannot be administered by themselves as pure chemicals. These agents have to be included in biocompatible formulations to enhance solubility, increase circulatory residence time of the therapeutic agent, minimize the undesirable side effects and to alleviate drug resistance.

Because of the leading position of cancer as a cause of mortality in industrialized societies, applications in this area are thus highlighted. However, it should be noted that the techniques and compositions listed and described below are applicable to a broad range of disease states including, but not limiting to, cardiovascular disease, bacterial infectious diseases, diabetes, and autoimmune diseases. Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

1. Cancer

As well-known in the art and described in US Pat Appl 20090110739, most anticancer chemotherapeutic agents cannot be administered by themselves as pure chemicals but have to be included in biocompatible formulations to enhance solubility, increase circulatory residence time of the therapeutic agent (TA), minimize the undesirable side effects and alleviate drug resistance Despite advances in chemotherapy, cancer is one of the major causes of mortality in the United States, and the worldwide incidence of cancer continues to increase. Breast cancer remains the most common non-skin cancer and the leading cause of death in women. There is an unmet clinical need for an effective treatment of cancer.

The infiltrate of most tumors contains tumor-associated macrophages (TAMs) that are derived from circulating monocytic precursors and are directed into the tumor by chemokines. Macrophages are prominent in the stromal compartment of virtually all types of malignancy and play an important role in tumor growth and metastasis. They secret a variety of growth factors, cytokines, chemokines, and enzymes that regulate tumor growth, angiogenesis, invasion, and metastasis. There is a significant positive correlation between high vascular grade and increased macrophage index, and a strong relationship is observed between increased macrophage counts and reduced relapse-free survival and reduced overall survival as an independent prognostic variable in cancer patients. The increased tumor islet macrophage density confers a marked survival advantage, whereas increased number of macrophages in the tumor stroma is associated with poor prognosis in lung cancer. Importantly, paclitaxel (PTX), a mitotic inhibitor widely used in cancer chemotherapy, induces TAM production of interleukin-12, a cytokine known to induce tumor regression and cure in animal model systems. Thus, the critical feature of PTX as an anticancer agent may not be only its microtubule-stabilizing activity, but also its ability to stimulate release of anticancer cytokines from TAMs. Also, targeting tumor-associated fibroblasts is known to improve cancer chemotherapy by increasing intratumoral drug uptake. Collectively, these data support targeting TAMs as a novel strategy of not only cancer imaging but also therapy of cancer.

2. Atherosclerosis and Restenosis

Despite advances in cardiovascular care, atherosclerosis, the buildup of plaque in the artery walls, remains the leading cause of death in the United States. Inflammation has a crucial role at all stages of atherosclerosis. Macrophages are involved in the formation, progression, and pathogenicity of atherosclerotic plaques. Further, after percutaneous coronary interventions (angioplasty or stent implantation), restenosis remains to be a problem in clinical cardiology. In this field, nanoparticle technology is regarded as a promising approach to deliver antiproliferative and antiremodeling drugs at the site of injury. Thus, in atherosclerosis and restenosis, macrophages are an attractive target for delivery of not only imaging agents (PCT Pat Appl PCT/US10/52117) but also therapeutics (US Pat Appl 20060257466 and U.S. Pat. No. 7,740,854).

3. Microbial Infections

In microbial infections, macrophage-specific delivery systems are particularly attractive because macrophages act as host cells for many parasites, bacteria and viruses that give rise to the outbreak of so many deadly diseases. Besides the advent of other classical drugs carriers, polymeric nanoparticles have been explored for their effective use in experimental infectious diseases upon macrophage targeting.

For example, in acquired immune deficiency syndrome (AIDS) therapy, macrophages could be targeted since they represent a cell population of the reticuloendothelial system (RES) that plays a role in the immunopathogenesis of a disease. Increasing drug concentrations at specific sites where macrophages are abundant may allow a reduction in the dosage and, as a result, a decrease in systemic toxicity.

G. Methods of Using Lipoprotein Fragment Delivery Particles

The invention describes approaches for administering a pharmaceutical agent to an individual. The methods of the invention include preparing and administering a delivery particle as described above that includes the synthetic lipoprotein particle and a drug that is attached to said nanoparticle (FIGS. 1, 2A and 2B). Optionally, therapeutically effective amounts of the delivery particles are administered, in a pharmaceutically acceptable formulation.

The route of administration of the drug, attached to the carrier particle, may vary according to the nature of the pharmaceutical agent to be administered or the condition to be treated. For mammals, the administration is generally parenteral. Routes of administration include, but are not limited to intravenous, intramuscular, subcutaneous, transmucosal, and transdermal. Delivery particles may also be formulated for controlled release. The term "controlled release" as used herein refers to release of a drug from the carrier particle so that the blood or tissue levels of the pharmaceutical is maintained within the desired therapeutic range for an extended period (hours or days).

In one embodiment, the invention provides a method for treating cancer in an individual. The method includes administering a therapeutically effective amount of a chemotherapeutic agent attached to the delivery particles as described above (see also FIGS. 1, 2A and 2B) in a pharmaceutically acceptable formulation. In one embodiment, the agent is paclitaxel.

In particular embodiments, the compositions of the present invention comprising therapeutic and imaging agents or combination of these agents may be used to assess the efficacy or dosing of a particular existing drug. For example, in the case of atherosclerosis, the atherosclerotic lesion size or composition may be monitored prior to and after the administration of a given drug treatment to assess whether the treatment is effective at reducing the size or composition of a lesion.

In particularly preferred embodiments, the compositions of the present invention can be used for targeting macrophages in treating macrophage-related diseases (US Pat Appl 20010002251 and U.S. Pat. No. 7,740,854) including, but not limiting to, the cancers (sarcoma, lymphoma, leukemia, carcinoma and melanoma), bacterial infectious diseases, AIDS, cardiovascular diseases (e.g., arteriosclerosis, atherosclerosis, intimal hyperplasia and restenosis) and other macrophage-related disorders including autoimmune diseases (e.g., rheumatoid arthritis, Sjogrens, scleroderma, systemic lupus erythematosus, non-specific vasculitis, Kawasaki's disease, psoriasis, type I diabetes, pemphigus vulgaris), granulomatous diseases (e.g., tuberculosis, sarcoidosis, lymphomatoid granulomatosis, Wegener's granulomatosus), Gaucher's disease, inflammatory diseases (e.g., sepsis, inflammatory lung diseases such as interstitial pneumonitis and asthma, inflammatory bowel disease such as Crohn's disease, and inflammatory arthritis), and in transplant rejection (e.g., in heart/lung transplants). Examples of macrophage-related diseases are also macrophage-related pulmonary diseases such as emphysema (see e.g., US Pat Appl 20050281740).

H. Kits

The individual components of the rHDL compositions of the present invention may be provided in a kit, which kit may further include instructions for formulating and/or using the therapeutic agents of the invention. Such a kit will comprise a first composition comprising a therapeutic agent, a second composition comprising modified apolipoproteins A-I and A-II and/or fragments thereof, and a third composition comprising a free phospholipid. The kit may further comprise a fourth composition comprising a sterol (e.g., cholesterol). The kit may optionally comprise a fifth composition comprising HDL core lipids (e.g., cholesteryl ester, and TG). The kit may still further comprise a sixth composition comprising imaging agents prepared and characterized as disclosed in PCT Pat Appl PCT/US10/52117. The kit also may comprise a device for delivering the composition to a mammal.

EXPERIMENTAL

The following non-limiting Examples are put forth so as to provide those of ordinary skill in the art with illustrative embodiments as to how the compounds, compositions, articles, devices, and/or methods claimed herein are made and evaluated. The Examples are intended to be purely exemplary of the invention and are not intended to limit the scope of what the inventor regard as his invention. Efforts have been made to ensure accuracy with respect to numbers (e.g., amounts, temperature, etc.) but some errors and deviations should be accounted for.

Standard methods of isolation, synthesis, modification, purification, and characterization of the major protein constituents of the synthetic HDL and HDL-like compositions of the present inventions, the unmodified and modified apo A-I and A-II as well as peptide fragments thereof, are well-known in the art (see e.g., PCT Pat Appl PCT/US10/52117).

Example 1

Methods of Reconstitution and Characterization of Reconstituted HDL

As described in Oda et al. J Lipid Res 2006; 47:260-7 and disclosed in PCT Pat Appl PCT/US10/52117, U.S. Pat. Nos. 6,306,433, 7,824,709 and 6,514,523; US Pat Apps 20090110739 and 20070243136, the standard methods well known in the art can be used to reconstitute HDL as spherical or discoidal particles using the purified apo A-I and A-II as well as peptide fragments thereof, lipids and therapeutic and/or imaging agents. The standard procedures of HDL purification and characterization are also well-known in the art. It should be understood by those of ordinary skill in the art that any of the purified unmodified and modified apo A-I and A-II as well as peptide fragments thereof described herein and in PCT Pat Appl PCT/US10/52117 can be used to produce the compositions of the present invention. However, it is critical for the rHDL of the invention that the rHDL prepared should contain at least one modified molecule of apo A-I and/or apo A-II and/or fragments thereof.

In one embodiment, the homogeneous discoidal rHDL with or without naturally occurring oxidized apo A-I containing methionine sulfoxides at positions 112 and 148 as referred to the apo A-I primary sequences can be prepared using the standard sodium cholate dialysis method well known in the art (see e.g., US Pat Appl 20090110739 and PCT Pat Appl PCT/US10/52117). This method allows to prepare rHDL with 2 or 3 apo A-I per particle and 9-11 nm diameter. Reconstituted discoidal HDL can be characterized using the standard methods (see e.g., U.S. Pat. No. 7,824,709 and PCT Pat Appl PCT/US10/52117). Exemplary FIGS. 6, 7, 8, 10, and 11 show the results of structural, compositional, and functional analysis of such rHDL.

Oxidative damage to apo A-I in the context of rHDL can be reversed by PMSR in the presence of a source of reducing equivalents (see e.g., PCT Pat Appl PCT/US10/52117). In specific embodiments, the rHDL and HDL-like compositions of the present invention that contain apolipoproteins or fragments thereof with sulfoxidized methionine residues may further contain DHLA to reverse this oxidative modification at sites of interest. Although it is not necessary to understand the mechanism of an invention, it is believed that at sites of interest, DHLA serves as a cofactor for PMSR enzyme to reduce methionine sulfoxides back to their native form.

Example 2

Production of Lipoprotein Apolipoprotein A-1 (LpA-I)-Therapeutic Agent Complexes Preparation of Spherical LpA-I-Paclitaxel Complexes As disclosed in US Pat Appl 20090110739, the particles are prepared by a process involving cholate dialysis to produce a spherical structure with the pharmaceutical enclosed in the interior hydrophobic core region. The lipid mixture (egg yolk phosphatidylcholine (PC), cholesterol and cholesteryl oleate in the ratio of 3.8:1:88.5) and 2 mg paclitaxel (PTX) is dried under nitrogen gas to a thin film and dispersed in dimethylsulfoxide and subsequently in 1.4 ml of 10 mM Tris, 0.1 M KCl, 1 mM EDTA, pH 8.0). Then, 140 ul of sodium cholate (100 mg/ml stock in [0.15 M NaCl 0.003 M KCl, 0.15 M potassium phosphate, pH 7.4, designated as PBS, phosphate buffered saline]) is added to produce mixtures with a final PC to cholate molar ratio of ~1:1.6. Apo A-I (12.7 mg/ml) in 0.4 ml of PBS is added to this mixture and the final volume is adjusted to 2 ml with PBS. The lipid/protein/cholate mixture is then incubated for 12 hrs at 4° C., followed by dialysis (2 liter of PBS, for two days) with three buffer changes. Using $^3$H-cholate as a tracer, <2% of the cholate remains in the LpA-I-PTX preparations. Over 60% of the PTX remains associated with the LpA-I delivery particles as a result of this process. In another embodiment, the spherical LpA-I particles are prepared employing other methods well-known in the art and disclosed in U.S. Pat. No. 6,514,523 and PCT Pat Appl PCT/US10/52117. The obtained particles are purified and characterized using density gradient ultracentrifugation, gel exclusion chromatography, ultraviolet/visible absorbance spectroscopy, gradient gel electrophoresis, electron microscopy, and other standard methods well-known in the art and disclosed in U.S. Pat. No. 6,514,523, US Pat Appl 20090110739, and PCT Pat Appl PCT/US10/52117.

Preparation of Discoidal LpA-I-Amphotericin B Complexes

As described in Oda et al. J Lipid Res 2006; 47:260-7 and disclosed in U.S. Pat. No. 7,824,709, 7 mg of dimyristoylphosphatidylcholine (DMPC) and 3 mg of dimyristoylphosphatidylglycerol (DMPG) are dissolved in chloroform-methanol (3:1, v/v) and dried under a stream of nitrogen gas, coating the vessel wall with the phospholipid. The tube is then lyophilized for a minimum of 2 h to remove residual organic solvent. After this, the lipids are dispersed in 1 ml of PBS (20 mM sodium phosphate, pH 7.0, and 150 mM sodium chloride) by vortexing. To the dispersed lipid, 2.5 mg of amphotericin B (AMB) from a stock solution (30 mg/ml in dimethylsulfoxide (DMSO) is added. Subsequently, 4 mg of apo A-I in 2.0 ml of PBS is added, and the solution (3.1 ml final volume) is incubated at 24° C. The addition of apo A-I leads to a time-dependent decrease in sample turbidity, consistent with the formation of discoidal LpA-I-AMB particles. Full sample clarity is achieved by mild bath sonication (30 s to several minutes). The solution is dialyzed overnight against PBS to remove DMSO and filter-sterilized before use. In another embodiment, the discoidal LpA-I particles are prepared, purified, and characterized employing the methods well-known in the art (see e.g., U.S. Pat. No. 6,514,523 and PCT Pat Appl PCT/US10/52117). The obtained particles are purified and characterized using density gradient ultracentrifugation, gel exclusion chromatography, ultraviolet/visible absorbance spectroscopy, gradient gel electrophoresis, electron microscopy, and other standard methods well-known in the art (see e.g., U.S. Pat. Nos. 7,824,709 and 6,514,523, US Pat Appl 20090110739, and PCT Pat Appl PCT/US10/52117).

Preparation of Lipoprotein-Like Liposomes

As well-known in the art and discussed herein and in PCT Pat Appl PCT/US10/52117, US Pat U.S. Pat. Nos. 5,676,926; 7,288,266, 7,588,751, 6,248,353, 6,139,819, 5,676,928, and 5,965,542, US Pat Appls 20070065432, 20060204566, 20090012025, 20080286353, 20090311191, and 20090312402, highly efficient charged liposomes can be used as an improved delivery system for therapeutic and contrast agents. Example is PTX which can be encapsulated into cationic liposomes and used to inhibit tumor growth (PCT Pat Appl PCT/US10/52117). As discussed herein and disclosed in PCT Pat Appl PCT/US10/52117 and U.S. Pat. No. 6,248,353, proteins can be easily incorporated into liposomes by incubating the protein solution with the solution of preformed liposomes. To incorporate therapeutic agents including, but not limiting to, anticancer, antiviral, autoimmune and antibacterial agents, cardiovascular agents, anti-inflammatory therapeutics, and antioxidants (e.g., LA and DHLA), standard methods described herein and well-known in the art (see e.g., PCT Pat Appl PCT/US10/52117 and U.S. Pat. No. 6,248,353) can be applied by those of ordinary skill in the art of drug delivery and liposome and lipoprotein formulations. These methods comprise attaching the therapeutics to nanoparticle by adsorption, incorporation, covalent bonding, chelating, and encapsulation. The choice of methods for attachment is practiced by those of ordinary skill in the art of drug delivery and formulations.

As disclosed herein and in PCT Pat Appl PCT/US10/52117, modified apo A-I and A-II and fragments thereof can be easily incorporated in the liposome-based therapeutic and/or contrast agent by incubating the protein or peptide solution with the solution of preformed liposomes. The modified apo A-I and A-II and fragments thereof of the present invention facilitate the targeted delivery and retention of the nanoparticles containing the therapeutic agent to macrophage-rich sites of interest, including but not limiting to, tumor sites and atherosclerotic plaques. This provides a way to increase drug concentrations at specific sites where macrophages are abundant that may allow a reduction in the dosage and, as a result, a decrease in systemic toxicity.

The present example describes methods of preparation of lipoprotein-like liposomes to create the nanoparticles for delivery of therapeutic agents. As described in Kim et al. J Hepatol 2009; 50:479-88, 1,2-dioleoyl-3-trimethylammonium-propane (DOTAP)/cholesterol/apo A-I compositions can be prepared and used for incorporation and delivery of therapeutic agents. Cationic liposomes are prepared by mixing DOTAP and cholesterol in a molar ratio of 1:1. To formulate apo A-I-bound liposomes, cationic liposomes are incubated with apo A-I at a lipid/protein ratio of 10:1 (w/w) overnight at 4° C. The incorporation yield of apo A-I into liposomes is examined by labeling of the lipid component with lissamine rhodamine B-diacyl phosphatidylethanolamine (Rho-PE). The labeled self-assembled Rho-PE/DOTAP/cholesterol/apo A-I liposomes are loaded onto a Sepharose CL-4B column, and both fluorescence intensity and protein concentration are measured in each eluted fraction. DOTAP/cholesterol/apo A-I are used for encapsulation of siRNA and intravenously administered in mice with hepatitis C virus to assess antiviral activity as well as the duration of silencing. The results suggest that DOTAP/cholesterol/apo A-I liposome is a highly potential delivery vehicle to transfer therapeutic agents.

Example 3

Use of Spherical LpA-I-Paclitaxel Complexes

Cytotoxicity

As disclosed in US Pat Appl 20090110739, the cytotoxic effect of the LpA-I-PTX preparations on cancer cells can be assessed by the methyl thiazol tetrazolium (MTT) assay. Briefly, cells are plated in 96-well plates (5000 cells/well) in their respective media. Next day, the monolayers are washed with PBS (pH 7.4) twice, and then incubated at 37° C. for 24 h with the LpA-I-PTX complexes in serum-free media. The following day, 25 ml of MTT (1 mg/ml) is added to each well and incubated for 3 h at 37° C. Plates are centrifuged at 1200 rpm for 5 min. The medium is removed, the precipitates are dissolved in 200 ml of DMSO and the samples are read at 540 nm in a microtiter plate reader.

Animal Toxicity

As disclosed in US Pat Appl 20090110739, female C57BL6 mice (6-8 weeks, 18-21 g) can be used in toxicity studies of LpA-I-PTX particles. Groups of six mice each receives injections of 1.5 ml of PBS via the intraperitoneal route, containing respective doses of 30 mg/kg and 40 mg/kg of Taxol® , 40 mg/kg and 70 mg/kg of Abraxane® and 85 mg/kg and 100 mg/kg of LpA-I-PTX. The injections are administered on days 1, 2 and 3. A control group is injected with the LpA-I vehicle. The weights and the health of the mice are monitored for 30 days. Weighings are performed once a day for the first 7 days and twice a week for the remaining monitoring period.

Screening for LpA-I-Paclitaxel Incorporation

Cultured cells are incubated with the LpA-I-PTX complex, labeled with $^{14}$C-PTX. Subsequent to the incubation period, cells are trypsinized and the radioactivity of the lysate is determined to measure the extent of incorporation of the PTX into the cells.

Tumor Suppression

As disclosed in US Pat Appl 20090110739, mice (nu/nu strain, from Harlan, 4-5 weeks old and about 18-22 grams) can be used for tumor suppression studies. Group of 5 mice each animal is implanted subcutaneously with cells harvested from tissue culture of MDA-MB-435 breast cancer cells. When tumor grows to approximately 125 mm$^3$ (100-150 mm$^3$), animals are pair-matched by tumor size into treatment and control groups. Either PTX (TAXOL®; 30 mg/kg paclitaxel) or LpA-I-PTX (80 mg/kg paclitaxel) is intravenously administered to the animals via tail vein. Clinical observations, body weights and tumor volume measurements are made twice a week once tumors become measureable. It should be noted that TAXOL® is formulated with a detergent Cremophor that in itself is cytotoxic and is also the source of numerous side effects during chemotherapy. The Cremophor content of TAXOL® is about 80× that of paclitaxel per ml.

Example 4

Use of Discoidal LpA-I-Amphotericin B Complexes

Yeast Growth Inhibition

As disclosed in U.S. Pat. No. 7,824,709, cultures of the yeast *Saccharomyces cerevisiae* are grown in yeast extract peptone glucose broth medium (YEPD; Teknova, Hollister, CA). Twenty microliters of a saturated overnight culture is used to inoculate 5 ml of YEPD in the absence or presence of either AMB or LpA-I-AMB formulation. Cultures are grown for 16 h at 30° C. with rotation, and the extent of culture growth is monitored by measuring sample turbidity at 600 nm.

Pathogenic Fungi Growth Inhibition

As disclosed in U.S. Pat. No. 7,824,709, microtiter broth growth inhibition assays are conducted with three species of pathogenic fungi: *Candida albicans* [American Type Culture Collection (ATCC) strain 90028], *Aspergillus fumigatus* (ATCC strain 16424), and *Cryptococcus neoformans* (isolate H99, ATCC strain 208821). Fungi are cultured in RPMI 1640 medium buffered with MOPS to pH 7.0. The final inoculum is 1×10$^6$ cells/ml. Experiments are performed in triplicate at 37° C. for 48 h according to established protocols. Inhibitory activity is determined from cultures grown with varying amounts of either AMB or LpA-I-AMB formulation ranging from 0.01 to 16 ug/ml.

Erythrocyte Hemolysis

As disclosed in U.S. Pat. No. 7,824,709, whole blood collected from healthy volunteers is centrifuged for 3 min at 1,000 g. The plasma fraction is removed, and the red blood cells (RBCs) are diluted 1:10 in PBS (or 150 mM NaCl, pH 7-7.4). Deionized water is used as a 100% lysis control. Aliquots (25 ul) of diluted RBCs are transferred to 1.5 ml microfuge tubes, and a given amount of either AMB or LpA-I-AMB or buffer is added to a final volume of 500 ul. Reaction tubes are incubated at 37° C. for 1 or 20 h and centrifuged at 1,000 g for 4 mM. An aliquot (200 ul) of the supernatant is added to wells of a microtiter plate containing 25 ul of Drabkins reagent, and sample absorbance at 540 nm is measured on a plate reader.

Cell Viability

As disclosed in U.S. Pat. No. 7,824,709, HepG2 (human hepatoma) cells are grown in MEM (Gibco) supplemented with 4 mM L-glutamine, 0.1 mM nonessential amino acids, 1.0 mM sodium pyruvate, and 10% fetal bovine serum. Cells are split twice weekly into fresh medium and maintained at 37° C. in a humidified 5% CO$_2$ atmosphere. For experiments, the cells are seeded on 24-well plates with 2 ml of complete medium, 2×10$^4$ cells per well. The medium is aspirated after 48 h, the cells are washed with MEM containing 4% FBS, and the wells are each given 2 ml of fresh MEM with 4% FBS. Treatment of cells with either AMB or LpA-I-AMB commences 48 h after seeding at concentrations ranging from 0 to 25 ug/ml. Assays are performed in triplicate. After 20 h of culturing in the presence or absence of antibiotic, cell viability is measured spectrophotometrically using the 3-(4, 5-dimethylthiazolyl-2)-2, 5-diphenyltetrazolium bromide assay as described by the manufacturer (Sigma). Values are expressed as percentages of absorbance of untreated control cells.

In Vivo Toxicity

As disclosed in U.S. Pat. No. 7,824,709, female BALB/c mice (6-8 weeks old) are divided into groups of three mice each and administered 1, 2, 5, 10, and 15 mg/kg either AMB or LpA-I-AMB intraperitoneally (0.1 ml total volume). At 2 and 6 h after injection, and every 24 h thereafter for 7 days, mice are observed for weight loss or abnormalities in appearance and behavior. Blood is drawn 24 h after drug administration, and liver (alanine aminotransferase and aspartate aminotransferase) and kidney (urea and creatinine) function markers are analyzed.

Efficacy

As disclosed in U.S. Pat. No. 7,824,709, female BALB/c mice (6-8 weeks old) are divided into groups of 10 mice each for a dose-response study of either AMB or LpA-I-AMB efficacy. Each group is inoculated with $5 \times 10^5$ blastospores of *Candida albicans* (ATCC strain 90028). Two hours after inoculation, mice are treated with PBS or 0.25, 0.5, 1.0, 2.5, or 5 mg/kg of either AMB or LpA-I-AMB. Treatment is administered once a day for 5 days. Over the course of the 28 day observation period, mice are examined twice daily for mortality, weight loss, failure to take food or water, and abnormalities in appearance and behavior.

INCORPORATION BY REFERENCE

The references cited herein throughout, to the extent that they provide exemplary procedural or other details supplementary to those set forth herein, are all specifically incorporated herein by reference.

All of the patents and publications cited herein are hereby incorporated by reference. Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List, or in the text itself; and, each of these documents or references ("herein-cited references"), as well as each document or reference cited in each of the herein-cited references (including any manufacturer's specifications, instructions, etc.), is hereby expressly incorporated herein by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

U.S. PATENT DOCUMENTS

Sigalov, U.S. Pat. No. 8,278,271, Oct. 2, 2012
Sigalov, U.S. Pat. No. 8,614,188, Dec. 24, 2013
Sigalov. US 20130039948. 2013.
Sigalov, U.S. Pat. No. 9,981,004, May 29, 2018
Sigalov, U.S. Pat. No. 8,513,185, Aug. 20, 2013
Sigalov. US 20110256224. 2011.
Sigalov. US 20130045161. 2013.

PUBLICATIONS

Banga. Therapeutic peptides and proteins: formulation, processing, and delivery systems. 2nd ed. Boca Raton, FL: Taylor & Francis Group; 2006.
Bennasroune, et al., Transmembrane peptides as inhibitors of ErbB receptor signaling, Mol Biol Cell 2004, 15:3464-3474.
Shen and Sigalov, Novel TREM-1 Inhibitors Attenuate Tumor Growth and Prolong Survival in Experimental Pancreatic Cancer, Mol Pharm 2017, 14:4572-4582.
Shen and Sigalov, Rationally designed ligand-independent peptide inhibitors of TREM-1 ameliorate collagen-induced arthritis, J Cell Mol Med 2017, 21:2524-2534.
Shen and Sigalov, SARS Coronavirus Fusion Peptide-Derived Sequence Suppresses Collagen-Induced Arthritis in DBA/1J Mice, Sci Rep 2016, 6:28672.
Sigalov, A novel ligand-independent peptide inhibitor of TREM-1 suppresses tumor growth in human lung cancer xenografts and prolongs survival of mice with lipopolysaccharide-induced septic shock, Int Immunopharmacol 2014, 21:208-219.

I claim:

1. A composition comprising a reconstituted lipoprotein nanoparticle comprising:
   i a plurality of phospholipids;
   ii) at least one apolipoprotein fragment comprising a modification, wherein said modification comprises one or two sulfoxidized methionine residues and not a modified tyrosine residue, wherein only protein constituents are oxidized; and
   iii) at least one therapeutic agent attached to said nanoparticle.

2. The composition of claim 1, wherein said at least one apolipoprotein fragment further comprises said modification selected from the group consisting of halogenation, hydroxylation, peroxidation, dimerization, sulfoxidation and nitration.

3. The composition of claim 1, wherein said at least one apolipoprotein fragment is selected from the group consisting of an apolipoprotein A-I, an apolipoprotein A-II and an apolipoprotein A-IV.

4. The composition of claim 1, wherein said at least one apolipoprotein fragment is selected from the group consisting of an apolipoprotein C-I, an apolipoprotein C-II and an apolipoprotein C-III.

5. The composition of claim 1, wherein said at least one apolipoprotein fragment is an apolipoprotein E.

6. The composition of claim 1, wherein said nanoparticle further comprises a targeting agent selected from the group consisting of an apo E-derived lipopeptide, an apo A-I mimetic peptide, a murine MDA2 antibody, a murine E06 antibody, a human IK17 antibody and a gold particle.

7. The composition of claim 1, wherein said at least one apolipoprotein fragment is an amphipathic apolipoprotein fragment.

8. The composition of claim 1, wherein said therapeutic agent is selected from the group consisting of anticancer agents, antibacterial agents, antiviral agents, autoimmune agents, anti-inflammatory agents, cardiovascular agents, antioxidant agents, and therapeutic peptide agents.

9. The composition of claim 1, wherein said therapeutic agent is selected from the group consisting of paclitaxel, valrubicin, doxorubicin, taxotere, campotechin, and etoposide.

10. The composition of claim 1, wherein said plurality of phospholipids further comprise at least one lipid that is selected from the group consisting of a cholesterol, a cholesteryl ester, a glycolipid, a sphingolipid, a cationic lipid, a diacylglycerol, and a triacylglycerol.

11. The composition of claim 1, wherein said plurality of phospholipids are selected from the group consisting of phosphatidylcholine (PC), phosphatidylethanolamine (PE), phosphatidylserine (PS), phosphatidylinositol (PI), phosphatidylglycerol (PG), cardiolipin (CL), sphingomyelin (SM), and phosphatidic acid (PA).

12. The composition of claim 10, wherein said cationic lipid is 1,2-dioleoyl-3-trimethylammonium-propane (DOTAP).

13. The composition of claim 1, wherein said plurality of phospholipids further comprises polyethylene glycol.

14. The composition of claim 1, wherein said nanoparticle has a diameter of less than about 100 nm.

15. The composition of claim 1, wherein said composition is a pharmaceutical composition comprising a pharmaceutically acceptable carrier.

16. The composition of claim 1, wherein said nanoparticle has a diameter ranging between approximately 5-25 nanometers.

17. The composition of claim 1, wherein said plurality of phospholipids further comprise a chelating agent.

18. The composition of claim 1, wherein at least one of said plurality of phospholipids is modified.

19. The composition of claim 1, wherein said modified apolipoprotein fragment comprises a secondary structure that is unchanged as compared to an unmodified apolipoprotein.

20. The composition of claim 1, wherein said nanoparticle is discoidal.

21. A composition, comprising a reconstituted lipoprotein nanoparticle comprising:
   i) a triglyceride-cholesterol ester core surrounded by a plurality of phospholipids;
   ii) at least one apolipoprotein fragment comprising a modification, wherein said modification comprises one or two sulfoxidized methionine residues and not a modified tyrosine residue, wherein only protein constituents are oxidized; and
   iii) at least one therapeutic agent attached to said nanoparticle.

22. The composition of claim 21, wherein said at least one apolipoprotein fragment further comprises said modification selected from the group consisting of halogenation, hydroxylation, peroxidation, dimerization, sulfoxidation and nitration.

23. The composition of claim 21, wherein said at least one apolipoprotein fragment is selected from the group consisting of an apolipoprotein A-I, an apolipoprotein A-II and an apolipoprotein A-IV.

24. The composition of claim 21, wherein said at least one apolipoprotein fragment is selected from the group consisting of an apolipoprotein C-I, an apolipoprotein C-II and an apolipoprotein C-III.

25. The composition of claim 21, wherein said at least one apolipoprotein fragment is apolipoprotein E.

26. The composition of claim 21, wherein said nanoparticle further comprises a targeting agent selected from the group consisting of an apo E-derived lipopeptide, an apo A-I mimetic peptide, a murine MDA2 antibody, a murine E06 antibody, a human IK17 antibody and a gold particle.

27. The composition of claim 21, wherein at least one said apolipoprotein fragments is an amphipathic apolipoprotein.

28. The composition of claim 21, wherein said therapeutic agent is selected from the group consisting of anticancer agents, antibacterial agents, antiviral agents, autoimmune agents, anti-inflammatory agents, cardiovascular agents, antioxidant agents and therapeutic peptide agents.

29. The composition of claim 21, wherein said therapeutic agent is selected from the group consisting of paclitaxel, valrubicin, doxorubicin, taxotere, campotechin, and etoposide.

30. The composition of claim 21, wherein said plurality of phospholipids further comprise at least one lipid that is selected from the group consisting of a cholesterol, a cholesteryl ester, a glycolipid, a sphingolipid, a cationic lipid, a diacylglycerol, and a triacylglycerol.

31. The composition of claim 21, wherein said plurality of phospholipids are selected from the group consisting of phosphatidylcholine (PC), phosphatidylethanolamine (PE), phosphatidylserine (PS), phosphatidylinositol (PI), phosphatidylglycerol (PG), cardiolipin (CL), sphingomyelin (SM), and phosphatidic acid (PA).

32. The composition of claim 30, wherein said cationic lipid is 1,2-dioleoyl-3-trimethylammonium-propane (DOTAP).

33. The composition of claim 21, wherein said plurality of phospholipids further comprise polyethylene glycol.

34. The composition of claim 21, wherein said nanoparticle has a diameter of less than about 100 nm.

35. The composition of claim 21, wherein said nanoparticle is a pharmaceutical composition comprising a pharmaceutically acceptable carrier.

36. The composition of claim 21, wherein said nanoparticle has a diameter ranging between approximately 5-25 nanometers.

37. The composition of claim 21, wherein said plurality of phospholipids further comprise a chelating agent.

38. The composition of claim 21, wherein at least one of said plurality of phospholipids is modified.

39. The composition of claim 21, wherein said modified apolipoprotein fragment comprises a secondary structure that is unchanged as compared to an unmodified apolipoprotein.

40. The composition of claim 21, wherein said nanoparticle is spherical.

* * * * *

SEQUENCE LISTING

```
<160> NUMBER OF SEQ ID NOS: 52

<210> SEQ ID NO 1
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: The residue at this position is methionine
      sulfoxide.

<400> SEQUENCE: 1

Pro Tyr Leu Asp Asp Phe Gln Lys Lys Trp Gln Glu Glu Xaa Glu Leu
```

```
1               5                   10                  15
Arg Gln Lys

<210> SEQ ID NO 2
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: The residue at this position is methionine
      sulfoxide.

<400> SEQUENCE: 2

Pro Leu Gly Glu Glu Xaa Arg Asp Arg Ala Arg Ala His Val Asp Ala
1               5                   10                  15

Leu Arg Thr His Leu Ala
            20

<210> SEQ ID NO 3
<211> LENGTH: 22
<212> TYPE: PRT
<213> ORGANISM: Artificial Sequence
<220> FEATURE:
<223> OTHER INFORMATION: Synthetic

<400> SEQUENCE: 3

Pro Tyr Leu Asp Asp Phe Gln Lys Lys Trp Gln Glu Glu Met Glu Leu
1               5                   10                  15

Tyr Arg Gln Lys Val Glu
            20

<210> SEQ ID NO 4
<211> LENGTH: 22
<212> TYPE: PRT
<213> ORGANISM: Artificial Sequence
<220> FEATURE:
<223> OTHER INFORMATION: Synthetic

<400> SEQUENCE: 4

Pro Leu Gly Glu Glu Met Arg Asp Arg Ala Arg Ala His Val Asp Ala
1               5                   10                  15

Leu Arg Thr His Leu Ala
            20

<210> SEQ ID NO 5
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: The residue at this position is methionine
      sulfoxide.

<400> SEQUENCE: 5

Pro Tyr Leu Asp Asp Phe Gln Lys Lys Trp Gln Glu Glu Xaa Glu Leu
1               5                   10                  15

Tyr Arg Gln Lys Val Glu Arg Gly Asp
            20                  25
```

```
<210> SEQ ID NO 6
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: The residue at this position is methionine
      sulfoxide.

<400> SEQUENCE: 6

Pro Leu Gly Glu Glu Met Arg Asp Arg Ala Arg Ala His Val Asp Ala
1               5                   10                  15

Leu Arg Thr His Leu Ala Arg Gly Asp
            20                  25

<210> SEQ ID NO 7
<211> LENGTH: 25
<212> TYPE: PRT
<213> ORGANISM: Artificial Sequence
<220> FEATURE:
<223> OTHER INFORMATION: Synthetic

<400> SEQUENCE: 7

Pro Tyr Leu Asp Asp Phe Gln Lys Lys Trp Gln Glu Glu Met Glu Leu
1               5                   10                  15

Tyr Arg Gln Lys Val Glu Arg Gly Asp
            20                  25

<210> SEQ ID NO 8
<211> LENGTH: 25
<212> TYPE: PRT
<213> ORGANISM: Artificial Sequence
<220> FEATURE:
<223> OTHER INFORMATION: Synthetic

<400> SEQUENCE: 8

Pro Leu Gly Glu Glu Met Arg Asp Arg Ala Arg Ala His Val Asp Ala
1               5                   10                  15

Leu Arg Thr His Leu Ala Arg Gly Asp
            20                  25

<210> SEQ ID NO 9
<211> LENGTH: 22
<212> TYPE: PRT
<213> ORGANISM: Artificial Sequence
<220> FEATURE:
<223> OTHER INFORMATION: Synthetic

<400> SEQUENCE: 9

Leu Lys Leu Leu Asp Asn Trp Asp Ser Val Thr Ser Thr Phe Ser Lys
1               5                   10                  15

Leu Arg Glu Gln Leu Gly
            20

<210> SEQ ID NO 10
<211> LENGTH: 22
<212> TYPE: PRT
<213> ORGANISM: Artificial Sequence
<220> FEATURE:
<223> OTHER INFORMATION: Synthetic

<400> SEQUENCE: 10

Pro Val Thr Gln Glu Phe Trp Asp Asn Leu Glu Lys Glu Thr Glu Gly
```

```
                 1               5                  10                  15

Leu Arg Gln Glu Met Ser
            20

<210> SEQ ID NO 11
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(21)
<223> OTHER INFORMATION: The residue at this position is methionine
      sulfoxide.

<400> SEQUENCE: 11

Pro Val Thr Gln Glu Phe Trp Asp Asn Leu Glu Lys Glu Thr Glu Gly
1               5                   10                  15

Leu Arg Gln Glu Met Ser
            20

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

Lys Asp Leu Glu Glu Val Lys Ala Lys Val Gln
1               5                   10

<210> SEQ ID NO 13
<211> LENGTH: 22
<212> TYPE: PRT
<213> ORGANISM: Artificial Sequence
<220> FEATURE:
<223> OTHER INFORMATION: Synthetic

<400> SEQUENCE: 13

Pro Leu Arg Ala Glu Leu Gln Glu Gly Ala Arg Gln Lys Leu His Glu
1               5                   10                  15

Leu Gln Glu Lys Leu Ser
            20

<210> SEQ ID NO 14
<211> LENGTH: 22
<212> TYPE: PRT
<213> ORGANISM: Artificial Sequence
<220> FEATURE:
<223> OTHER INFORMATION: Synthetic

<400> SEQUENCE: 14

Pro Tyr Ser Asp Glu Leu Arg Gln Arg Leu Ala Ala Arg Leu Glu Ala
1               5                   10                  15

Leu Lys Glu Asn Gly Gly
            20

<210> SEQ ID NO 15
<211> LENGTH: 22
<212> TYPE: PRT
<213> ORGANISM: Artificial Sequence
<220> FEATURE:
<223> OTHER INFORMATION: Synthetic
```

```
<400> SEQUENCE: 15

Ala Arg Leu Ala Glu Tyr His Ala Lys Ala Thr Glu His Leu Ser Thr
1               5                   10                  15

Leu Ser Glu Lys Ala Lys
            20

<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

Pro Ala Leu Glu Asp Leu Arg Gln Gly Leu Leu
1               5                   10

<210> SEQ ID NO 17
<211> LENGTH: 22
<212> TYPE: PRT
<213> ORGANISM: Artificial Sequence
<220> FEATURE:
<223> OTHER INFORMATION: Synthetic

<400> SEQUENCE: 17

Pro Val Leu Glu Ser Phe Lys Val Ser Phe Leu Ser Ala Leu Glu Glu
1               5                   10                  15

Tyr Thr Lys Lys Leu Asn
            20

<210> SEQ ID NO 18
<211> LENGTH: 22
<212> TYPE: PRT
<213> ORGANISM: Artificial Sequence
<220> FEATURE:
<223> OTHER INFORMATION: Synthetic

<400> SEQUENCE: 18

Ser Leu Val Ser Gln Tyr Phe Gln Thr Val Thr Asp Tyr Gly Lys Asp
1               5                   10                  15

Leu Met Glu Lys Val Lys
            20

<210> SEQ ID NO 19
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: The residue at this position is methionine
      sulfoxide.

<400> SEQUENCE: 19

Ser Leu Val Ser Gln Tyr Phe Gln Thr Val Thr Asp Tyr Gly Lys Asp
1               5                   10                  15

Leu Xaa Glu Lys Val Lys
            20

<210> SEQ ID NO 20
<211> LENGTH: 11
<212> TYPE: PRT
<213> ORGANISM: Artificial Sequence
```

```
<220> FEATURE:
<223> OTHER INFORMATION: Synthetic

<400> SEQUENCE: 20

Ser Tyr Phe Glu Lys Ser Lys Glu Gln Leu Thr
1               5                   10

<210> SEQ ID NO 21
<211> LENGTH: 20
<212> TYPE: PRT
<213> ORGANISM: Artificial Sequence
<220> FEATURE:
<223> OTHER INFORMATION: Synthetic

<400> SEQUENCE: 21

Pro Leu Ile Lys Lys Ala Gly Thr Glu Leu Val Asn Phe Leu Ser Tyr
1               5                   10                  15

Phe Val Glu Leu
            20

<210> SEQ ID NO 22
<211> LENGTH: 21
<212> TYPE: PRT
<213> ORGANISM: Artificial Sequence
<220> FEATURE:
<223> OTHER INFORMATION: Synthetic

<400> SEQUENCE: 22

Gly Ser Val Gln Thr Ile Val Phe Gln Pro Gln Leu Ala Ser Arg Thr
1               5                   10                  15

Pro Thr Gly Gln Ser
            20

<210> SEQ ID NO 23
<211> LENGTH: 25
<212> TYPE: PRT
<213> ORGANISM: Artificial Sequence
<220> FEATURE:
<223> OTHER INFORMATION: Synthetic

<400> SEQUENCE: 23

Leu Lys Leu Leu Asp Asn Trp Asp Ser Val Thr Ser Thr Phe Ser Lys
1               5                   10                  15

Leu Arg Glu Gln Leu Gly Arg Gly Asp
            20                  25

<210> SEQ ID NO 24
<211> LENGTH: 25
<212> TYPE: PRT
<213> ORGANISM: Artificial Sequence
<220> FEATURE:
<223> OTHER INFORMATION: Synthetic

<400> SEQUENCE: 24

Pro Val Thr Gln Glu Phe Trp Asp Asn Leu Glu Lys Glu Thr Glu Gly
1               5                   10                  15

Leu Arg Gln Glu Met Ser Arg Gly Asp
            20                  25

<210> SEQ ID NO 25
<211> LENGTH: 25
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (21)..(21)
<223> OTHER INFORMATION: The residue at this position is methionine
      sulfoxide.

<400> SEQUENCE: 25

Pro Val Thr Gln Glu Phe Trp Asp Asn Leu Glu Lys Glu Thr Glu Gly
1               5                   10                  15

Leu Arg Gln Glu Xaa Ser Arg Gly Asp
            20                  25

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Lys Asp Leu Glu Glu Val Lys Ala Lys Val Gln Arg Gly Asp
1               5                   10

<210> SEQ ID NO 27
<211> LENGTH: 25
<212> TYPE: PRT
<213> ORGANISM: Artificial Sequence
<220> FEATURE:
<223> OTHER INFORMATION: Synthetic

<400> SEQUENCE: 27

Pro Leu Arg Ala Glu Leu Gln Glu Gly Ala Arg Gln Lys Leu His Glu
1               5                   10                  15

Leu Gln Glu Lys Leu Ser Arg Gly Asp
            20                  25

<210> SEQ ID NO 28
<211> LENGTH: 25
<212> TYPE: PRT
<213> ORGANISM: Artificial Sequence
<220> FEATURE:
<223> OTHER INFORMATION: Synthetic

<400> SEQUENCE: 28

Pro Tyr Ser Asp Glu Leu Arg Gln Arg Leu Ala Ala Arg Leu Glu Ala
1               5                   10                  15

Leu Lys Glu Asn Gly Gly Arg Gly Asp
            20                  25

<210> SEQ ID NO 29
<211> LENGTH: 25
<212> TYPE: PRT
<213> ORGANISM: Artificial Sequence
<220> FEATURE:
<223> OTHER INFORMATION: Synthetic

<400> SEQUENCE: 29

Ala Arg Leu Ala Glu Tyr His Ala Lys Ala Thr Glu His Leu Ser Thr
1               5                   10                  15

Leu Ser Glu Lys Ala Lys Arg Gly Asp
            20                  25

<210> SEQ ID NO 30
<211> LENGTH: 14
<212> TYPE: PRT
```

```
<213> ORGANISM: Artificial Sequence
<220> FEATURE:
<223> OTHER INFORMATION: Synthetic

<400> SEQUENCE: 30

Pro Ala Leu Glu Asp Leu Arg Gln Gly Leu Leu Arg Gly Asp
1               5                   10

<210> SEQ ID NO 31
<211> LENGTH: 25
<212> TYPE: PRT
<213> ORGANISM: Artificial Sequence
<220> FEATURE:
<223> OTHER INFORMATION: Synthetic

<400> SEQUENCE: 31

Pro Val Leu Glu Ser Phe Lys Val Ser Phe Leu Ser Ala Leu Glu Glu
1               5                   10                  15

Tyr Thr Lys Lys Leu Asn Arg Gly Asp
            20                  25

<210> SEQ ID NO 32
<211> LENGTH: 25
<212> TYPE: PRT
<213> ORGANISM: Artificial Sequence
<220> FEATURE:
<223> OTHER INFORMATION: Synthetic

<400> SEQUENCE: 32

Ser Leu Val Ser Gln Tyr Phe Gln Thr Val Thr Asp Tyr Gly Lys Asp
1               5                   10                  15

Leu Met Glu Lys Val Lys Arg Gly Asp
            20                  25

<210> SEQ ID NO 33
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: The residue at this position is methionine
      sulfoxide.

<400> SEQUENCE: 33

Ser Leu Val Ser Gln Tyr Phe Gln Thr Val Thr Asp Tyr Gly Lys Asp
1               5                   10                  15

Leu Xaa Glu Lys Val Lys Arg Gly Asp
            20                  25

<210> SEQ ID NO 34
<211> LENGTH: 14
<212> TYPE: PRT
<213> ORGANISM: Artificial Sequence
<220> FEATURE:
<223> OTHER INFORMATION: Synthetic

<400> SEQUENCE: 34

Ser Tyr Phe Glu Lys Ser Lys Glu Gln Leu Thr Arg Gly Asp
1               5                   10

<210> SEQ ID NO 35
<211> LENGTH: 23
<212> TYPE: PRT
```

```
<213> ORGANISM: Artificial Sequence
<220> FEATURE:
<223> OTHER INFORMATION: Synthetic

<400> SEQUENCE: 35

Pro Leu Ile Lys Lys Ala Gly Thr Glu Leu Val Asn Phe Leu Ser Tyr
1               5                   10                  15

Phe Val Glu Leu Arg Gly Asp
            20

<210> SEQ ID NO 36
<211> LENGTH: 24
<212> TYPE: PRT
<213> ORGANISM: Artificial Sequence
<220> FEATURE:
<223> OTHER INFORMATION: Synthetic

<400> SEQUENCE: 36

Gly Ser Val Gln Thr Ile Val Phe Gln Pro Gln Leu Ala Ser Arg Thr
1               5                   10                  15

Pro Thr Gly Gln Ser Arg Gly Asp
            20

<210> SEQ ID NO 37
<211> LENGTH: 18
<212> TYPE: PRT
<213> ORGANISM: Artificial Sequence
<220> FEATURE:
<223> OTHER INFORMATION: Synthetic

<400> SEQUENCE: 37

Ser Glu Ala Glu Asp Ala Ser Leu Leu Ser Phe Met Gln Gly Tyr Met
1               5                   10                  15

Lys His

<210> SEQ ID NO 38
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: The residue at this position is methionine
      sulfoxide.
<220> FEATURE:
<221> NAME/KEY: misc_feature
<222> LOCATION: (17)..(17)
<223> OTHER INFORMATION: Xaa can be any naturally occurring amino acid

<400> SEQUENCE: 38

Ser Glu Ala Glu Asp Ala Ser Leu Leu Ser Phe Met Gln Gly Tyr Met
1               5                   10                  15

Xaa Lys His

<210> SEQ ID NO 39
<211> LENGTH: 9
<212> TYPE: PRT
<213> ORGANISM: Artificial Sequence
<220> FEATURE:
<223> OTHER INFORMATION: Synthetic

<400> SEQUENCE: 39

Thr Ala Lys Asp Ala Leu Ser Ser Val
1               5
```

```
<210> SEQ ID NO 40
<211> LENGTH: 13
<212> TYPE: PRT
<213> ORGANISM: Artificial Sequence
<220> FEATURE:
<223> OTHER INFORMATION: Synthetic

<400> SEQUENCE: 40

Gln Glu Ser Gln Val Ala Gln Gln Ala Arg Gly Trp Val
1               5                   10

<210> SEQ ID NO 41
<211> LENGTH: 18
<212> TYPE: PRT
<213> ORGANISM: Artificial Sequence
<220> FEATURE:
<223> OTHER INFORMATION: Synthetic

<400> SEQUENCE: 41

Phe Ser Ser Leu Lys Asp Tyr Trp Ser Thr Val Lys Asp Lys Phe Ser
1               5                   10                  15

Glu Phe

<210> SEQ ID NO 42
<211> LENGTH: 12
<212> TYPE: PRT
<213> ORGANISM: Artificial Sequence
<220> FEATURE:
<223> OTHER INFORMATION: Synthetic

<400> SEQUENCE: 42

Thr Pro Asn Val Ser Ser Ala Leu Glu Lys Leu Lys
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Synthetic

<400> SEQUENCE: 43

Phe Gly Asn Thr Leu Asp Glu Lys Ala Arg Asp Leu Ile Ser Arg Ile
1               5                   10                  15

Lys

<210> SEQ ID NO 44
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The residue at this position is methionine
      sulfoxide.

<400> SEQUENCE: 44

Lys Xaa Arg Asp Trp Phe Ser Asp Thr Phe Gln Lys Val Lys Asp Lys
1               5                   10                  15

Leu Lys

<210> SEQ ID NO 45
```

```
<211> LENGTH: 24
<212> TYPE: PRT
<213> ORGANISM: Artificial Sequence
<220> FEATURE:
<223> OTHER INFORMATION: Synthetic

<400> SEQUENCE: 45

Thr Gln Val Lys Glu Ser Leu Ser Ser Tyr Trp Glu Ser Ala Lys Thr
1               5                   10                  15
Ala Ala Gln Asn Leu Tyr Glu Lys
            20

<210> SEQ ID NO 46
<211> LENGTH: 26
<212> TYPE: PRT
<213> ORGANISM: Artificial Sequence
<220> FEATURE:
<223> OTHER INFORMATION: Synthetic

<400> SEQUENCE: 46

Asp Glu Lys Leu Arg Asp Leu Tyr Ser Lys Ser Thr Ala Ala Met Ser
1               5                   10                  15
Thr Tyr Thr Gly Ile Phe Thr Asp Gln Val
            20                  25

<210> SEQ ID NO 47
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: The residue at this position is methionine
      sulfoxide.

<400> SEQUENCE: 47

Asp Glu Lys Leu Arg Asp Leu Tyr Ser Lys Ser Thr Ala Ala Xaa Ser
1               5                   10                  15
Thr Tyr Thr Gly Ile Phe Thr Asp Gln Val
            20                  25

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gly Leu Arg Ile Leu Leu Leu Lys Val
1               5

<210> SEQ ID NO 49
<211> LENGTH: 12
<212> TYPE: PRT
<213> ORGANISM: Artificial Sequence
<220> FEATURE:
<223> OTHER INFORMATION: Synthetic

<400> SEQUENCE: 49

Leu Gln Glu Glu Asp Ala Gly Glu Tyr Gly Cys Met
1               5                   10

<210> SEQ ID NO 50
```

```
<211> LENGTH: 17
<212> TYPE: PRT
<213> ORGANISM: Artificial Sequence
<220> FEATURE:
<223> OTHER INFORMATION: Synthetic

<400> SEQUENCE: 50

Leu Gln Val Thr Asp Ser Gly Leu Tyr Arg Cys Val Ile Tyr His Pro
1               5                   10                  15

Pro

<210> SEQ ID NO 51
<211> LENGTH: 11
<212> TYPE: PRT
<213> ORGANISM: Artificial Sequence
<220> FEATURE:
<223> OTHER INFORMATION: Synthetic

<400> SEQUENCE: 51

Met Trp Lys Thr Pro Thr Leu Lys Tyr Phe Gly
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic

<400> SEQUENCE: 52

Met Trp Gly Thr Pro Thr Leu Gly Tyr Phe Gly
1               5                   10
```